United States Patent
Arruda et al.

(10) Patent No.: US 7,087,601 B2
(45) Date of Patent: Aug. 8, 2006

(54) METABOTROPIC GLUTAMATE RECEPTOR-5 MODULATORS

(75) Inventors: Jeannie Arruda, San Diego, CA (US); Celine Bonnefous, San Diego, CA (US); Brian T. Campbell, San Diego, CA (US); Rowena V. Cube, San Diego, CA (US); Benito Munoz, San Diego, CA (US); Brian Stearns, San Diego, CA (US); Jean-Michel Vernier, San Diego, CA (US); Bowei Wang, San Diego, CA (US); Xiumin Zhao, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 8 days.

(21) Appl. No.: 10/497,452

(22) PCT Filed: Nov. 26, 2002

(86) PCT No.: PCT/US02/38201

§ 371 (c)(1),
(2), (4) Date: Nov. 9, 2004

(87) PCT Pub. No.: WO03/048137

PCT Pub. Date: Jun. 12, 2003

(65) Prior Publication Data

US 2005/0065340 A1    Mar. 24, 2005

Related U.S. Application Data

(60) Provisional application No. 60/334,547, filed on Nov. 30, 2001.

(51) Int. Cl.
*A61K 31/5383* (2006.01)
*A61K 31/437* (2006.01)
*C07D 413/14* (2006.01)
*C07D 491/048* (2006.01)

(52) U.S. Cl. ............... 514/234.2; 514/302; 544/127; 546/115

(58) Field of Classification Search .............. None
See application file for complete search history.

(56) References Cited

U.S. PATENT DOCUMENTS

| 3,458,506 A | | 7/1969 | Bloom et al. |
| 3,899,506 A | | 8/1975 | Shen et al. |
| 4,038,396 A | * | 7/1977 | Shen et al. .............. 514/302 |
| 5,077,408 A | * | 12/1991 | Guillaumet et al. ........ 546/116 |

FOREIGN PATENT DOCUMENTS

| WO | WO 96 11917 | 4/1996 |
| WO | WO 02 51821 | 7/2002 |

OTHER PUBLICATIONS

Bathini et al., "A convenient synthesis of substituted oxazolo[5,4-b]pyridines using lead tetraacetate as oxidative cyclizing agent," Synthetic Communications (1991), 21(2), 215-22.*
Flouzat et al., "A new convenient synthesis of 2-aryl- and 2-heteroaryloxazolo[5,4-b]pyridines," Synthesis (1990), (1), 64-6.*
Frazer et al., "Oxazolopyridines and oxazoloquinolines. I. 2'-Alkyland 2'-aryl derivatives of oxazolo[4',5',3,4]pyridine and oxazolo[4',5',3,4]quinoline," Journal of the Chemical Society, Abstracts (1956), 1781-4.*
Bathini, et al., Synthetic Communications, vol. 21 (2), pp. 215-22, 1991.
Flouzat, et al., Synthesis, vol. 1, pp. 64-6, 1990.
Frazer, et al., Journal of the Chemical Society, Abstracts, pp. 1781-4, 1956.

* cited by examiner

*Primary Examiner*—Taofiq Solola
*Assistant Examiner*—Andrew B. Freistein
(74) *Attorney, Agent, or Firm*—David L. Rose; David A. Rubin

(57) ABSTRACT

Phenyl compounds substituted at the 1-position with a fused bicyclo moeity formed from a five-membered heterocycle fused to a six-membered carbocycle, to a six-membered aryl, or to a six-membered hetaryl, and further optionally substituted at the 3,4 positions, are mGluR5 modulators useful in the treatment of psychiatric and mood disorders such as, for example, schizophrenia, anxiety, depression, and panic, as well as in the treatment of pain and other diseases.

11 Claims, No Drawings

METABOTROPIC GLUTAMATE RECEPTOR-5 MODULATORS

RELATED APPLICATION DATA

This is a National filing under 35 USC 371 of PCT/US02/38201, filed Nov. 26, 2002, which claims priority from U.S. Ser. No. 60/334,547, filed Nov. 30, 2001.

BACKGROUND OF THE INVENTION

1. Field of the Invention

The present invention is directed to phenyl compounds substituted with a fused-heterobicyclo moeity. In particular, this invention is directed to phenyl compounds substituted at the 1-position with a fused bicyclo moeity formed from a five-membered heterocycle fused to a six-membered carbocycle, to a six-membered aryl, or to a six-membered hetaryl, and further optionally substituted at the 3,4 positions, which are modulators of metabotropic glutamate receptor—subtype 5 ("mGluR5") modulators useful in the treatment of psychiatric and mood disorders such as, for example, schizophrenia, anxiety, depression, and panic, as well as in the treatment of pain, Parkinson's disease, cognitive dysfunction, epilepsy, drug addiction, drug abuse, drug withdrawal and other diseases.

2. Related Background

A major excitatory neurotransmitter in the mammalian nervous system is the glutamate molecule, which binds to neurons, thereby activating cell surface receptors. Such surface receptors are characterized as either ionotropic or metabotropic glutamate receptors. The metabotropic glutamate receptors ("mGluR") are G protein-coupled receptors that activate intracellular second messenger systems when bound to glutamate. Activation of mGluR results in a variety of cellular responses. In particular, mgluR1 and mgluR5 activate phospholipase C, which is followed by mobilizing intracellular calcium.

Modulation of metabotropic glutamate receptor subtype 5 (mGluR5) is useful in the treatment of diseases that affect the nervous system (see for example W. P. J. M Spooren et al., *Trends Pharmacol. Sci.*, 22:331–337(2001) and references cited therein). For example, recent evidence demonstrates the involvement of mGluR5 in nociceptive processes and that modulation of mGluR5 using mGluR5-selective compounds is useful in the treatment of various pain states, including acute, persistent and chronic pain [K Walker et al., *Neuropharmacology*, 40:1–9(2001); F. Bordi, A. Ugolini *Brain Res.*, 871:223–233(2001)], inflammatory pain [K Walker et al., *Neuropharmacology*, 40:10–19(2001); Bhave et al. *Nature Neurosci.* 4:417–423(2001)] and neuropathic pain [Dogrul et al. *Neurosci. Lett.* 292:115–118(2000)].

Further evidence supports the use of modulators of mGluR5 in the treatment of psychiatric and neurological disorders. For example, mGluR5-selective compounds such as 2-methyl-6-(phenylethynyl)-pyridine ("MPEP") are effective in animal models of mood disorders, including anxiety and depression [W. P. J. M Spooren et al., *J. Pharmacol. Exp. Ther.*, 295:1267–1275(2000); E. Tatarczynska et al, *Brit. J. Pharmacol.*, 132:1423–1430(2001); A. Klodzynska et al, *Pol. J. Pharmacol.*, 132:1423–1430(2001). Gene expression data from humans indicate that modulation of mGluR5 may be useful for the treatment of schizophrenia [T. Ohnuma et al, *Mol. Brain. Res.*, 56:207–217(1998); ibid, *Mol. Brain. Res.*, 85:24–31 (2000)]. Studies have also shown a role form GluR5, and the potential utility of mGluR5-modulatory compounds, play in the treatment of movement disorders such as Parkinson's disease [W. P. J. M Spooren et al., *Europ. J. Pharmacol.* 406:403–410(2000); H. Awad et al., *J. Neurosci.* 20:7871–7879(2000); K. Ossawa et al. *Neuropharmacol.* 41:413–420(2001)]. Other research supports a role form GluR5 modulation in the treatment of cognitive dysfunction [G. Riedel et al, *Neuropharmacol.* 39:1943–1951(2000)], epilepsy [A. Chapman et al, *Neuropharmacol.* 39:1567–1574(2000)] and neuroprotection [V. Bruno et al, *Neuropharmacol.* 39:2223–2230(2000)]. Studies with mGluR5 knockout mice and MPEP also suggest that modulation of these receptors may be useful in the treatment of drug addiction, drug abuse and drug withdrawal [C. Chiamulera et al. *Nature Neurosci.* 4:873–874(2001)].

International Patent Publications WO 01/12627 and WO 99/26927 describe heteropolycyclic compounds and their use as metabotropic glutamate receptor antagonists. International Patent Publications WO 96/05818, WO 00/73283, WO 00/20001, and U.S. Pat. No. 6,031,003 describe polycyclic compounds active at metabotropic glutamate receptors.

Russian Patent Nos. SU 1824402, SU 1830388, and SU 1806138 describe processes for producing 2-phenylbenzoxazole. Japanese Patent No. JP 07013369 describes an electrophotographic photoreceptor containing oxazole or thiazole derivative charge-transporting agents. International Patent Publication EP 479161 describes the synthesis of heterocyclic compounds. Japanese Patent No. JP 55038302 describes benzoxazole derivatives. German Patent No. DE 2619547 and U.S. Pat. No. 4,107,169 describe 2-arylbenzoxazoles and 2-arylbenzothiazoles. U.S. Pat. Nos. 3,772, 309, and 3,630,972 describe 2-arylbenzazoles and polybenzimidazoles. German Patent Nos. DE 2037998 and DE 2037999 describe benzazoles, benzazolinones, quinolines, indoles, benzothiazoles, benzimidazoles, and benzoxazoles. U.S. Pat. No. 3,452,036 and Japanese Patent No. JP 42015938 describe 2-substituted benzoxazoles. Dutch Patent No. NL 6607039 describes herbicidal benzazoles.

International Patent Publication No. WO 9427601 describes the preparation of [(benzoxazolylphenyl)alkoxy] alkylamines as squalene synthase inhibitors. U.S. Pat. No. 3,458,506 describes fluorescent benzazoles compounds containing cyanovinylene groups.

U.S. Pat. No. 3,647,809 describes pyridyl-1,2,4-oxadiazole derivatives. U.S. Pat. No. 4,022,901 describes 3-pyridyl-5-isothiocyanophenyl oxadiazoles. International Patent Publication WO 98/17652 describes oxadiazoles, WO 97/03967 describes various substituted aromatic compounds, and WO 94/22846 describes various heterocyclic compounds.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, and U.S. Pat. No. 5,736,297 describes ring systems useful as a photosensitive composition.

The following compounds are available from Maybridge plc, Cornwall, England:

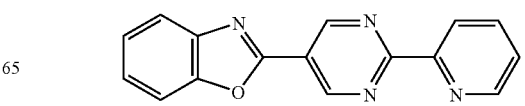

-continued

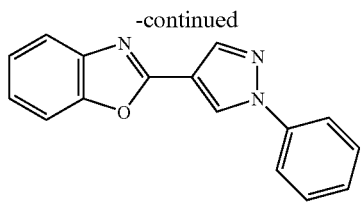

However, there remains a need for novel compounds and compositions that therapeutically inhibit mGluR5 with minimal side effects.

SUMMARY OF THE INVENTION

The present invention is directed to novel phenyl compounds substituted at the 1-position with a fused bicyclo moeity formed from a five-membered heterocycle fused to a six-membered carbocycle, to a six-membered aryl, or to a six-membered hetaryl, and further optionally substituted at the 3,4 positions, which are modulators of metabotropic glutamate receptor-5, useful in the treatment of psychiatric and mood disorders such as, for example, schizophrenia, anxiety, depression, and panic, as well as in the treatment of pain, Parkinson's disease, cognitive dysfunction, epilepsy, drug addiction, drug abuse, drug withdrawal and other diseases. This invention also provides a pharmaceutical composition which includes an effective amount of the novel phenyl compounds substituted with a fused bicyclo moeity formed from a five-membered heterocycle fused to a six-membered carbocycle, to a six-membered aryl, or to a six-membered hetaryl, and a pharmaceutically acceptable carrier.

This invention further provides a method of treatment of psychiatric and mood disorders such as, for example, schizophrenia, anxiety, depression, and panic, as well as a method of treatment of pain, Parkinson's disease, cognitive dysfunction, epilepsy, drug addiction, drug abuse and drug withdrawal by the administration of an effective amount of the novel phenyl compounds substituted with a fused bicyclo moeity formed from a five-membered heterocycle fused to a six-membered carbocycle, to a six-membered aryl, or to a six-membered hetaryl.

DETAILED DESCRIPTION OF THE INVENTION

A compound of this invention is represented by Formula (I):

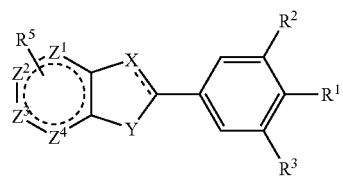

(I)

or a pharmaceutically acceptable salt thereof, wherein
X is N, CH, or NH;
Y is O, or N—$R^4$;
one of $Z^1$, $Z^2$, $Z^3$ or $Z^2$ optionally is N, or NH;
$R^1$ is —OH, halogen, or —CN; or a —$C_{1-6}$alkyl, —$C_{1-4}$alkoxyl, -cyclo$C_{3-6}$alkyl, —$C_{0-4}$alkyl-phenyl, —$C_{0-4}$alkyl-pyridyl, —$C_{0-4}$alkyl-imidazolyl, —$C_{0-4}$alkyl-pyrazolyl, —$C_{0-4}$alkyl-triazolyl, —$C_{0-4}$alkyl-tetrazolyl, —$C_{0-4}$alkyl-dioxolanyl, —$C_{0-4}$alkyl-thiazolyl, —$C_{0-4}$alkyl-piperidinyl, —$C_{0-4}$alkyl-pyrrolidinyl, —$C_{0-4}$alkyl-morpholinyl, —$C_{0-4}$alkyl-pyrimidinyl, —$C_{2-6}$alkynyl-thiazolyl, or —N($C_{0-4}$alkyl)(—$C_{0-4}$alkyl) group, wherein any of the groups is optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;
$R^2$ is hydrogen, halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;
$R^3$ is hydrogen or —$C_{1-4}$alkoxyl;
$R^4$ is —$C_{0-4}$alkyl; and
$R^5$ is H, halogen, or —$C_{1-4}$alkyl.

In one aspect, the compound of this invention is represented by Formula (I) or a pharmaceutically acceptable salt thereof, wherein
$Z^1$, $Z^2$, $Z^3$, and $Z^4$ are each CH;
X is N;
Y is O;
$R^1$ is —OH, halogen, or —CN; or a —$C_{1-6}$alkyl, —$C_{1-4}$alkoxyl, -cyclo$C_{3-6}$alkyl, —$C_{0-4}$alkyl-phenyl, —$C_{0-4}$alkyl-pyridyl, —$C_{0-4}$alkyl-imidazolyl, —$C_{0-4}$alkyl-pyrazolyl, —$C_{0-4}$alkyl-triazolyl, —$C_{0-4}$alkyl-tetrazolyl, —$C_{0-4}$alkyl-dioxolanyl, —$C_{0-4}$alkyl-thiazolyl, —$C_{0-4}$alkyl-piperidinyl, —$C_{0-4}$alkyl-pyrrolidinyl, —$C_{0-4}$alkyl-morpholinyl, —$C_{0-4}$alkyl-pyridinyl, —$C_{2-6}$alkynyl-thiazolyl, or —N($C_{0-4}$alkyl)(—$C_{0-4}$alkyl) group, wherein any of the groups is optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;
$R^2$ is hydrogen, halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;
$R^3$ is hydrogen or —$C_{1-4}$alkoxyl;
$R^4$ is —$C_{0-4}$alkyl; and
$R^5$ is H, halogen, or —$C_{1-4}$alkyl.

In an embodiment of this one aspect, the compound of this invention is represented by Formula (I) or a pharmaceutically acceptable salt thereof, wherein
$Z^1$, $Z^2$, $Z^3$, and $Z^4$ are each CH;
X is N;
Y is O;
$R^1$ is —$C_{1-6}$alkyl, optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;
$R^2$ is hydrogen, halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;
$R^3$ is hydrogen or —$C_{1-4}$alkoxyl;
$R^4$ is —$C_{0-4}$alkyl; and
$R^5$ is H, halogen, or —$C_{1-4}$alkyl.

In another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{1-6}$alkyl, optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is —$C_{0-4}$alkyl-phenyl optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In still another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{1-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is hydrogen; or —$C_{1-6}$alkyl optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In still another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{1-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is or —$NO_2$; or —N($C_{0-4}$alkyl)($C_{0-4}$alkyl) optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In still another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{1-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is —$C_{1-4}$alkoxy-phenyl optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In still another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{1-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is —$C_{1-4}$alkoxyl optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In still another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is -cyclo$C_{3-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{0-4}$alkyl-triazolyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In another embodiment of this one aspect, the compound of this invention is represented by Formula (I) or a pharmaceutically acceptable salt thereof, wherein $Z^1$, $Z^2$, $Z^3$, and $Z^4$ are each CH;

X is N;

Y is O;

$R^1$ is —$C_{0-4}$alkyl-imidazolyl or —$C_{0-4}$alkyl-pyrazolyl optionally substituted with 1–5 substituents; wherein each substituent is independently halogen, —OH, —CN, —$C_{1-6}$ alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In another embodiment of this one aspect, the compound of this invention is represented by Formula (I) or a pharmaceutically acceptable salt thereof, wherein Z$^1$, Z$^2$, Z$^3$, and Z$^4$ are each CH;

X is N;

Y is O;

R$^1$ is —C$_{0-4}$alkyl-tetrazolyl optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In another embodiment of this one aspect, the compound of this invention is represented by Formula (I) or a pharmaceutically acceptable salt thereof, wherein Z$^1$, Z$^2$, Z$^3$, and Z$^4$ are each CH;

X is N;

Y is O;

R$^1$ is —C$_{0-4}$alkyl-pyrrolidinyl or —C$_{0-4}$alkyl-piperidinyl, optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In another embodiment of this one aspect, the compound of this invention is represented by Formula (I) or a pharmaceutically acceptable salt thereof, wherein Z$^1$, Z$^2$, Z$^3$, and Z$^4$ are each CH;

X is N;

Y is O;

R$^1$ is —C$_{0-4}$alkyl-pyridyl or —C$_{0-4}$alkyl-pyrimidinyl, optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In another embodiment of this one aspect, the compound of this invention is represented by Formula (I) or a pharmaceutically acceptable salt thereof, wherein Z$^1$, Z$^2$, Z$^3$, and Z$^4$ are each CH;

X is N;

Y is O;

R$^1$ is —C$_{0-4}$alkyl-morpholinyl optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In a second aspect of the invention, the compound of this invention is represented by Formula (I) or a pharmaceutically acceptable salt thereof, wherein Z$^1$ is N;

X is N;

Y is O;

R$^1$ is —OH, halogen, or —CN; or a —C$_{1-6}$alkyl, —C$_{1-4}$alkoxyl, -cycloC$_{3-6}$alkyl, —C$_{0-4}$alkyl-phenyl, —C$_{0-4}$alkyl-pyridyl, —C$_{0-4}$alkyl-imidazolyl, —C$_{0-4}$alkyl-pyrazolyl, —C$_{0-4}$alkyl-triazolyl, —C$_{0-4}$alkyl-tetrazolyl, —C$_{0-4}$alkyl-dioxolanyl, —C$_{0-4}$alkyl-thiazolyl, —C$_{0-4}$alkyl-piperidinyl, —C$_{0-4}$alkyl-pyrrolidinyl, —C$_{0-4}$alkyl-morpholinyl, —C$_{0-4}$alkyl-pyrimidinyl, —C$_{2-6}$alkynyl-thiazolyl, or —N(C$_{0-4}$alkyl)(—C$_{0-4}$alkyl) group, wherein any of the groups is optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

In an embodiment of this second aspect, the compound of this invention is represented by Formula (I) or a pharmaceutically acceptable salt thereof, wherein Z$^1$ is N;

X is N;

Y is O;

R$^1$ is —C$_{1-6}$alkyl optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$alkoxyl substituents;

R$^3$ is hydrogen or —C$_{1-4}$alkoxyl;

R$^4$ is —C$_{0-4}$alkyl; and $R^5$ is H, halogen, or —$C_{1-4}$alkyl.

In another embodiment of this second aspect, the compound of this invention is represented by Formula (I) or a pharmaceutically acceptable salt thereof, wherein $Z^1$ is N;

X is N;

Y is O;

$R^1$ is —$C_{0-4}$alkyl-pyridyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In a third aspect, the compound of this invention is represented by Formula (I) or a pharmaceutically acceptable salt thereof, wherein $Z^2$ or $Z^3$ is N;

X is N;

Y is O;

$R^1$ is —OH, halogen, or —CN; or a —$C_{1-6}$alkyl, —$C_{1-4}$alkoxyl, -cyclo$C_{3-6}$alkyl, —$C_{0-4}$alkyl-phenyl, —$C_{0-4}$alkyl-pyridyl, —$C_{0-4}$alkyl-imidazolyl, —$C_{0-4}$alkyl-pyrazolyl, —$C_{0-4}$alkyl-triazolyl, —$C_{0-4}$alkyl-tetrazolyl, —$C_{0-4}$alkyl-dioxolanyl, —$C_{0-4}$alkyl-thiazolyl, —$C_{0-4}$alkyl-piperidinyl, —$C_{0-4}$alkyl-pyrrolidinyl, —$C_{0-4}$alkyl-morpholinyl, —$C_{0-4}$alkyl-pyrimidinyl, —$C_{2-6}$alkynyl-thiazolyl, or —N($C_{0-4}$alkyl)(—$C_{0-4}$alkyl) group, wherein any of the groups is optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; Or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In an embodiment of this third aspect, the compound of this invention is represented by Formula (I) or a pharmaceutically acceptable salt thereof, wherein $Z^2$ or $Z^3$ is N;

X is N;

Y is O;

$R^1$ is —$C_{0-4}$alkyl-pyridyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In a fourth aspect, the compound of this invention is represented by Formula (I) or a pharmaceutically acceptable salt thereof, wherein $Z^1$, $Z^2$, $Z^3$, and $Z^4$ are $CH_2$;

X is N;

Y is O;

$R^1$ is —OH, halogen, or —CN; or a —$C_{1-6}$alkyl, —$C_{1-4}$alkoxyl, -cyclo$C_{3-6}$alkyl, —$C_{0-4}$alkyl-phenyl, —$C_{0-4}$alkyl-pyridyl, —$C_{0-4}$alkyl-imidazolyl, —$C_{0-4}$alkyl-pyrazolyl, —$C_{0-4}$alkyl-triazolyl, —$C_{0-4}$alkyl-tetrazolyl, —$C_{0-4}$alkyl-dioxolanyl, —$C_{0-4}$alkyl-thiazolyl, —$C_{0-4}$alkyl-piperidinyl, —$C_{0-4}$alkyl-pyrrolidinyl, —$C_{0-4}$alkyl-morpholinyl, —$C_{0-4}$alkyl-pyrimidinyl, —$C_{2-6}$alkynyl-thiazolyl, or —N($C_{0-4}$alkyl)(—$C_{0-4}$alkyl) group, wherein any of the groups is optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

In an embodiment of this fourth aspect, the compound of this invention is represented by Formula (I) or a pharmaceutically acceptable salt thereof, wherein $Z^1$, $Z^2$, $Z^3$, and $Z^4$ are $CH_2$;

X is N;

Y is O;

$R^1$ is —$C_{1-6}$alkyl optionally substituted with 1–5 substituents; wherein each substituent is independently halogen, —OH, —CN, —$C_{1-6}$alkyl, —$C_{1-4}$alkoxyl, —N($C_{0-4}$alkyl)($C_{0-4}$alkyl), —$C_{0-4}$alkyl-C(O)—O—$C_{0-4}$alkyl, —$C_{0-4}$alkyl-morpholinyl, or —$C_{0-4}$alkyl-benzoxazolyl;

$R^2$ is halogen, —OH, —CN, —N($C_{0-4}$alkyl)($C_{0-4}$alkyl), —$NO_2$; or —$C_{1-6}$alkyl, —$C_{1-4}$alkoxyl, —$C_{0-4}$alkyl-phenyl, or —$C_{1-4}$alkoxy-phenyl group, wherein any of the groups is optionally substituted with 1–3 independently halogen, —OH, —CN, or —$C_{1-4}$alkoxyl substituents;

$R^3$ is hydrogen or —$C_{1-4}$alkoxyl;

$R^4$ is —$C_{0-4}$alkyl; and $R^5$ is H, halogen, or —$C_{1-4}$alkyl.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, biand tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the allyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiv) norepinephrine modulators, xv) L-DOPA, xvi) buspirone, xvii) lithium, xviii) valproate, xix) neurontin (gabapentin), xx) olanzapine, xxi) nicotinic agonists or antagonists including nicotine, xxii) muscarinic agonists or antagonists, xxiii) heroin substituting drugs such as methadone, levo-alpha-acetylmethadol, buprenorphine and naltrexone, and xxiv) disulfiram and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, and panic, as well as being useful in the treatment of pain which are responsive to mgluR5 inhibition, or alternatively about 0.5 mg to about 7 g per patient per day. For example, schizophrenia, anxiety, depression, and panic may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the mgluR5 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as mgluR5 inhibitors. Accordingly, another aspect of the invention is the treatment in mammals of, for example, schizophrenia, anxiety, depression, and panic, pain, Parkinson's disease, cognitive dysfunction, epilepsy, drug addiction, drug abuse and drug withdrawal—maladies that are amenable to amelioration through inhibition of mGluR5—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the mgluR5 inhibiting compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SS-NRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| cAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| $Et_3N$ | triethylamine |
| GST | glutathione transferase |
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| MsO | methanesulfonate = mesylate |
| NBS | N-bromo succinimide |
| NSAID | non-steroidal anti-inflammatory drug |
| o-Tol | ortho-tolyl |
| OXONE® | $2KHSO_5 \cdot KHSO_4 \cdot K_2SO_4$ |
| PCC | pyridinium chlorochromate |
| $Pd_2(dba)_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| rt | room temperature |
| Rac. | Racemic |
| SAM | aminosulfonyl or sulfonamide or $SO_2NH_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| $C_3H_5$ | Allyl |
| ALKYL GROUP ABBREVIATIONS | |
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | Cyclopropyl |
| c-Bu = | Cyclobutyl |
| c-Pen = | Cyclopentyl |
| c-Hex = | Cyclohexyl |

Assays Demonstrating Biological Activity

The compounds of this invention were tested against the hmGluR5a receptor stably expressed in mouse fibroblast Ltk⁻ cells (the hmGluR5a/L38-20 cell line) and activity was detected by changes in $[Ca^{++}]_i$, measured using the fluorescent $Ca^{++}$-sensitive dye, fura-2. InsP assays were performed in mouse fibroblast Ltk⁻ cells (LM5a cell line) stably expressing hmGluR5a. The assays described in International Patent Publication WO 0116121 can be used.

Calcium Flux Assay

The activity of compounds was examined against the hmGluR5a receptor stably expressed in mouse fibroblast Ltk– cells (the hmGluR5a/L38 cell line). See generally Daggett et al., *Neuropharmacology* 34:871–886 (1995). Receptor activity was detected by changes in intracellular calcium ($[Ca^{2+}]_i$) measured using the fluorescent calcium-sensitive dye, fura-2. The hmGluR5a/L38-20 cells were plated onto 96-well plates, and loaded with 3 µM fura-2 for 1 h. Unincorporated dye was washed from the cells, and the cell plate was transferred to a 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every is, and ratio images were generated after background subtraction. After a basal reading of 20 s, an $EC_{80}$ concentration of glutamate (10 µM) was added to the well, and the response evaluated for another 60 s. The glutamate-evoked increase in $[Ca']_i$ in the presence of the screening compound was compared to the response of glutamate alone (the positive control).

Phosphatidylinositol Hydrolysis (PI) Assays

Inositolphosphate assays were performed as described by Berridge et al. [Berridge et al, *Biochem. J.* 206: 587–5950 (1982); and Nakajima et al., *J. Biol. Chem.* 267:2437–2442 (1992)] with slight modifications. Mouse fibroblast Ltk cells expressing hmGluR5 (hmGluR5/L38-20 cells) were seeded in 24-well plates at a density of 8×10⁵cells/well. One µCi of [³H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 mL of standard Hepes buffered saline buffer (HBS; 125 mM NaCl, 5 mM KCl, 0.62 mMmgSO₄, 1.8 mM CaCl₂, 20 mM HEPES, 6 mM glucose, pH to 7.4). The cells were washed with BBS containing 10 mM LiCl, and 400 µL buffer added to each well. Cells were incubated at 37° C. for 20 min. For testing, 50 µL of 10× compounds used in the practice of the invention (made in HBS/LiCl (100 mM) was added and incubated for 10 minutes. Cells were activated by the addition of 10 µM glutamate, and the plates left for 1 hour at 37° C. The incubations were terminated by the addition of 1 mL ice-cold methanol to each well. In order to isolate inositol phosphates (IPs), the cells were scraped from wells, and placed in numbered glass test tubes. One mL of chloroform was added to each tube, the tubes were mixed, and the phases separated by centrifugation. IPs were separated on Dowex anion exchange columns (AG 1-X8 100–200 mesh formate form). The upper aqueous layer (750 µL) was added to the Dowex columns, and the columns eluted with 3 mL of distilled water. The eluents were discarded, and the columns were washed with 10 mLs of 60 mM ammonium formate/5 mM Borax, which was also discarded as waste. Finally, the columns were eluted with 4 mL of 800 mM ammonium formate/0.1M formic acid, and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with the agonist alone in the absence of compound.

The compounds of this application have mgluR5 inhibitory activity as shown by values of less than 5 µM in the calcium flux assay and values of less than 100 µM in the PI assay. Preferably, the compounds should have values of less than 500 nM in the calcium flux assay and values of less than 10 µM in the PI assay. Even more preferably, the compounds should have values of less than 50 nM in the calcium flux assay and values of less than 1 µM in the PI assay.

Examples 1–80 have mGluR5 inhibitory activity as shown by values of less than 5 µM in the calcium flux assay and values of less than 100 µM in the PI assay.

The examples that follow are intended as an illustration of certain preferred embodiments of the invention and no limitation of the invention is implied.

Unless specifically stated otherwise, the experimental procedures were performed under the following conditions. All operations were carried out at room or rt—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

Scheme 1:
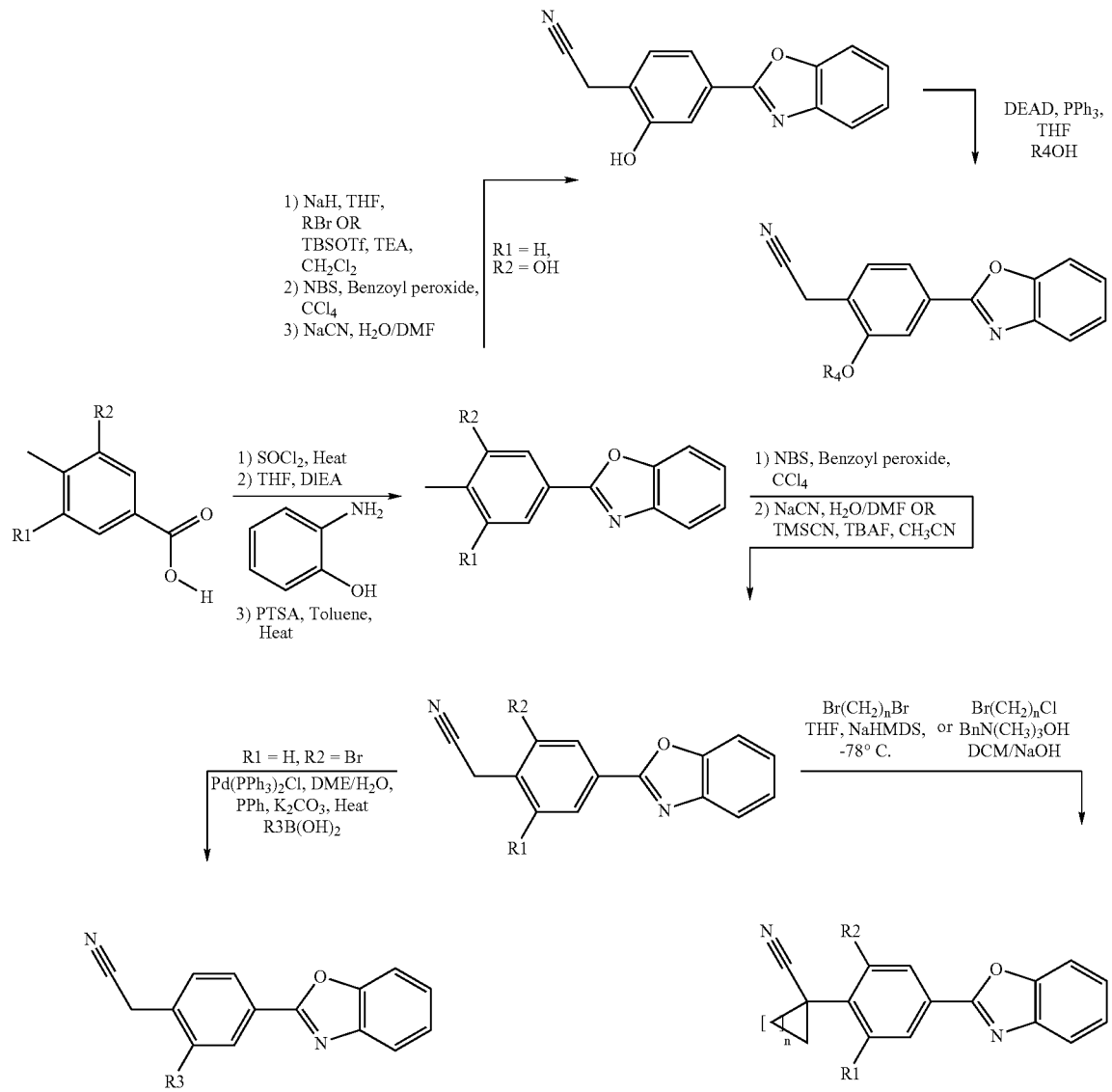
Scheme 2:
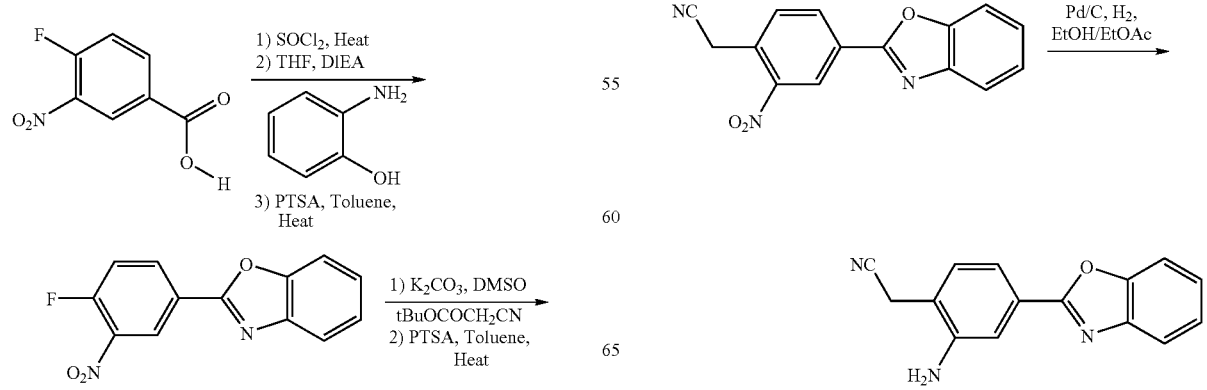

Scheme 3:
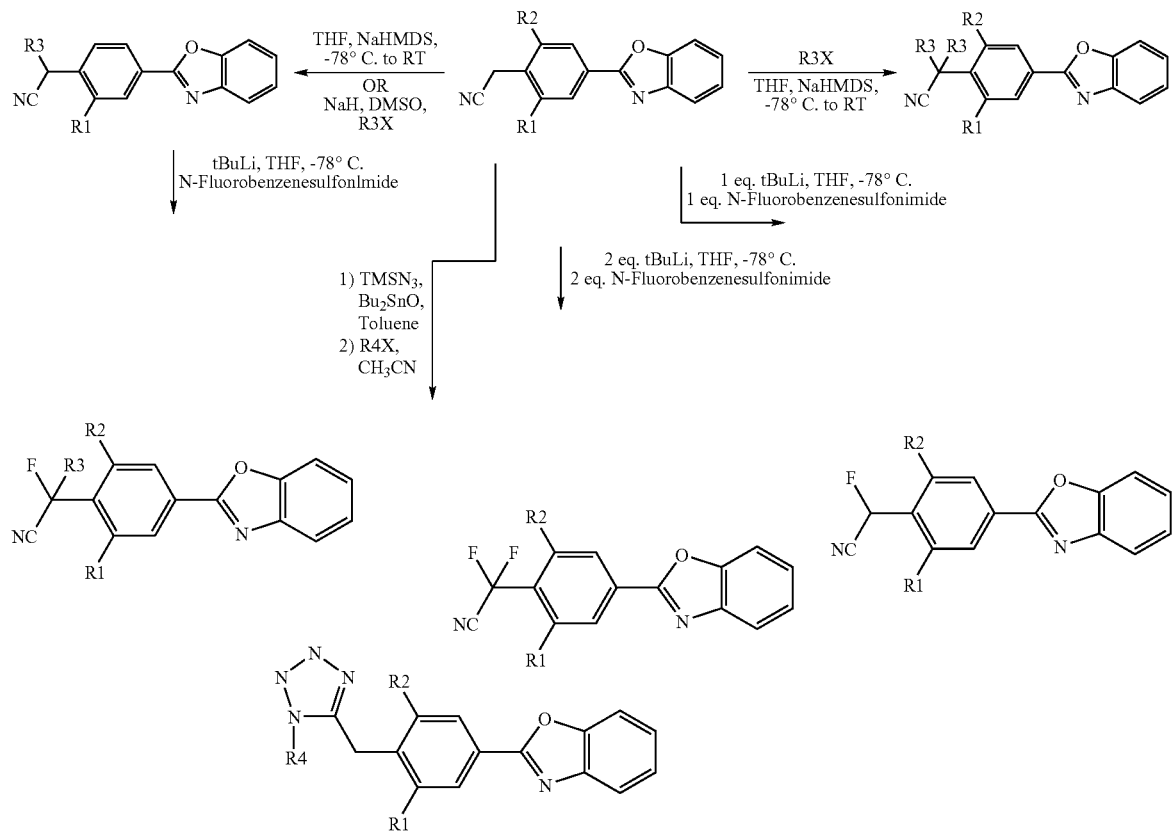
Scheme 4:
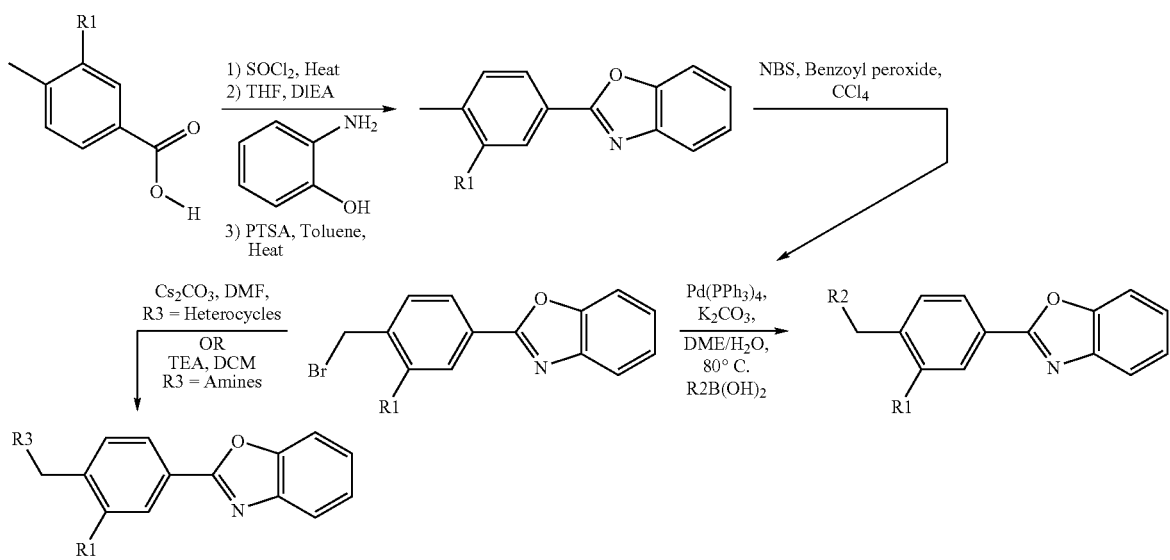

Scheme 5:
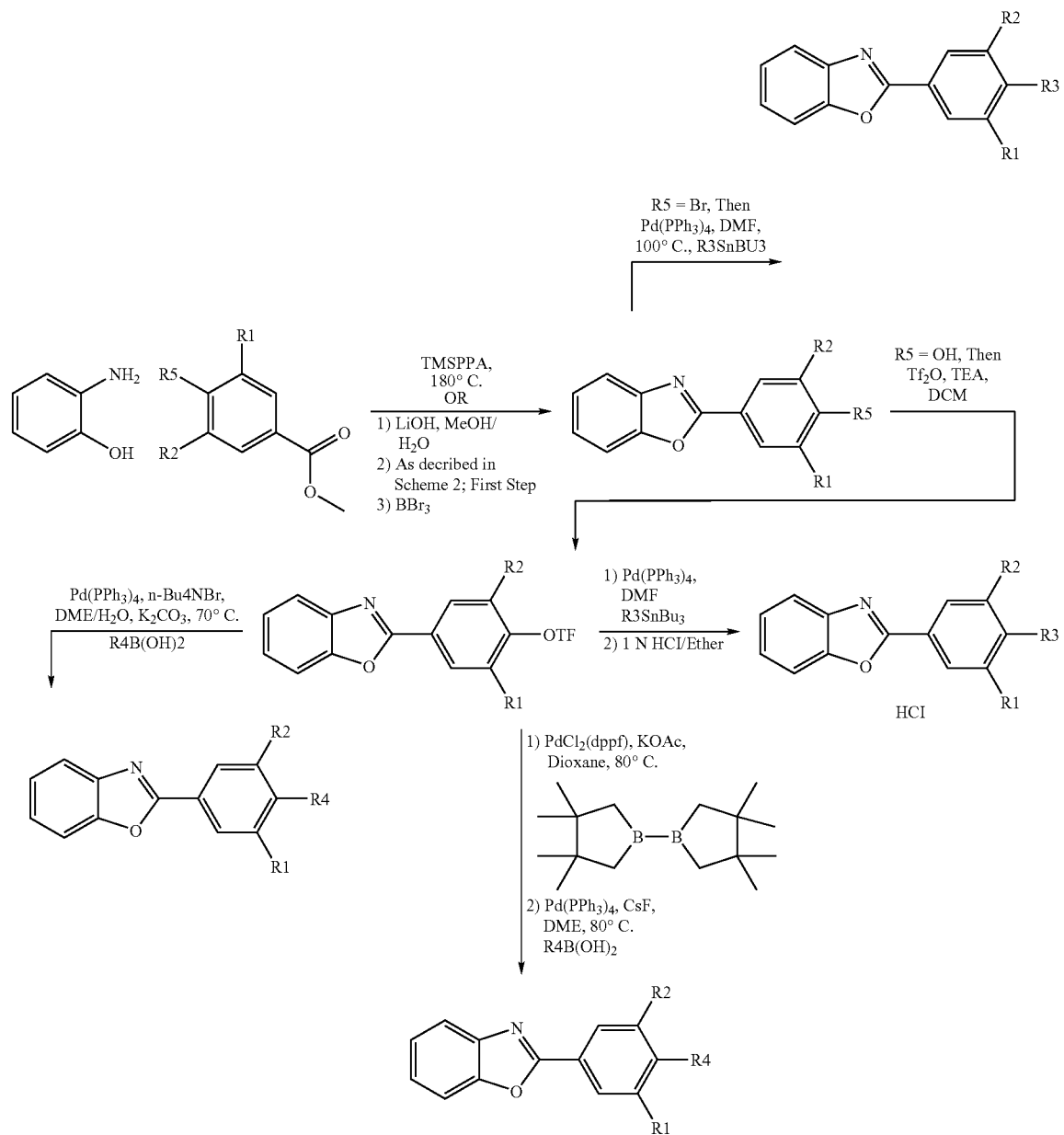
Scheme 6:
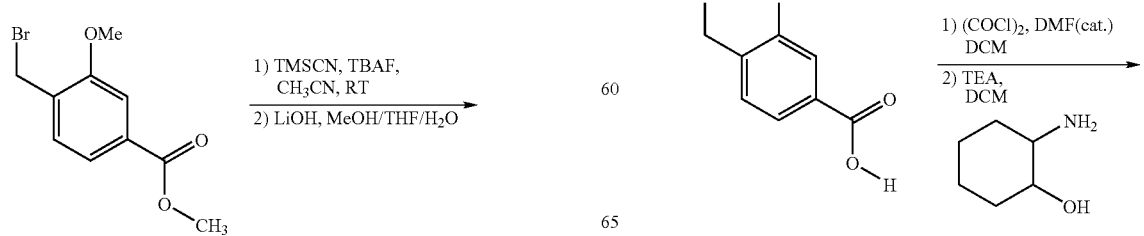

-continued
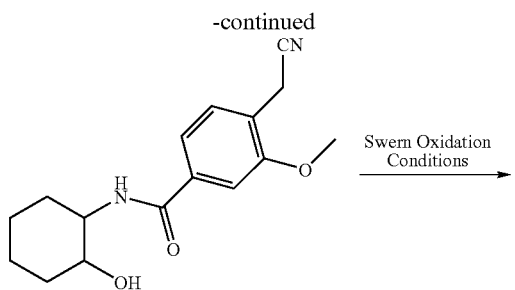
Scheme 8:
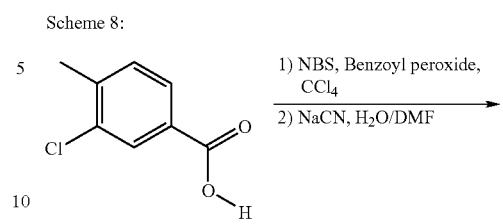
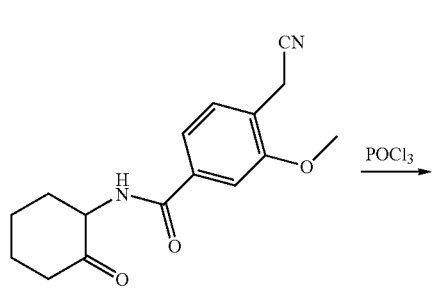
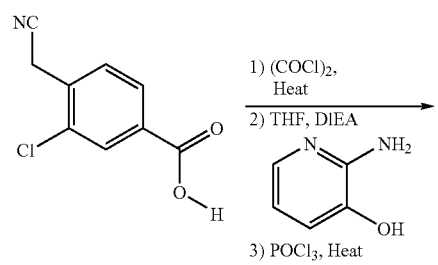
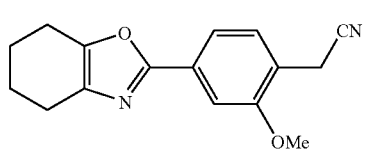
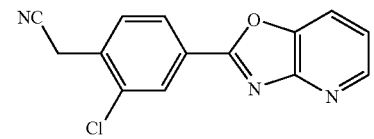
Scheme 7:
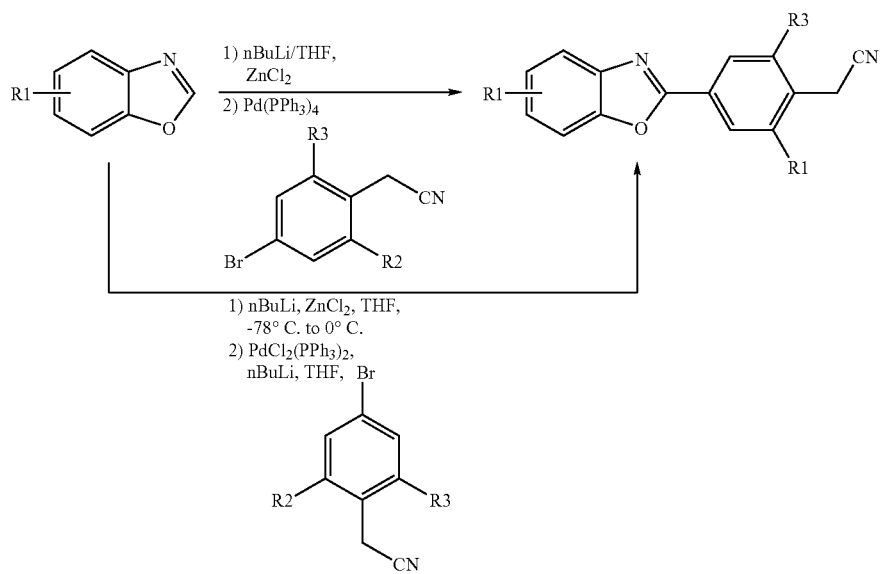

Scheme 9:

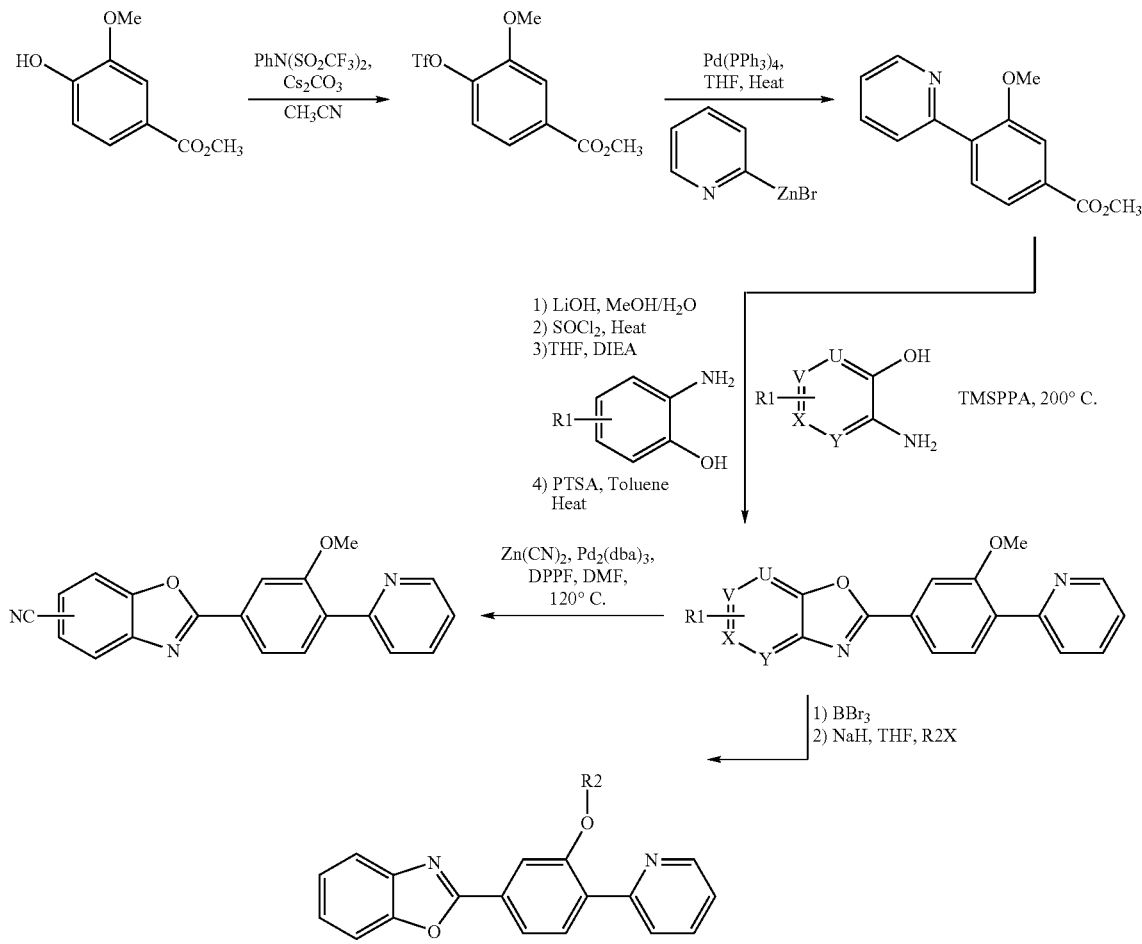

EXAMPLE 1

[4-(1,3-Benzoxazol-2-yl)-2-bromnophenyl]acetonitrile

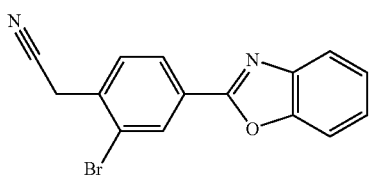

A mixture of 3-bromo-4-methylbenzoic acid (1.0 g, 4.7 mmol) and thionyl chloride (18 mL) was refluxed for 1 h and then cooled to rt. The excess thionyl chloride was removed in vacuo, the residue was dissolved in THF (10 mL), and was added to a cooled (0° C.) mixture of 2-aminophenol (510 mg, 4.7 mmol) and diisopropylethylamine (0.90 mL, 5.1 mmol) in THF (18 mL). The resulting mixture was stirred at rt for 4 h. The solvent was then removed and the residue was purified by flash chromatography on silica gel eluting with EtOAc:hexane (1:5 to 1:4) to afford 3-bromo-N-(2-hydroxyphenyl)-4-methylbenzamide.

A mixture of 3-bromo-N-(2-hydroxyphenyl)-4-methylbenzamide (550 mg, 1.8 mmol), p-toluenesulfonic acid (2.4 g, 12.7 mmol) in toluene (50 mL) was refluxed for 4 h, cooled to rt, and filtered through a Celite pad. The filtrate was evaporated to dryness and the residue was purified by flash chromatography on silica gel using a gradient of EtOAc:hexane (0 to 30 min: 0 to 15% EtOAc) to afford 2-(3-bromo-4-methylphenyl)-1,3-benzoxazole as a colorless solid. MS (ESI) 288 (M+H)$^+$.

A mixture of 2-(3-bromo-4-methylphenyl)-1,3-benzoxazole (240 mg, 0.83 mmol), n-bromosuccinimide (180 mg, 0.99 mmol), and benzoyl peroxide (10 mg, 0.041 mmol) in carbon tetrachloride (15 mL) was refluxed for 3 h. The white precipitate was filtered and the filtrate was evaporated to dryness. The resulting solid was purified by flash chromatography on silica gel eluting with EtOAc:hexane (1:5) to afford 2-[3-bromo-4-(bromomethyl)phenyl]-1,3-benzoxazole as a yellow solid.

A mixture of 2-[3-bromo-4-(bromomethyl)phenyl]-1,3-benzoxazole (156 mg, 0.42 mmol), and sodium cyanide (41 mg, 0.84 mmol) in DMF:H$_2$O (3:1, 16 mL) was stirred at rt for 18 h. Water (50 mL) was added to the reaction mixture and it was extracted with EtOAc (3×). The organics were combined, washed with brine (2×), dried over Na$_2$SO$_4$, and evaporated to dryness to give an orange oil. The crude oil was purified by flash chromatography eluting with a gradient of EtOAc:hexane (0 to 30 min: 0 to 20% EtOAc) to afford the desired [4-(1,3-benzoxazol-2-yl)-2-bromophenyl]acetonitrile as a yellow solid (M.p. 190–191° C.). $^1$H NMR (CDCl$_3$, 300 MHz) δ 8.50 (s, 1H), 8.22 (dd, 1H), 7.78 (m, 1H), 7.70 (d, 1H), 7.60 (m, 1H), 7.39 (m, 2H), 3.91 (s, 2H). MS (ESI) 313 (M)$^+$.

EXAMPLE 2

[5-(1,3-Benzoxazol-2-yl)-2',4'-dimethoxy-1,1'-biphenyl-2-yl]acetonitrile

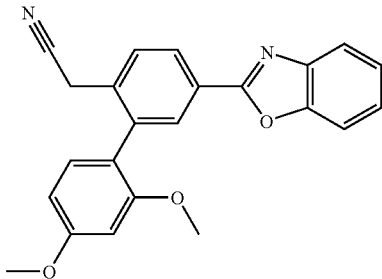

A mixture of 2,4-dimethoxyphenylboronic acid (175 mg, 0.96 mmol), [4-(1,3-benzoxazol-2-yl)-2-bromophenyl]acetonitrile (example 1) (200 mg, 0.64 mmol), dichlorobis(triphenylphosphine)palladium(II) (22 mg, 0.032 mmol), triphenylphosphine (17 mg, 0.064 mmol), and potassium carbonate (177 mg, 1.3 mmol) in degassed DME/H$_2$O (5:1, 12 mL) was heated at 83° C. for 18 h. The mixture was cooled to rt, the two layers were separated and the aqueous layer was extracted with EtOAc (3×). The organics were combined, dried over Na$_2$SO$_4$ and evaporated to dryness to give an orange solid. Purification of the crude by flash chromatography on silica gel eluting with a gradient of EtOAc:hexanes (0 to 40 min: 0 to 20% EtOAc, 40 to 50 min: 50% EtOAc) afforded [5-(1,3-benzoxazol-2-yl)-2',4'-dimethoxy-1,1'-biphenyl-2-yl]acetonitrile as a yellow solid. $^1$H NMR (CDCl$_3$, 300 MHz) δ 8.26 (dd, 1H), 8.15 (s, 1H), 7.77 (m, 1H), 7.70 (d, 1H), 7.57 (m, 1H), 7.36 (m, 2H), 7.16 (d, 1H), 6.62 (dd, 1H), 6.57 (s, 1H), 3.88 (s, 3H), 3.78 (s, 3H), 3.64 (q, 2H). MS (ESI) 371 (M+H)$^+$.

EXAMPLE 3

[4-(1,3-Benzoxazol-2-yl)-2-methylphenyl]acetonitrile

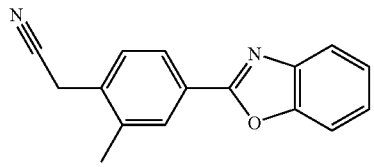

A mixture of methane boronic acid (57.6 mg, 0.96 mmol), [4-(1,3-benzoxazol-2-yl)-2-bromophenyl]acetonitrile (example 1) (200 mg, 0.64 mmol), dichlorobis(triphenylphosphine)palladium(II) (22.4 mg, 0.032 mmol), triphenylphosphine (17 mg, 0.064 mmol), and potassium carbonate (177 mg, 1.3 mmol) in degassed DME/H$_2$O (5:1, 12 mL) was heated at 80° C. for 18 h. The mixture was cooled to rt, the two layers were separated and the aqueous layer was extracted with EtOAc (3×). The organics were combined, dried over Na$_2$SO$_4$ and evaporated to dryness to give a brown solid. Purification of the crude solid by flash chromatography on silica gel eluting with a gradient of EtOAc:hexanes (0 to 40 min: 0 to 25% EtOAc) afforded the desired [4-(1,3-benzoxazol-2-yl)-2-methylphenyl]acetonitrile as a yellow solid. $^1$H NMR (CDCl$_3$, 300 MHz) δ 8.14 (s, 1H), 8.11 (d, 1H), 7.78 (m, 1H), 7.60 (m, 1H), 7.54 (d, 1H), 7.38 (m, 2H), 3.76 (s, 2H), 2.45 (s, 3H). MS (ESI) 249 (M+H)$^+$.

EXAMPLE 4

5'-(1,3-Benzoxazol-2-yl)-2'-(cyanomethyl)-1,1'-biphenyl-3-carbonitrile

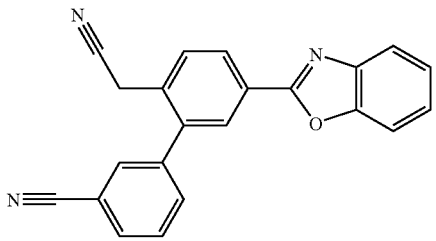

A mixture of 3-bromo-4-methylbenzoic acid (1.0 g, 4.7 mmol) and thionyl chloride (18 mL) was refluxed for 1 h and then cooled to rt. The excess thionyl chloride was removed int vacuo, the residue was dissolved in THF (10 mL), and it was added to a cooled (0° C.) mixture of 2-aminophenol (507 mg, 4.7 mmol) and diisopropylethylamine (0.90 mL; 5.1 mmol) in THF (18 mL). The resulting mixture was stirred at rt for 4 h. The solvent was then removed and the residue was purified by flash chromatography on silica gel eluting with EtOAc:hexanes (1:5 to 1:4) to afford 3-bromo-N-(2-hydroxyphenyl)-4-methylbenzamide.

A mixture of 3-bromo-N-(2-hydroxyphenyl)-4-methylbenzamide (554 mg, 1.8 mmol), p-toluenesulfonic acid (2.41 g, 12.7 mmol) and toluene (50 mL) was refluxed for 4 h, cooled to rt, and filtered through a Celite pad. The filtrate was evaporated to dryness and the residue was purified by flash chromatography on silica gel using a gradient of EtOAc:hexanes (0 to 30 min:0 to 15% EtOAc) to afford 2-(3-bromo-4-methylphenyl)-1,3-benzoxazole as a colorless solid. MS (ESI) 288 (M$^+$).

A mixture of 3-cyano-phenylboronic acid (183 mg, 1.3 mmol), 2-(3-bromo-4-methylphenyl)-1,3-benzoxazole (300 mg, 1.04 mmol), dichlorobis(triphenylphosphine)palladium (II) (36.5 mg, 0.052 mmol), triphenylphosphine (27 mg, 0.104 mmol), and potassium carbonate (287 mg, 2.08 mmol) in degassed DME/H$_2$O (5:1, 18 mL) was heated to 80° C. for 18 h. The mixture was cooled to rt and the two layers were separated and the aqueous layer was extracted with EtOAc (3×). The organics were combined, dried over Na$_2$SO$_4$, and evaporated to dryness to give a clear solid. Purification of the crude by flash chromatography on silica gel eluting with a gradient of EtOAc:hexanes (0 to 30 min: 0 to 20% EtOAc) afforded 5'-(1,3-benzoxazol-2-yl)-2'-methyl-1,1'-biphenyl-3-carbonitrile a colorless solid.

A mixture of 5'-(1,3-benzoxazol-2-yl)-2'-methyl-1,1'-biphenyl-3-carbonitrile (229 mg, 0.74 mmol), n-bromosuccinimide (145 mg, 0.81 mmol), and benzoyl peroxide (9 mg, 0.037 mmol) in carbon tetrachloride (15 mL) was refluxed for 5 h. The solvent was evaporated to dryness and the crude was purified by flash chromatography on silica gel eluting with a gradient of EtOAc:hexanes (0 to 30 min: 0 to 20% EtOAc, 30 to 40 min: 50% EtOAc) to afford 5'-(1,3-benzoxazol-2-yl)-2'-(bromomethyl)-1,1'-biphenyl-3-carbonitrile as a colorless solid.

A mixture of 5'-(1,3-benzoxazol-2-yl)-2'-(bromomethyl)-1,1'-biphenyl-3-carbonitrile (183 mg, 0.47 mmol) and sodium cyanide (46 mg, 0.94 mmol) in DMF:H$_2$O (5:1, 18 mL) and DMF (20 mL) was stirred at rt for 3 h. H$_2$O was added to the reaction mixture and it was extracted with EtOAc (3×). The organics were combined, washed with brine (2×), dried over Na$_2$SO$_4$, and evaporated to dryness to give an orange oil. The crude was purified by flash chromatography on silica gel eluting with a gradient of EtOAc:hexanes (0 to 30 min: 0 to 20% EtOAc) to afford the desired 5'-(1,3-benzoxazol-2-yl)-2'-(cyanomethyl)-1,1'-biphenyl-3-carbonitrile as a colorless solid (M.p. 175–176° C.). $^1$H NMR (CDCl$_3$, 300 MHz) δ 8.34 (dd, 1H), 8.18 (s, 1H), 7.77 (m, 3H), 7.67 (m, 3H), 7.60 (m, 1H), 7.40 (m, 2H), 3.69 (s, 2H). MS (ESI) 336 (M+H)$^+$.

EXAMPLE 5

[4-(1,3-Benzoxazol-2-yl)-2-(trifluoromethyl)phenyl]acetonitrile

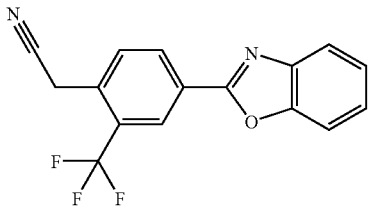

A mixture of 4-methyl-3-(trifluoromethyl)benzoic acid (1.0 g, 4.9 mmol) and thionyl chloride (15 mL) was refluxed for 3 h and then stirred at rt overnight. The excess thionyl chloride was removed in vacuo, the residue was dissolved in THF (20 mL), and it was added to a cooled (0° C.) solution of 2-aminophenol (0.53 g, 4.9 mmol) and diisopropylethylamine (1.0 mL, 5.9 mmol) in anhydrous THF (15 mL). The resulting brownish mixture was stirred at rt for 3 h. The solvent was then removed and p-toluenesulfonic acid (3.7 g, 19.6 mmol) and toluene (20 mL) were added to the dark oil. The mixture was then refluxed for 3 h and the mixture was cooled to rt. The excess p-toluenesulfonic acid was filtered through Celite and the filtrate was evaporated to dryness. The crude was purified by flash chromatography on silica gel eluting with EtOAc:hexanes (1:9) to afford 2-[4-methyl-3-(trifluoromethyl)phenyl]-1,3-benzoxazole as a colorless solid.

A mixture of 2-[4-methyl-3-(trifluoromethyl)phenyl]-1,3-benzoxazole (600 mg, 2.2 mmol), n-bromosuccinimide (579 mg, 3.25 mmol), benzoyl peroxide (26 mg, 0.11 mmol) in carbon tetrachloride (15 mL) was refluxed for 3 h and then cooled to rt. The white precipitate was filtered and the filtrate was concentrated to dryness. The crude was purified by flash chromatography on silica gel eluting with EtOAc:hexanes (1:1) to afford 2-[4-(bromomethyl)-3-(trifluoromethyl)phenyl]-1,3-benzoxazole.

To a suspension of 2-[4-(bromomethyl)-3-(trifluoromethyl)phenyl]-1,3-benzoxazole (528 mg, 1.5 mmol) and cyanotrimethylsilane (0.30 mL, 2.2 mmol) in acetonitrile (19 mL) was added TBAF (1.0M in THF, 2.2 mL, 2.2 mmol) and the mixture was stirred at rt for 2 h. The solvent was removed in vacuo and the crude was purified by flash chromatography eluting with EtOAc:hexanes (1:9) to afford the desired [4-(1,3-benzoxazol-2-yl)-2-(trifluoromethyl)phenyl]acetonitrile as a colorless solid. $^1$H NMR (CDCl$_3$, 300 MHz) δ 8.60 (s, 1H), 8.48 (d, 1H), 7.88 (d, 1H), 7.82 (m, 1H), 7.63 (m, 1H), 7.43 (m, 2H), 4.05 (s, 2H). MS (ESI) 303 (M+H)$^+$.

EXAMPLE 6

[4-(1,3-Benzoxazol-2-yl)-2-nitrophenyl]acetonitrile

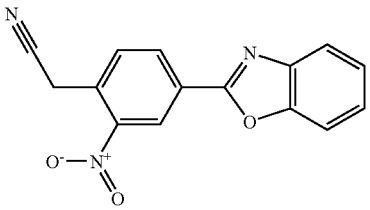

A mixture of 4-fluoro-3-nitrobenzoic acid (2.1 g, 11.3 mmol) and thionyl chloride (20 mL) was refluxed for 3 h and then cooled to rt. The excess thionyl chloride was removed and the residue dissolved in 10 mL of THF was added to a cooled (0° C.) solution of 2-aminophenol (1.24 g, 11.3 mmol) and diisopropylethylamine (2.4 mL, 13.6 mmol) in anhydrous THF (20 mL). The resulting mixture was refluxed for 4 h and then cooled to rt. The solvent was removed and p-toluenesulfonic acid (8.63 g, 45.4 mmol) and toluene (50 mL) were added to afford a dark mixture that was refluxed overnight. The solvent was removed and the crude was purified by flash chromatography on silica gel eluting with hexanes:CH$_2$Cl$_2$ (1:5) to afford 2-(4-fluoro-3-nitrophenyl)-1,3-benzoxazole as a colorless solid.

2-(4-fluoro-3-nitrophenyl)-1,3-benzoxazole (200 mg, 0.77 mmol) was dissolved in DMSO (5 mL) and K$_2$CO$_3$ (267 mg, 1.94 mmol) was added. The resulting yellow mixture was warmed to 65° C. and tert-butylcyanoacetate (137 mg, 0.97 mmol) was added dropwise. The dark red mixture was heated to 65° C. for 30 min, cooled to rt, and poured into H$_2$O. The aqueous layer was acidified to pH 3 (with a 10% aqueous HCl solution) and it was extracted with EtOAc (3×). The organics were combined, washed with brine (2×), dried over Na$_2$SO$_4$, and evaporated to dryness. The yellow residue and p-toluenesulfonic acid (29.5 mg, 0.15 mmol) were dissolved in toluene (15 mL) and the mixture was refluxed for 20 h. After cooling to rt, the mixture was poured in H$_2$O and the two layers were separated. The aqueous was extracted with EtOAc (3×), the organics were combined, dried over Na$_2$SO$_4$, and evaporated to dryness. Purification of the residue by flash chromatography on silica gel eluting with EtOAc:hexanes (3:7 to 2:3 to 1:1) afforded the desired [4-(1,3-benzoxazol-2-yl)-2-nitrophenyl]acetonitrile as an orange solid (M.p. 203° C.). $^1$H NMR (CDCl$_3$, 300 MHz) δ 8.79 (s, 1H), 8.57 (dd, 1H), 7.97 (d, 1H), 7.86 (m, 2H), 7.54–7.44 (m, 2H), 4.50 (s, 2H). MS (ESI) 280 (M+H)$^+$.

EXAMPLE 7

[2-Amino-4-(1,3-benzoxazol-2-yl)phenyl]acetonitrile

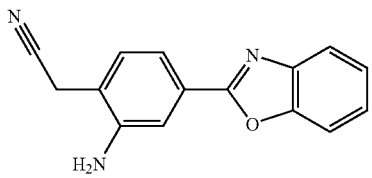

A suspension of [4-(1,3-benzoxazol-2-yl)-2-nitrophenyl]acetonitrile (100 mg, 0.36 mmol) and Pd/C (20 mg) in EtOH/EtOAc (5:1, 60 mL) was hydrogenated (35 psi) over 2d. The resulting reaction mixture was filtered through Celite and the filtrate was evaporated to dryness. The yellow solid obtained was purified by flash chromatography on silica gel eluting with MeOH:CH$_2$Cl$_2$ (1:19) to afford [2-amino-4-(1,3-benzoxazol-2-yl)phenyl]acetonitrile as an orange solid (M.p. 198–199° C.). $^1$H NMR (CDCl$_3$, 300 MHz) δ 7.77 (m, 1H), 7.71–7.66 (m, 2H), 7.58 (m, 1H), 7.40–7.34 (m, 3H), 3.88 (s, 2H), 3.66 (s, 2H). MS (ESI) 250 (M+H)$^+$.

EXAMPLE 8

[4-(1,3-Benzoxazol-2-yl)-2-fluorophenyl]acetonitrile

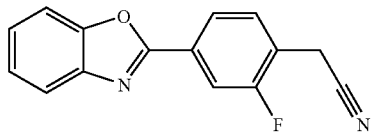

To a stirred solution of 4-bromo-2-fluoro benzyl bromide (1.5 g, 5.6 mmol) in DMF (50 mL) was added sodium cyanide (0.8 g, 17 mmol). The reaction mixture was stirred at 90° C. for 1 h, cooled to rt and quenched with brine (50 mL). After extraction with EtOAc (3×100 mL), the organic layers were combined, washed with brine (50 mL), dried (MgSO$_4$), filtered and concentrated in vacuo. The residue was purified by flash chromatography (silica gel, hexanes:EtOAc 5:1) to afford 4-bromo-2-fluoro benzyl cyanide as yellow solid. MS (ESI) 307 (M+H)$^+$.

To a stirred solution of benzoxazole (153 mg, 1.3 mmol) in 5 mL THF at −78° C., was added n-Butyllithium (640 μL, 2.5M in hexanes, 1.6 mmol). The reaction mixture was stirred for 15 min at −78° C. and ZnCl$_2$ (3.9 mL, 1.0M solution in Et$_2$O, 3.9 mmol) was added via a syringe. The reaction was then warmed to 0° C. for 1 h and a solution of 4-bromo-2-fluoro benzyl cyanide (214 mg, 1.0 mmol) in THF (2 mL) was added, along with Pd (a fine suspension prepared as follows: 200 μL n-Butyllithium, 2.5M in hexanes added to 144 mg PdCl$_2$(PPh$_3$)$_2$ in 5 mL of THF). The reaction mixture was then stirred at reflux overnight, quenched with sat. NaHCO$_3$ (50 mL) and diluted with EtOAc (300 mL). The resulting organic layer was washed with H$_2$O (1×50 mL), dried (MgSO$_4$) and concentrated in vacuo. The residue purified by flash chromatography (silica gel, hexanes:EtOAc 5:1) to afford the desired [4-(1,3-benzoxazol-2-yl)-2-fluorophenyl]acetonitrile as a yellow solid. $^1$H NMR (CD$_3$OD, 300 MHz) δ 8.14 (q, 1H), 8.2 (q, 1H), 7.82 (m, 1H), 7.63 (m, 2H), 7.42 (m, 2H), 3.85 (s, 2H). MS (ESI) 253 (M+H)$^+$.

EXAMPLE 9

[2-Fluoro-4-(6-methyl-1,3-benzoxazol-2-yl)phenyl]acetonitrile

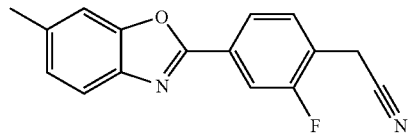

To a stirred solution of 4-bromo-2-fluoro benzyl bromide (1.5 g, 5.6 mmol) in DMF (50 mL) was added sodium cyanide (0.8 g, 16.8 mmol). The reulting reaction mixture was stirred at 90° C. for 1 h, cooled to rt, quenched with brine (50 mL) and extracted with EtOAc (3×100 mL). The organic layers were combined, washed with brine (50 mL), dried (MgSO$_4$) and concentrated in vacuo. The residue was purified by flash column (silica gel, hexanes:EtOAc 5:1) to afford 4-bromo-2-fluoro benzyl cyanide as yellow solid. MS (ESI) 307 (M+H)$^+$.

To a stirred solution of 6-methylbenzoxazole (173 mg, 1.3 mmol) in THF (5 mL) at −78° C., was added n-Butyllithium (640 μL, 2.5M in hexanes, 1.6 mmol). The resulting reaction mixture was stirred for 15 min at −78° C. and ZnCl$_2$ (3.9 mL, 1M in Et$_2$O, 3.9 mmol) was added via a syringe. After warming up the reaction mixture at 0° C. for 1 h, a solution of 4-bromo-2-fluoro benzyl cyanide (214 mg, 1.0 mmol) in THF (2 mL) was added, along with Pd$^0$ (a fresh suspension prepared as follows: 200 μL n-Butyllithium, 2.5M in hexanes added to 144 mg of PdCl$_2$(PPh$_3$)$_2$ in 5 mL of THF). The mixture was then heated under reflux overnight. The mixture was hydrolized with sat. NaHCO$_3$ (50 mL) and extracted with EtOAc (3×150 mL). The organic layers were combined, washed with H$_2$O (50 mL), dried (MgSO$_4$) and concentrated in vacuo. The residue was purified by chromatography on silica gel using a mixture of hexanes:EtOAc (5:1) as eluant to afford [2-fluoro-4-(6-methyl-1,3-benzoxazol-2-yl)phenyl]acetonitrile as yellow solid. $^1$H NMR (CD$_3$OD, 300 MHz), δ8.07 (d, 1H), 7.95(d, 1H), 7.64(m, 2H), 7.40(s, 1H), 7.20(d, 11H), 3.90(s, 1H). MS (ESI) 267 (M+H)$^+$.

EXAMPLE 10

[2-Fluoro-4-(5-methyl-1,3-benzoxazol-2-yl)phenyl]acetonitrile

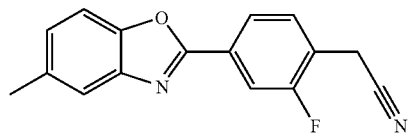

To a stirred solution of 4-bromo-2-fluoro benzyl bromide (1.5 g, 5.6 mmol) in DMF (50 mL) was added sodium cyanide (0.8 g, 16.8 mmol). The resulting mixture was stirred at 90° C. for 1 h, cooled at rt and quenched with brine (50 mL). After extraction with EtOAc (3×50 mL), the organic layers were combined, washed with brine (50 mL), dried (MgSO$_4$), and concentrated in vacuo. The residue was purified by chromatography on silica gel using a mixture of hexanes:EtOAc (5:1) to afford 4-bromo-2-fluoro benzyl cyanide as yellow solid. MS (ESI) 307 (M+H)$^+$.

To a stirred solution of 5-methylbenzoxazole (173 mg, 1.3 mmol) in THP (5 mL) at −78° C. was added n-Butyllithium (640 μL, 2.5M in hexanes, 1.6 mmol). The reaction mixture was stirred for 15 min at −78° C. followed by the addition of ZnCl$_2$ (3.9 mL, 1M in Et$_2$O, 3.9 mmol) via a syringe. The reaction mixture was warmed at 0° C. for 1 h and a solution of 4-bromo-2-fluoro benzyl cyanide (214 mg, 1.0 mmol) in THF (2 mL) was added, along with Pd$^0$ (a fresh suspension prepared as follows: 200 μL n-Butyllithium, 2.5M in hexanes added to 144 mg PdCl$_2$(PPh$_3$)$_2$ in 5 mL of THF). The mixture was refluxed overnight and quenched with sat. NaHCO$_3$ (50 mL). After extraction with EtOAc (3×75 mL), the organic layers were combined, washed with brine (50 mL), dried (MgSO$_4$), and concentrated in vacuo. The residue was purified by chromatography on silica gel using a mixture of hexanes:EtOAc (5:1) to afford the desired [2-fluoro-4-(5-methyl-1,3-benzoxazol-2-yl)phenyl]acetonitrile as yellow solid. $^1$H NMR (CD$_3$OD, 300 MHz), δ 8.07 (d, 1H), 7.95 (d, 1H), 7.64 (m, 2H), 7.40 (s, 1H), 7.20 (d, 1H), 3.90 (s, 1H). MS (ESI) 267 (M+H)$^+$.

EXAMPLE 11

[4-(5-Chloro-1,3-benzoxazol-2-yl)-2-fluorophenyl] acetonitrile

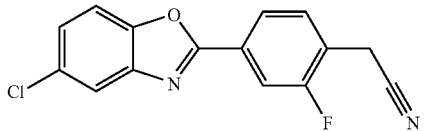

To a stirred solution of 4-bromo-2-fluoro benzyl bromide (1.5 g, 5.6 mmol) in DMF (50 mL) was added sodium cyanide (0.8 g, 16.8 mmol). The reaction was stirred at 90° C. for 1 h, and cooled at rt. After quenching with brine (50 mL) and diluted with EtOAc (100 mL), the EtOAc layer was washed with brine (50 mL), dried (MgSO$_4$), filtered and concentrated in vacuo. The residue was purified by flash chromatography (silica gel, hexanes:EtOAc 5:1) to afford 4-bromo-2-fluoro benzyl cyanide as yellow solid. MS (ESI) 307 (M+H)$^+$.

To a stirred solution of 5-chlorobenzoxazole (200 mg, 1.3 mmol) in 5 mL THF at −78° C., was added n-Butyllithium (640 μL, 2.5M in hexane, 1.6 mmol). The reaction was stirred for 15 min at −78° C. followed by the addition of ZnCl$_2$ (3.9 mL, 1M in Et$_2$O, 3.9 mmol) via a syringe. The reaction was then warmed at 0° C. for 1 h. A solution of 4-bromo-2-fluoro benzyl cyanide (214 mg, 1.0 mmol) in THF (2 mL) was added, along with Pd$^0$ (a fresh suspension prepared as follows: 200 μL, n-Butyllithium, 2.5M in hexanes added to 144 mg of PdCl$_2$(PPh$_3$)$_2$ in 5 mL of THF). The reaction was then stirred at reflux overnight and quenched with sat. NaHCO$_3$ (50 mL). After diluting the mixture with EtOAc (300 mL), the organic extract was washed with H$_2$O (50 mL), dried (MgSO$_4$), filtered and concentrated in vacuo. The residue was purified by flash chromatography (silica gel, hexanes:EtOAc 5:1) to afford the desired [4-(5-chloro-1,3-benzoxazol-2-yl)-2-fluorophenyl]acetonitrile as yellow solid. $^1$H NMR (CD$_3$OD, 300 Hz), δ8.10(d, 1H), 7.99 (d, 1H), 7.79 (d, 1H), 7.68 (t, 1H), 7.52 (d, 1H), 7.39 (q, 1H), 3.90 (s, 1H). MS (ESI) 287 (M+H)$^+$.

EXAMPLE 12

[4-(1,3-Benzoxazol-2-yl)-2-hydroxyphenyl]acetonitrile

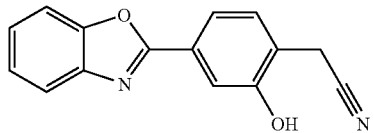

To a 100 mL round-bottom flask with 3-hydroxy-4-methylbenzoic acid (2.5 g, 16.4 mmol), was added dropwise SOCl$_2$ (15 mL). The reaction was refluxed for 30 min and cooled to rt. The excess of SOCl$_2$ was removed in vacuo and the oily acid chloride was dissolved in THF (15 mL). This resulting solution was added dropwise to a mixture of 2-aminophenol (1.8 g, 16.4 mmol), triethylamine (1.7 g, 16.4 mmol) and THF (30 mL) at 0° C. The resulting reaction mixture was then brought to rt for 30 min and the resulting precipitate was removed by filtration. The filtrate was concentrated and dried under vacuum. The resulting dark brown solid residue was dissolved in toluene (20 mL) and p-toluenesulfonic acid (15.6 g, 82 mmol) was added. The reaction was refluxed overnight, cooled at rt and EtOAc (500 mL) was added. The EtOAc solution was washed with brine (3×50 mL), dried (MgSO$_4$), filtered and concentrated in vacuo. The residue was recrystallized in EtOAc to afford 5-(1,3-benzoxazol-2-yl)-2-methylphenol as a light yellow solid. MS (ESI) 226 (M+H)$^+$.

The solution of 5-(1,3-benzoxazol-2-yl)-2-methylphenol (0.8 g, 3.5 mmol) and triethylamine (0.6 mL, 4.3 mmol) in CH$_2$Cl$_2$ (20 mL) was cooled at 0° C. and tert-butyl (900 mL, 3.9 mmol) was added. The reaction was then warmed to rt for 30 min. The mixture was diluted with EtOAc (200 mL), washed with H$_2$O (3×50 mL), dried (MgSO$_4$), filtered, and concentrated in vacuo to afford 2-(3-{[tert-butyl-(dimethyl)silyl]oxy}-4-methylphenyl)-1,3-benzoxazole as light yellow oil.

To 2-(3-{[tert-butyl-(dimethyl)silyl]oxy}-4-methylphenyl)-1,3-benzoxazole (1.46 g, 4.3 mmol) dissolved in CCl$_4$ (50 mL) was added NBS (770 mg, 4.3 mmol) and benzoyl peroxide (50 mg). The reaction mixture was refluxed for 6 h and then cooled to rt. The solvent was removed in vacuo and the residue was diluted with EtOAc (50 mL), washed with brine (50 mL), dried (MgSO$_4$), filtered, and concentrated in vacuo to afford 2-(3-{[tert-butyl-(dimethysilyl]oxy}-4-bromomethylphenyl)-1,3-benzoxazole as light yellow solid.

The mixture of 2-(3-{[tert-butyl-(dimethyl)silyl]oxy}-4-bromomethylphenyl)-1,3-benzoxazole (1.6 g, 3.8 mmol) and sodium cyanide (560 mg, 11.4 mmol) in DMF (10 mL) was stirred at 90° C. overnight. After cooling to rt, the mixture was diluted with EtOAc (100 mL), washed with H$_2$O (2×50 mL), dried (MgSO$_4$), filtered, and concentrated in vacuo to afford the desired [4-(1,3-benzoxazol-2-yl)-2-hydroxyphenyl]acetonitrile as yellow solid. $^1$H NMR (CD$_3$OD, 300 MHz), δ10.6(s, 1H), 7.8(m, 2H), 7.7(m, 2H), 7.5(d, 1H), 7.4(m, 2H). MS (ESI) 251 (M+H)$^+$.

EXAMPLE 13

{4-(1,3-Benzoxazol-2-yl)-2-[2-(4-fluorophenyl)ethoxy]phenyl}acetonitrile

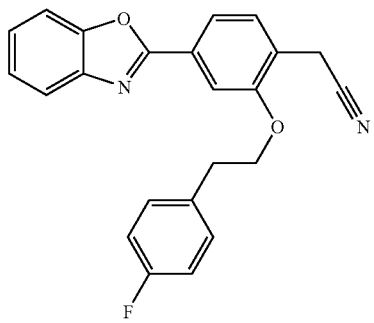

To a 100 mL round-bottom flask with 3-hydroxy-4-methylbenzoic acid (2.5 g, 16.4 mmol), was added $SOCl_2$ (15 mL) dropwise. The reaction was refluxed for 30 min, cooled to rt and the excess of $SOCl_2$ was removed in vacuo. The oily acid chloride was dissolved in THF (15 mL) and the solution was added dropwise to a mixture of 2-aminophenol (1.8 g, 16.4 mmol), triethylamine (1.7 g, 16.4 mmol) and THF (30 mL) at 0° C. The reaction was then warmed to rt for 1 h and the precipitate was removed by filtration. The filtrate was concentrated and dried in vacuo and the dark brown solid residue was dissolved in toluene (20 mL) and p-toluenesulfonic acid (15.6 g, 82 mmol) was added. The reaction was refluxed overnight, cooled to rt and dissolved in EtOAc (500 mL). The organic solution was washed with brine (3×50 mL), dried ($MgSO_4$), filtered, and concentrated in vacuo. The residue was recrystallized in EtOAc to afford 5-(1,3-benzoxazol-2-yl)-2-methylphenol as a light yellow solid. MS (ESI) 226 (M+H)$^+$.

A solution of 5-(1,3-benzoxazol-2-yl)-2-methylphenol (0.8 g, 3.5 mmol) and triethylamine (0.6 mL, 4.3 mmol) in $CH_2Cl_2$ (20 mL) was cooled to 0° C. and TBDMS-OTf (900 mL, 3.9 mmol) was added. The reaction was slowly warmed to rt and EtOAc (200 mL) was added. The mixture was washed with $H_2O$ (3×50 mL), dried ($MgSO_4$), filtered, and concentrated in vacuo to afford 2-(3-{[tert-butyl-(dimethyl)silyl]oxy}-4-methylphenyl)-1,3-benzoxazole as light yellow oil.

To 2-(3-{[tert-butyl-(dimethyl)silyl]oxy}-4-methylphenyl)-1,3-benzoxazole (1.46 g, 4.3 mmol) in $CCl_4$ (50 mL) was added NBS (770 mg, 4.3 mmol) and benzoyl peroxide (50 mg). The reaction mixture was refluxed for 6 h, cooled to rt, and $CCl_4$ was removed in vacuo. The residue was dissolved in EtOAc (50 mL), washed with $H_2O$ (50 mL), dried ($MgSO_4$), filtered and concentrated in vacuo to afford 2-(3-{[tert-butyl-(dimethyl)silyl]oxy}-4-bromomethylphenyl)-1,3-benzoxazole as light yellow solid.

A mixture of 2-(3-{[tert-butyl-(dimethyl)silyl]oxy}-4-bromomethylphenyl)-1,3-benzoxazole (1.6 g, 3.8 mmol) and sodium cyanide (560 mg, 11.4 mmol) in DMF (10 mL) was stirred at 90° C. overnight. The reaction was cooled to rt and dissolved in EtOAc (200 mL), washed with $H_2O$ (2×50 mL), dried ($MgSO_4$), filtered, and concentrated in vacuo to afford [4-(1,3-benzoxazol-2-yl)-2-hydroxyphenyl]acetonitrile as yellow solid. MS (ESI) 251 (M+H)$^+$.

A solution of triphenylphosphine (126 mg, 0.48 mmol), DEAD (84 mg, 0.48 mmol) and THF (2 mL) was stirred 2 h and a solution of [4-(1,3-benzoxazol-2-yl)-2-hydroxyphenyl], acetonitrile (100 mg, 0.4 mmol) and 4-fluorophenethylalcohol (56 mg, 0.4 mmol) in THF (2 mL) was added. The resulting reaction mixture was stirred overnight and the THF was removed in vacuo. The resulting residue was purified on Prep TLC (1000 μm) to afford {4-(1,3-benzoxazol-2-yl)-2-[2-(4-fluorophenyl)ethoxy]phenyl}acetonitrile. $^1$H NMR ($CD_3OD$, 300 MHz), δ 7.88 (d 1H), 7.78 (m, 2H), 7.60 (m, 1H), 7.52 (d, 1H), 7.40 (d, 2H), 7.30 (m, 2H), 7.05 (m, 1H), 4.40 (m, 2H), 3.70 (s, 2H), 3.20 (m, 2H). MS (ESI) 373 (M+H)$^+$.

EXAMPLE 14

[4-(1,3-Benzoxazol-2-yl)-2-ethoxyphenyl]acetonitrile

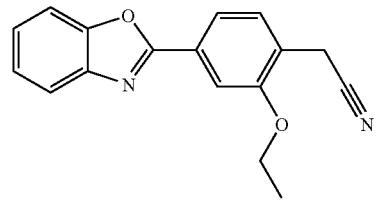

EXAMPLE 15

[4-(1,3-Benzoxazol-2-yl)-2-(methoxymethoxy)phenyl]acetonitrile

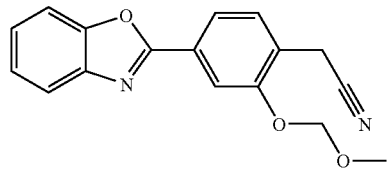

To a 10 mL round-bottom flask with 3-hydroxy-4-methylbenzoic acid (2.5 g, 16.4 mmol), was added $SOCl_2$ (15 mL) dropwise. The reaction was refluxed for 30 min, cooled to rt. The excess of $SOCl_2$ was removed in vacuo and the oily acid chloride was dissolved in THF (15 mL). The resulting solution was added dropwise to a mixture of 2-aminophenol (1.8 g, 16.4 mmol), triethylamine (1.7 g, 16.4 mmol) and THF (30 mL) at 0° C. The reaction mixture was brought to rt for 30 min, after which time, the precipitate was filtered. The filtrate was concentrated and dried in vacuo. The dark brown solid residue was dissolved in toluene (20 mL) and p-toluenesulfonic acid (15.6 g, 82 mmol) was added. The mixture was refluxed overnight, cooled to rt and EtOAc (500 mL) was added. The EtOAc solution was washed with brine (3×50 mL), dried ($MgSO_4$), filtered, and concentrated in vacuo. The residue was recrystallized in EtOAc to afford 5-(1,3-benzoxazol-2-yl)-2-methylphenol as a light yellow solid. MS (ESI) 226(M+H)$^+$.

A solution of 5-(1,3-benzoxazol-2-yl)-2-methylphenol (200 mg, 0.89 mmol) in THF (6 mL) was cooled to −78° C. under Argon and sodium hydride (24 mg, 1.0 mmol) was added. After 30 min at this temperature, bromomethyl ether (225 mg, 1.8 mmol) was added via syringe. The reaction was warmed to rt for 1 h. The reaction mixture was concentrated and the residue was purified by flash column (silica gel, hexanes:EtOAc 4:1) to afford 2-[3-(methoxymethoxy)-4-methylphenyl]-1,3-benzoxazole. MS (ESI) 270 (M+H)+.

A solution of 2-[3-(methoxymethoxy)-4-methylphenyl]-1,3-benzoxazole (200 mg, 0.74 mmol, 84%), NBS (179 mg, 0.81 mmol), and benzoyl peroxide (50 mg) in $CCl_4$ (10 mL), was refluxed for 12 h. After cooling to rt, $CCl_4$ was removed in vacuo and residue was purified by flash column (silica gel, hexanes:EtOAc 5:1) to afford 2-[4-(bromomethyl)-3-(methoxymethoxy)phenyl]-1,3-benzoxazole. MS (ESI) 349 (M+H)+.

2-[4-(Bromomethyl)-3-(methoxymethoxy)phenyl]-1,3-benzoxazole (250 mg, 0.72 mmol) was treated with sodium cyanide (150 mg, 2.2 mmol) in $DMF/H_2O$ (15 mL/1.5 mL) at 90° C. for 3 h and EtOAc (150 mL) was added. The EtOAc solution was washed with $H_2O$ (2×20 mL), brine (2×20 mL), dried ($MgSO_4$), filtered, and concentrated in vacuo. The residue was eluted with flash column (silica gel, hexanes:EtOAc 4:1) to afford the desired [4-(1,3-benzoxazol-2-yl)-2-(methoxymethoxy)phenyl]acetonitrile as a yellow solid. $^1$H NMR ($CD_3OD$, 300 MHz), δ 8.02 (d, 2H), 7.95 (m, 1H), 7.80 (m, 1H), 7.63 (m, 1H), 7.57 (d, 2H), 7.40 (m, 2H). MS (ESI) 295 (M+H)+.

EXAMPLE 16

[4-(1,3-Benzoxazol-2-yl)-2-(hydroxyethoxy)phenyl]acetonitrile

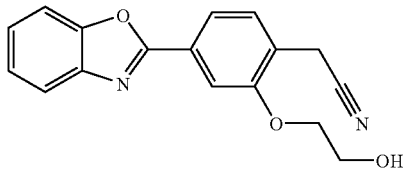

To a 100 mL round-bottom flask with 3-hydroxy-4-methylbenzoic acid (2.5 g, 16.4 mmol) was added $SOCl_2$ (15 mL) dropwise. This reaction was refluxed for 30 min, cooled to rt and the excess $SOCl_2$ removed in vacuo. The oily acid chloride was dissolved in THF (15 mL) and the solution was added dropwise to a mixture of 2-aminophenol (1.8 g, 16.4 mmol), triethylamine (1.7 g, 16.4 mmol) in THF (30 mL) at 0° C. The reaction was then brought to rt for 0.5 h and the precipitate was removed by filtration. The filtrate was concentrated and dried in vacuo. To the dark brown solid residue was added toluene (20 mL) and p-toluenesulfonic acid (15.6 g, 82 mmol). The reaction was refluxed overnight, cooled to rt and dissolved in EtOAc (500 mL). The EtOAc solution was washed with $H_2O$ (3×5 mL), dried ($MgSO_4$), filtered, and concentrated in vacuo. The residue was recrystallized in EtOAc to afford 5-(1,3-benzoxazol-2-yl)-2-methylphenol as a light yellow solid. MS (ESI) 226 (M+H)+.

A solution of 5-(1,3-benzoxazol-2-yl)-2-methylphenol (355 mg, 1.6 mmol) in DMF (10 mL) was cooled to 0° C. and NaH (70 mg, 1.7 mmol) was added slowly. After 15 min, (2-bromoethoxy)(tert-butyl)dimethylsilane (370 μL, 1.7 mmol) was added. The reaction was then elevated to 90° C. for 1 h and EtOAc (100 mL) was added. The EtOAc solution was washed with brine (3×20 mL), dried ($MgSO_4$), filtered, and concentrated in vacuo. The residue was purified by flash column (silica gel, hexanes:EtOAc 1:5) to afford 2-[3-(2-{[tert-butyl(dimethyl)silyl]oxy}-ethoxy)-4-methylphenyl]-1,3-benzoxazole.

2-[3-(2-{[Tert-butyl(dimethyl)silyl]oxy}ethoxy)-4-methylphenyl)]-1,3-benzoxazole (550 mg, 1.4 mmol) was combined with NBS (255 mg, 1.4 mmol), benzoyl peroxide (50 mg, catalyst) and $CCl_4$ (30 mL). The mixture was refluxed overnight, cooled to rt and EtOAc (200 mL) was added. The EtOAc solution was washed with brine (3×20 mL), dried ($MgSO_4$), filtered, and concentrated in vacuo. The residue was purified by flash column (silica gel, hexanes:EtOAc 5:1) to afford 2-[4-bromomethylphenyl-3-(2-{[tert-butyl(dimethyl)silyl]oxy}-ethoxy)]-1,3-benzoxazole.

The mixture of 2-[4-bromomethylphenyl-3-(2-{[tert-butyl(dimethyl)silyl]oxy}-ethoxy)]-1,3-benzoxazole (515 mg, 1.1 mmol) and sodium cyanide (164 mg, 3.3 mmol) in $DMF/H_2O$ (10 mL, 10/1) was stirred at 90° C. for 4 h, cooled to rt and EtOAc (200 mL) was added. The EtOAc solution was washed with brine (3×20 mL), dried ($MgSO_4$), filtered, and concentrated in vacuo. The residue was purified by flash column (silica gel, hexanes:EtOAc 1:1) to afford the desired [4-(1,3-benzoxazol-2-yl)-2-(hydroxyethoxy)phenyl]acetonitrile. $^1$H NMR ($CD_3OD$, 300 MHz) δ 7.90 (m 1H), 7.80 (m, 2H), 7.62 (m, 1H), 7.49 (d, 1H), 7.40 (m, 2H), 4.36(m, 2H), 4.10 (m, 2H), 3.78 (s, 2H). MS (ESI) 295 (M+H)+.

EXAMPLE 17

[4-(1,3-Benzoxazol-2-yl)-2-chlorophenyl]acetonitrile

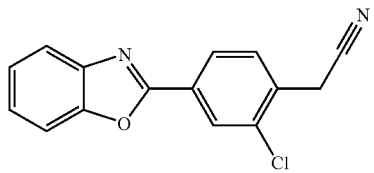

A solution of 2-(3-chloro-4-methylphenyl)-1,3-benzoxazole (780 mg, 3.2 mmol), N-bromosuccinimide (590 mg, 3.3 mmol) and $CCl_4$ (30 mL) was mixed with a catalytic quantity of benzoyl peroxide. The mixture was heated at reflux for 12 h. The reaction mixture was concentrated, and partitioned between saturated aqueous $Na_2CO_3$ (20 mL) and $CH_2Cl_2$ (20 mL). The aqueous layer was extracted with $CH_2Cl_2$ (2×20 mL). The combined organic extracts were dried ($MgSO_4$), and concentrated under reduced pressure to afford, after chromatography on silica gel (EtOAc:hexanes 1:9), 2-[4-(bromomethyl)-3-chlorophenyl]-1,3-benzoxazole as a colorless solid.

A slurry of NaCN (435 mg, 8.9 mmol), 2-[4-(bromomethyl)-3-chlorophenyl]-1,3-benzoxazole (940 mg, 2.9 mmol), DMF (30 mL) and $H_2O$ (30 mL) was stirred at rt for 12 h. The reaction mixture was poured into brine (250 mL) and filtered. The resultant colorless solid was purified by flash chromatography on silica gel (EtOAc:hexanes 1:9) to afford the desired [4-(1,3-benzoxazol-2-yl)-2-chlorophenyl]acetonitrile as a colorless solid: $^1$H NMR ($CDCl_3$, 300 MHz) δ 8.32 (s, 1H), 8.19 (dd, 1H), 7.77–7.80 (m, 1H), 7.70 (d, 1H), 7.59–7.61 (m, 1H), 7.38–7.41 (m, 2H), 3.92 (s, 2H). MS (ESI) 269 (M+H)+.

EXAMPLE 18

2,3-Bis[4-(1,3-benzoxazol-2-yl)-2-chlorophenyl]propanenitrile

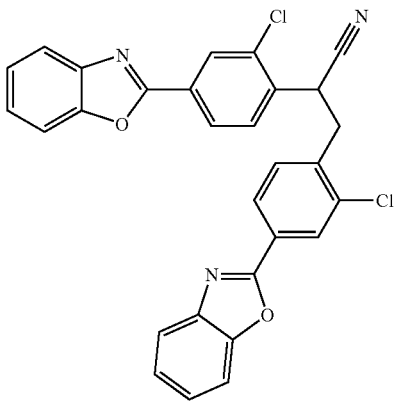

A solution of 2-[4-(bromomethyl)-3-chlorophenyl]-1,3-benzoxazole (150 mg, 0.46 mmol), KCN (36 mg, 0.55 mmol), and 18-crown-6 (145 mg, 0.55 mmol) is refluxed in MeCN (5 mL) for 10 minutes. The reaction is poured into H$_2$O (100 mL) and extracted with CH$_2$Cl$_2$ (2×30 mL). The organic extracts are dried (MgSO$_4$), concentrated under reduced pressure, and purified by flash chromatography (EtOAc:hexanes 1:10) to afford the desired 2,3-bis[4-(1,3-benzoxazol-2-yl)-2-chlorophenyl]propanenitrile as a colorless solid: $^1$H NMR (CDCl$_3$, 300 MHz) δ 8.32 (dd, 2H), 8.20 (d, 1H), 8.11 (d, 1H), 7.80–7.83 (m, 2H), 7.71 (d, 1H), 7.61–7.63 (m, 2H), 7.39–7.45 (m, 5), 4.85 (t, 1H), 3.40–3.50 (m, 2H). MS (ESI) 511 (M+H)$^+$.

EXAMPLE 19

1-[4-(1,3-Benzoxazol-2-yl)-2-chlorophenyl]cyclopentanecarbonitrile

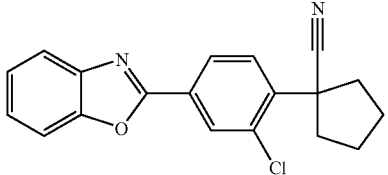

A solution of [4-(1,3-benzoxazol-2-yl)-2-chlorophenyl]acetonitrile (270 mg, 1.0 mmol) and THF (20 mL) was cooled to −78° C. A solution of NaHMDS (3.7 mL, 2.2 mmol, 0.6M solution in PhMe) was added dropwise via syringe to the reaction. After 15 min at −78° C., 1,4-dibromobutane (143 μL, 1.2 mmol) was added dropwise via syringe. The cooling bath was removed, and the reaction was allowed to warm to rt. The reaction was quenched by the addition of silica gel (600 mg) and concentrated to dryness. The residue was purified by flash chromatography on silica gel (EtOAc:hexanes 1:5) to afford the desired 1-[4-(1,3-benzoxazol-2-yl)-2-chlorophenyl]cyclopentanecarbonitrile as a colorless solid: $^1$H NMR (CDCl$_3$, 300 MHz) δ 8.34 (s, 1H), 8.12 (dd, 1H), 7.77–7.80 (m, 1H), 7.56–7.62 (m, 2H), 7.35–7.42 (m, 2H), 2.71–2.78 (m, 2H), 2.14–2.26 (m, 2H), 1.89–2.01 (m, 4H). MS (ESI) 323 (M+H)$^+$.

EXAMPLE 20

1-[4-(1,3-Benzoxazol-2-yl)-2chlorophenyl]cyclohexanecarbonitrile

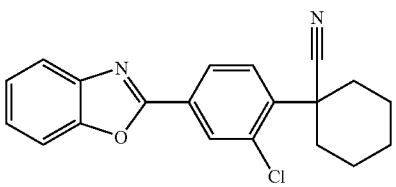

Utilizing the general procedure outlined for 1-[4-(1,3-benzoxazol-2-yl)-2-chlorophenyl]cyclopentanecarbonitrile, [4-(1,3-benzoxazol-2-yl)-2-chlorophenyl]acetonitrile (400 mg, 1.5 mmol) and 1,5-dibromopentane (250 μL, 1.8 mmol) reacted to afford the desired 1-[4-(1,3-benzoxazol-2-yl)-2-chlorophenyl]cyclohexanecarbonitrile as a colorless solid: $^1$H NMR (CDCl$_3$, 300 MHz) δ 8.22 (d, 1H), 8.06 (d, 1H), 7.68–7.73 (m, 1H), 7.51–7.55 (m, 2H), 7.28–7.35 (m, 2H), 2.49 (d, 2H), 1.73–2.00 (m, 8H). MS (ESI) 337 (M+H)$^+$.

EXAMPLE 21

[4-(1,3-Benzoxazol-2-yl)-2-chlorophenyl](fluoro)acetonitrile

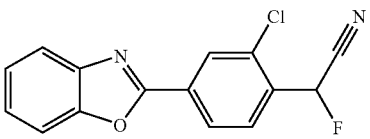

A solution of [4-(1,3-benzoxazol-2-yl)-2-chlorophenyl]acetonitrile (98 mg, 0.36 mmol) and dry THF (5 mL) was cooled to −78° C. A solution of tert-butyllithium (500 μL, 0.80 mmol, 1.7M solution in pentane) was added dropwise via syringe at −78° C. After 1 h, a solution of N-fluorobenzenesulfonimide (113 mg, 0.36 mmol) and dry THF (1.5 mL) was added dropwise via syringe at −78° C. The cooling bath was removed, and the reaction mixture was gradually allowed to warm to rt, and was maintained at rt for 8 h. The reaction was quenched with silica gel (300 mg) and concentrated to dryness. The residue was purified by flash chromatography on silica gel (EtOAc:hexanes, 1:3) to afford the desired [4-(1,3-benzoxazol-2-yl)-2-chlorophenyl](fluoro)acetonitrile as a colorless solid: $^1$H NMR (CDCl$_3$, 300 MHz) δ 8.32 (s, 1H), 8.24 (2, 1H), 7.74–7.84 (m, 2H), 7.56–7.60 (m 1H), 7.35–7.43 (m, 2H), 6.45 (d, 1H). MS (ESI) 287 (M+H)$^+$.

EXAMPLE 22

2-[4-(1,3-Benzoxazol-2-yl)-2-methoxyphenyl]acetonitrile

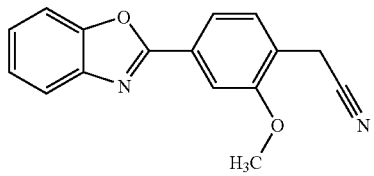

3-Methoxy-4-methyl benzoic acid (1.2 g, 7.2 mmol) and thionyl chloride (10 mL) was heated to reflux conditions under argon until no starting material was observed by TLC. After cooling mixture to rt and concentration in vacuo, the resulting brown oil was dissolved in THF (15 mL) and slowly added to a cooled mixture of 2-aminophenol (780 mg, 7.1 mmol), diisopropylethyl amine (1.5 mL, 8.6 mmol) and THF (20 mL) at 0° C. Reaction mixture was allowed to warm to rt. After one hour, no starting material acid was observed by TLC. After concentrating reaction mixture in vacuo, the resulting brown oil was purified by flash chromatography on silica gel, using 1:4 EtOAc:hexanes. This afforded the desired intermediate, N-(2-hydroxyphenyl)-3-methoxy-4-methylbenzamide, as a yellow solid. A mixture of N-(2-hydroxyphenyl)-3-methoxy-4-methylbenzamide (1.5 g, 5.88 mmol), toluene (30 mL), p-toluenesulfonic acid monohydrate (7.6 g, 40 mmol) and molecular sieves was refluxed overnight. After cooling reaction to rt, filtered washing with warn chloroform and concentrated filtrate in vacuo. The resulting brown oil was purified by flash chromatography on silica gel using 1:4 EtOAc:hexanes to give the desired intermediate, 2-(3-methoxy-4-methylphenyl)-1, 3-benzoxazole, as a colorless solid.

2-(3-Methoxy-4-methylphenyl)-1,3-benzoxazole (1.0 g, 4.1 mmol), carbon tetrachloride (18 mL), benzoyl peroxide (66 mg, 0.3 mmol) and N-bromosuccinimide (970 mg, 5.4 mmol) was heated to reflux conditions under argon and placed under a UV light. After one hour, no starting material was observed by TLC. After cooling mixture to rt, filtered, washing with dichoromethane. After concentrating filtrate in vacuo, the resulting colorless solid was purified by flash chromatography, using a gradient elution of 1:4 EtOAc: hexanes to EtOAc. This afforded the desired intermediate, 2-[4-(bromomethyl)-3-methoxyphenyl]-1,3-benzoxazole, as a colorless solid.

A mixture of 2-[4-(bromomethyl)-3-methoxyphenyl]-1,3-benzoxazole (318 mg, 1 mmol), dimethylformamide (7.5 mL) and deionized water (2.5 mL) was stirred at rt. Sodium cyanide (150 mg, 3.0 mmol) was added to reaction. After 3 h, dimethylformamide (10 mL) was added to help dissolve solids in reaction mixture. Let reaction mixture stir overnight at rt. Workup was done by washing reaction with brine (3×30 mL), extraction with EtOAc, combined organic extracts, dried ($Na_2SO_4$), filtered and removed solvent in vacuo. Flash chromatography of resulting orange solid on silica gel using a gradient elution of 1:9 EtOAc:hexanes to 1:3 EtOAc:hexanes afforded the desired intermediate, [4-(1, 3-benzoxazol-2-yl)-2-methoxyphenyl]acetonitrile as a yellow solid. $^1$H NMR($CDCl_3$, 300 MHz) δ 7.86–7.36 (m, 7H), 3.99 (s, 3H), 3.74 (s, 2H), 2.59–1.91 (m, 8H). MS (ESI) 265 $(M+H)^+$.

EXAMPLE 23

2-[4-(1,3-Benzoxazol-2-yl)-2-methoxyphenyl]propanenitrile

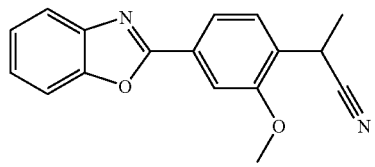

4-(1,3-benzoxazol-2-yl)-2-methoxybenzonitrile (22 mg, 0.82 mmol) was dissolved and cooled to −78° C. in THF (8 mL) in an oven dried flask flushed with argon. NaHMDS (1.5 mL, 0.90 mmol) was added and the mixture was stirred at −78° C. for 30 min. Iodomethane (84 μL, 0.90 mmol) was added and the mixture was brought to rt and stirred for an additional 45 min. The crude mixture was adsorbed onto silica gel and purified by automated flash chromatography using an EtOAc/hexanes gradient to afford the desired 2-[4-(1,3-benzoxazol-2-yl)-2-methoxyphenyl]propanenitrile as a pale yellow oil: $^1$H NMR ($CDCl_3$, 300 MHz) δ 7.89–7.86 (d, 1H), 7.79–7.76 (m, 2H), 7.61–7.56 (m, 2H), 7.40–7.36 (m, 2H), 4.32–4.30 (q, 1H), 4.00 (s, 3H), 1.63–1.61 (d, 1H) MS (ESI) 279 $(M+H)^+$.

EXAMPLE 24

2-[4-(1,3-Benzoxazol-2-yl)-2-methoxyphenyl]butanenitrile

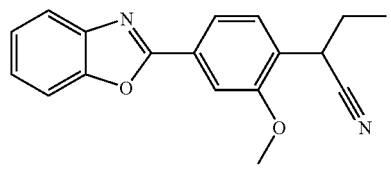

Utilizing the general procedure outlined in the synthesis of 2-[4-(1,3-benzoxazol-2-yl)-2-methoxyphenyl]propanenitrile, 4-(1,3-benzoxazol-2-yl)-2-methoxybenzonitrile (300 mg, 1.1 mmol) was reacted with iodoethane (90 μL, 1.1 mmol) to afford the desired 2-[4-(1,3-benzoxazol-2-yl)-2-methoxyphenyl]butanenitrile as a yellow solid: $^1$H NMR ($CDCl_3$, 300 MHz) δ 7.87–7.84 (d, 1H), 7.79–7.74 (m, 2H), 7.59–7.53 (m, 2H), 7.37–7.34 (m, 2H), 4.22–4.17 (t, 1H), 3.97 (s, 3H), 1.95–1.89 (m, 2H), 1.13–1.08 (t, 3H). MS (ESI) 293 $(M+H)^+$.

EXAMPLE 25

2-[4-(1,3-Benzoxazol-2-yl)-2-methoxyphenyl]pentanenitrile

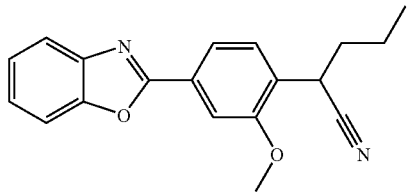

Utilizing the general procedure outlined in the synthesis of 2-[4-(1,3-benzoxazol-2-yl)-2-methoxyphenyl]propanenitrile, 4-(1,3-benzoxazol-2-yl)-2-methoxybenzonitrile (200 mg, 0.75 mmol) was reacted with 1-iodopropane (73 µL, 0.75 mmol) to afford the desired 2-[4-(1,3-benzoxazol-2-yl)-2-methoxyphenyl]pentanenitrile as a yellow solid: $^1$H NMR (CDCl$_3$, 300 MHz) δ 7.87–7.84 (d, 1H), 7.79–7.75 (m, 2H), 7.60–7.54 (m, 2H), 7.38–7.35 (m, 2H), 4.27–4.23 (t, 1H), 3.98 (s, 3H), 1.89–1.82 (M, 2H), 1.57–1.53 (m, 2H), 1.00–0.95 (t, 3H). MS (ESI) 307 (M+H)$^+$.

EXAMPLE 26

1-[4-(1,3-Benzoxazol-2-yl)-2-methoxyphenyl]cyclobutanecarbonitrile

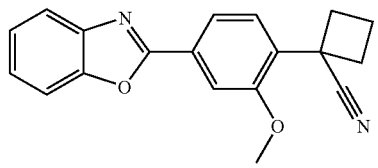

Utilizing the general procedure outlined in the synthesis of 2-[4-(1,3-benzoxazol-2-yl)-2-methoxyphenyl]propanenitrile, 4-(1,3-benzoxazol-2-yl)-2-methoxybenzonitrile (250 mg, 0.95 mmol) was reacted with 1,3-Dibromopropane (120 µL, 1.1 mmol) to afford the desired 1-[4-(1,3-benzoxazol-2-yl)-2-methoxyphenyl]cyclobutanecarbonitrile as a colorless solid: $^1$H NMR (CDCl$_3$, 300 MHz) δ 7.89–7.87 (m, 3H), 7.62–7.55 (m, 1H) 7.39–7.36 (m, 2H), 7.32–7.26 (m, 1H), 4.05 (s, 3H), 2.90–2.83 (m, 2H), 2.67–2.47 (m, 4H). MS (ESI) 305 (M+H)$^+$.

EXAMPLE 27

1-[4-(1,3-Benzoxazol-2-yl)-2-methoxyphenyl]cyclohexanecarbonitrile

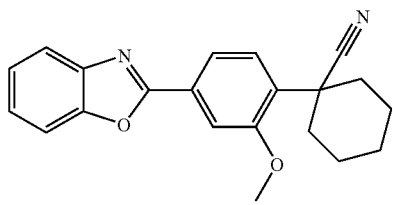

Utilizing the general procedure outlined for the synthesis of 1-[4-(1,3-benzoxazol-2-yl)-2-methoxyphenyl]cyclobutanecarbonitrile, 4-(1,3-benzoxazol-2-yl)-2-methoxybenzonitrile (250 mg, 0.95 mmol) was reacted with 1,5-dibromopentane (160 µL, 1.1 mmol) to afford the desired 1-[4-(1,3-benzoxazol-2-yl)-2-methoxyphenyl] cyclohexanecarbonitrile as a colorless solid: $^1$H NMR (CDCl$_3$, 300 MHz) δ 7.83–7.75 (m, 3H), 7.59–7.56 (m, 1H) 7.45–7.43 (d, 1H), 7.38–7.34 (m, 2H), 4.04 (s, 3H), 2.41–2.38 (d, 2H), 1.92–1.15 (m, 8H). MS (ESI) 333 (M+H)$^+$.

EXAMPLE 28

1-[4-(1,3-Benzoxazol-2-yl)-2-methoxyphenyl]cyclopropanecarbonitrile

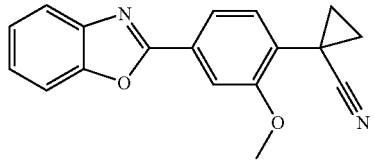

4-(1,3-benzoxazol-2-yl)-2-methoxybenzonitrile (250 mg, 0.95 mmol) was dissolved in CH$_2$Cl$_2$ (5 mL). Benzyltrimethylammonium hydroxide (200 µL, 0.095 mmol) in 50% aqueous NaOH (5 mL) was added and the mixture was stirred overnight at rt and then diluted with H$_2$O. The aqueous mixture was extracted with CH$_2$Cl$_2$ (2×25 mL). The combined organic layers are dried over MgSO$_4$, filtered and concentrated in vacuo. The residue was adsorbed onto silica gel and purified by automated flash chromatography using an EtOAc/hexanes gradient to afford the desired 1-[4-(1,3-benzoxazol-2-yl)-2-methoxyphenyl]cyclopropanecarbonitrile as a yellow solid: $^1$H NMR (CDCl$_3$, 300 MHz) δ 7.80–7.78 (m, 3H), 7.60–7.57 (m, 1H), 7.39–7.33 (m, 3H), 4.07 (s, 3H), 1.70–1.66 (t, 2H), 1.34–1.30 (t, 2H). MS (ESI) 291 (M+H)$^+$.

EXAMPLE 29

1-[4-(1,3-Benzoxazol-2-yl)-2-methoxyphenyl]cyclopentanecarbonitrile

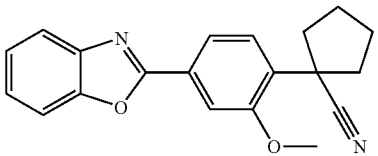

3-Methoxy-4-methyl benzoic acid (1.2 g, 7.2 mmol) and thionyl chloride (10 mL) was heated to reflux conditions under argon until no starting material was observed by TLC. After cooling mixture to rt and concentration in vacuo, the resulting brown oil was dissolved in THF (15 mL) and slowly added to a cooled mixture of 2-aminophenol (780 mg, 7.1 mmol), diisopropylethyl amine (1.5 mL, 8.6 mmol) and THF (20 mL) at 0° C. Reaction mixture was allowed to warm to rt. After one hour, no starting material acid was observed by TLC. After concentrating reaction mixture in vacuo, the resulting brown oil was purified by flash chromatography on silica gel, using 1:4 EtOAc:hexanes. This afforded the desired intermediate, N-(2-hydroxyphenyl)-3-methoxy-4-methylbenzamide, as a yellow solid.

A mixture of N-(2-hydroxyphenyl)-3-methoxy-4-methylbenzamide (1.5 g, 5.8 mmol), toluene (30 mL), p-toluenesulfonic acid monohydrate (7.6 g, 40 mmol) and molecular sieves was refluxed overnight. After cooling reaction to rt, filtered washing with warm chloroform and concentrated filtrate in vacuo. The resulting brown oil was purified by flash chromatography on silica gel using 1:4 EtOAc:hexanes to give the desired intermediate, 2-(3-methoxy-4-methylphenyl)-1,3-benzoxazole, as a colorless solid.

2-(3-Methoxy-4-methylphenyl)-1,3-benzoxazole (1.0 g, 4.1 mmol), carbon tetrachloride (18 mL), benzoyl peroxide (66 mg, 0.3 mmol) and N-bromosuccinimide (970 mg, 5.4 mmol) was heated to reflux conditions under argon and placed under a UV light. After 1 h, no starting material was observed by TLC. After cooling mixture to rt, filtered, washing with dichoromethane. After concentrating filtrate in vacuo, the resulting colorless solid was purified by flash chromatography, using a gradient elution of 1:4 EtOAc: hexanes to EtOAc. This afforded the desired intermediate, 2-[4-(bromomethyl)-3-methoxyphenyl]-1,3-benzoxazole, as a colorless solid.

A mixture of, 2-[4-(bromomethyl)-3-methoxyphenyl]-1,3-benzoxazole (318 mg, 1 mmol), dimethylformamide (7.5 mL) and deionzed water (2.5 mL) was stirred at rt. Sodium cyanide (150 mg, 3.0 mmol) was added to reaction. After 3 h, dimethylformamide (10 mL) was added to help dissolve solids in reaction mixture. Let reaction mixture stir overnight at rt. Workup was done by washing reaction with brine (3×30 mL), extraction with EtOAc, combined organic extracts, dried ($Na_2SO_4$), filtered and removed solvent in vacuo. Flash chromatography of resulting orange solid on silica gel using a gradient elution of 1:9 EtOAc:hexanes to 1:3 EtOAc:hexanes afforded the desired intermediate, [4-(1,3-benzoxazol-2-yl)-2-methoxyphenyl]acetonitrile, as a light yellow solid.

[4-(1,3-Benzoxazol-2-yl)-2-methoxyphenyl]acetonitrile (130 mg, 0.49 mmol) in THF (5.0 mL) was cooled to −78° C. under argon atmosphere. Sodium bis(trimethylsilyl)amide (1.8 mL, 1.08 mmol) was added slowly and after fifteen minutes, added 1,4-dibromobutane (0.07 mL, 0.59 mmol) to dark brown reaction mixture. Let mixture warm to rt overnight. After concentrating reaction mixture in vacuo, the resulting pink oil was purified by flash chromatography, using a gradient elution of 1:9 EtOAc:hexanes to 1:4 EtOAc: hexanes. This afforded the desired compound, 1-[4-(1,3-benzoxazol-2-yl)-2-methoxyphenyl]cyclopentanecarbonitrile, as a yellow solid. $^1$H NMR(CDCl$_3$, 300 MHz) δ 7.86–7.26 (m, 7H), 4.07 (s, 3H), 2.59–1.91 (m, 8H). MS (ESI) 319.1 (M+H)$^+$.

EXAMPLE 30

[4-(1,3-Benzoxazol-2-yl)-2,6-dimethoxyphenyl]acetonitrile

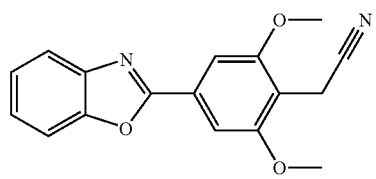

Thionyl chloride (10 mL) and 3,5-dimethoxy-4-methylbenzoic acid (1.0 g, 5.1 mmol) was refluxed under argon until no starting material was observed by TLC. After cooling reaction mixture to rt, concentrated mixture in vacuo. The resulting brown oil was added to a mixture of 2-aminophenol (580 mg, 5.3 mmol), diisopropylethyl amine (1.1 mL, 6.3 mmol) and THF (40 mL) at 0° C. and then brought to rt overnight. After concentrating mixture in vacuo, the resulting brown oil was purified by flash chromatography on silica gel, using a gradient elution from 1:9 EtOAc:hexanes to 1:1 EtOAc:hexanes. This afforded the desired intermediate, 3,5-dimethoxy-N-(2-methoxyphenyl)-4-methylbenzamide, as a colorless solid.

A mixture of 3,5-dimethoxy-N-(2-methoxyphenyl)-4-methylbenzamide (1.29 g, 4.49 mmol), toluene (22 mL), p-toluenesulfonic acid monohydrate (5.9 g, 31 mmol) and molecular sieves was refluxed until no starting material was observed by TLC. Cooled mixture to rt and filtered, washing with warm chloroform. Removal of solvent from filtrate afforded a yellow solid. Purification of crude solid by flash chromatography on silica gel using 1:3 EtOAc:hexanes gave the desired intermediate, 2-(3,5-dimethoxy-4-methylphenyl)-1,3-benzoxazole, as a colorless solid.

A mixture of 2-(3,5-dimethoxy-4-methylphenyl)-1,3-benzoxazole (260 mg, 1 mmol), carbon tetrachloride (4.2 mL), benzoyl peroxide (15 mg, 0.06 mmol) and N-bromosuccinimide (270 mg, 1.5 mmol) was heated to reflux conditions under argon overnight. Concentration of cooled reaction mixture in vacuo afforded a yellow solid. Flash chromatography on silica gel of crude material using 1:4 EtOAc: hexanes gave the desired intermediate, 2-[4-bromomethyl)-3,5-dimethoxyphenyl]-1,3-benzoxazole, as a colorless solid.

2-[4-bromomethyl)-3,5-dimethoxyphenyl]-1,3-benzoxazole (160 mg, 0.46 mmol), dimethylformamide (5.0 mL), deionized water (1.2 mL) and sodium cyanide (77 mg, 1.6 mmol) was stirred at rt. After no starting material was observed by TLC, washed reaction mixture with brine (3×15 mL) and extracted with EtOAc (3×20 mL). Combined organic extracts, dried ($Na_2SO_4$), filtered and concentrated in vacuo. The crude residue was chromatographed on silica gel, eluting with 1:4 EtOAc:hexanes to give the desired compound, [4-(1,3-benzoxazol-2-yl)-2,6-dimethoxyphenyl] acetonitrile, as a colorless solid. $^1$H NMR (CDCl$_3$, 300 MHz) δ 7.62 (m, 1H), 7.49 (m, 1H), 7.42 (s, 2H), 7.41(m, 1H), 7.40 (m, 1H), 4.03 (s, 6H), 3.77 (s, 2H). MS (ESI) 295 (M+H)$^+$.

EXAMPLE 31

(2-Chloro-4-[1,3]oxazolo[4,5-b]pyridin-2-ylphenyl) acetonitrile

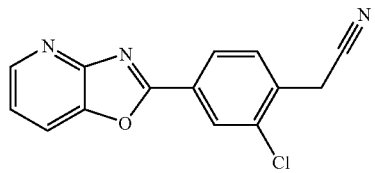

A solution of 3-chloro-4-methylbenzoic acid (5.0 g, 29 mmol), N-bromosuccinimide (5.7 g, 32 mmol), benzoyl peroxide (710 mg, 2.9 mmol) in CCl$_4$ (300 mL) was heated at reflux for 2.5 h. The mixture was concentrated under reduced pressure and dissolved in MTBE. The organic mixture was washed with 1N NaOH (3×25 mL). The aqueous mixture was acidified with 1N HCl to pH 2 and extracted with CH$_2$Cl$_2$ (3×25 mL). The combined organic layers were dried over MgSO$_4$, filtered and concentrated to afford 4-(bromomethyl)-3-chlorobenzoic acid.

A suspension of 4-(bromomethyl)-3-chlorobenzoic acid (4.0 g, 16 mmol) in DMF (120 mL) and H$_2$O (40 mL) was treated with NaCN (2.4 g, 49 mmol) and heated to 80° C. for 2 h. The mixture was cooled to rt and acidified with 1N HCl. The aqueous mixture was extracted with CH$_2$Cl$_2$ (3×25 mL). The combined organic layers were concentrated under reduced pressure and dissolved in MTBE. The organic mixture was washed with H$_2$O and brine (3×25 mL), dried over MgSO$_4$, filtered and concentrated to afford 3-chloro-4-(cyanomethyl)benzoyl chloride.

Oxalyl chloride (1.7 mL, 19 mmol) was added to a suspension of 3-chloro-4-(cyanomethyl)benzoyl chloride (2.5 g, 13 mmol) in CH$_2$Cl$_2$ (120 mL). DMF (1 drop) was added to the suspension and the mixture was stirred for 2 h at rt. The mixture was filtered and the filtrate was concentrated under reduced pressure to afford 3-chloro-4-(cyanomethyl)benzoyl chloride.

The acid chloride was dissolved in CH$_2$Cl$_2$ (20 mL) and added in solution to a stirring suspension of 2-amino-3-hydroxypyridine (1.4 g, 13 mmol) and triethylamine (5.4 mL, 38 mmol) in CH$_2$Cl$_2$ (100 mL). The mixture was stirred overnight. The reaction mixture was partitioned between CH$_2$Cl$_2$ and H$_2$O. Aqueous mixture was extracted with CH$_2$Cl$_2$ (2×25 mL). Combined organic layers are washed with sat. NaHCO$_3$, and brine (2×25 mL) dried over MgSO$_4$, filtered and concentrated in vacuo. The residue was adsorbed onto silica gel and purified by automated flash chromatography using an EtOAc/hexanes gradient to afford 3-chloro-4-(cyanomethyl)-N-(3-hydroxypyridin-2-yl)benzamide as a yellow solid. MS (ESI) 288 (M+H).

3-chloro-4-(cyanomethyl)-N-(3-hydroxypyridin-2-yl) benzamide (550 mg, 1.9 mmol) was refluxed in POCl$_3$ (15 mL) for 2.5 h. Excess POCl$_3$ was removed by distillation and the mixture was cooled to rt. The crude mixture was diluted with H$_2$O. The aqueous layer was made basic (pH 14) with 1N NaOH and extracted with CH$_2$Cl$_2$ (3×20 mL). The residue was adsorbed onto silica gel and purified by automated flash chromatography using an EtOAc/hexane gradient to afford (2-chloro-4-[1,3]oxazolo[4,5-b]pyridin-2-ylphenyl)acetonitrile as a colorless solid: $^1$H NMR (CDCl$_3$, 300 MHz) δ 8.65–8.63 (d, 1H), 8.41 (s, 1H), 8.30–8.27 (d, 1H), 7.93–7.90 (d, 2H), 7.77–7.74 (d, 2H), 7.38–7.34 (m, 2H) 3.95 (s, 2H). MS (ESI) 270 (M+H)$^+$.

EXAMPLE 32

[4-(5-Chloro-1,3-benzoxazol-2-yl)phenyl]acetonitrile

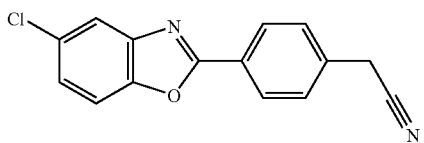

To a solution of 5-chlorobenzoxazole (100 mg, 0.65 mmol) in anhydrous THF at −78° C. under Argon was added n-Butyllithium (0.45 mL, 1.6M in hexanes). 30 min later, zinc chloride (1.95 mL, 1.0M in ether) was added. The reaction mixture was warmed to 0° C. for 1 h and then to 22° C. Then 4-bromophneylphenylacetonitrile (128 mg, 0.65 mmol) and Pd(Ph$_3$P)$_4$ (38 mg, 0.033 mmol) were added. The mixture was heated to reflux for overnight, after which time it was cooled to rt and poured in to a separatory funnel containing EtOAc (50 mL), where it was washed with sat. brine (3×20 mL). The EtOAc solution was dried (MgSO$_4$), filtered and concentrated in vacuo. The crude residue was chromatographed on silica gel, eluting with 3:1 hexanes:EtOAc to afford a off-colorless solid. $^1$H NMR (CDCl$_3$, 300 MHz) δ 8.26 (d, 2H), 7.76 (d, 1H), 7.51 (m, 3H), 7.35 (m, 1H), 3.87 (s, 3H). MS (ESI) 269(M+H)$^+$.

EXAMPLE 33 AND 34

2-[3-Methoxy-4-(1H-1,2,3-triazol-1-ylmethyl)phenyl]-1,3 benzoxazole

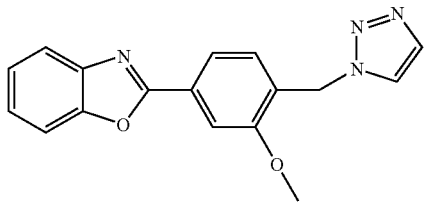

2-[3-Methoxy-4-(2H-1,2,3-triazol-2-ylmethyl)phenyl]-1,3-benzoxazole

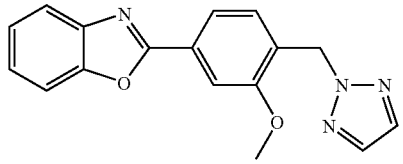

A slurry of 2-[4-(bromomethyl)-3-methoxyphenyl]-1,3-benzoxazole (300 mg, 1.0 mmol) and 1H-1,2,3-triazole (70 mg, 1.0 mmol), and Cs$_2$CO$_3$ (325 mg, 1.0 mmol) and MeCN (10 mL) was stirred vigorously at rt for 8 h. Silica gel (600 mg) was added, and the reaction mixture was concentrated to dryness. The residue was purified by flash chromatography on silica gel (linear gradient of EtOAc in hexanes from 0 to 100% over 25 min) to afford 2-[3-methoxy-4-(1H-1,2,3-triazol-1-ylmethyl)phenyl]-1,3-benzoxazole and 2-[3-methoxy-4-(2H-1,2,3-triazol-2-ylmethyl)phenyl]-1,3-benzoxazole as colorless solids. 2-[3-methoxy-4-(1H-1,2,3-triazol-1-ylmethyl)phenyl]-1,3-benzoxazole: $^1$H NMR (CDCl$_3$, 300 MHz) δ 7.72–7.78 (m, 3H), 7.69 (s, 1H), 7.59 (s, 1H), 7.53–7.56 (m, 1H), 7.31–7.34 (m, 2H), 7.20 (d, 1H), 5.59 (s, 2H), 3.96 (s, 3H). MS (ESI) 307 (M+H). 2-[3-methoxy-4-(2H-1,2,3-triazol-2-ylmethyl)phenyl]-1,3-benzoxazole: $^1$H NMR (CDCl$_3$, 300 MHz) δ 7.76–7.80 (m, 3H), 7.68 (s, 1H), 7.56–7.59 (m, 2H), 7.34–7.38 (m, 2H), 7.04 (d, 1H), 5.74 (s, 2H), 3.99 (s, 3H). MS (ESI) 307 (M+H)$^+$.

EXAMPLE 35

2-[3-Methoxy-4-(1H-1,2,4-triazol-1-ylmethyl)phenyl]-1,3-benzoxazole

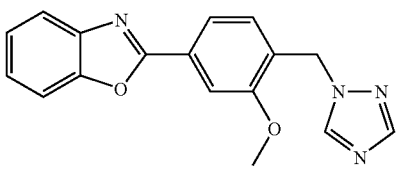

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and 1,2,4-triazole (70 mg, 1.0 mmol) afforded the desired 2-[3-methoxy-4-(1H-1,2,4-triazol-1-ylmethyl)phenyl]-1,3-benzoxazole as a colorless solid: $^1$H NMR (CDCl$_3$, 300 MHz) δ 8.13 (s, 1H), 7.92 (s, 1H), 7.71–7.78 (m, 2H), 7.51–7.54 (m, 1H), 7.29–7.34 (m, 2H), 7.24 (d, 2H), 5.34 (s, 2H), 3.92 (s, 3H). MS (ESI) 307 (M+H)$^+$.

EXAMPLE 36

2-[4-(1H-Imidazol-1-ylmethyl)-3-methoxyphenyl]1,3-benzoxazole

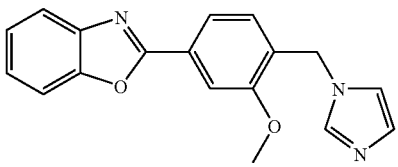

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and imidazole (70 mg, 1.0 mmol) afforded the desired 2-[4-(1H-imidazol-1-ylmethyl)-3-methoxyphenyl]-1,3-benzoxazole as a colorless solid: $^1$H NMR (CDCl$_3$, 300 MHz) δ 7.57–7.86 (m, 6H), 7.26–7.40 (m, 4H), 5.53 (s, 2H), 4.02 (s, 3H). MS (ESI) 306 (M+H)$^+$.

EXAMPLE 37

2-[3-Methoxy-4-(1H-pyrazol-1-ylmethyl)phenyl]-1,3-benzoxazole

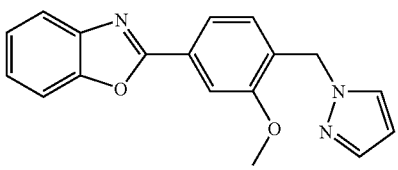

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and pyrazole (70 mg, 1.0 mmol) afforded the desired 2-[3-methoxy-4-(1H-pyrazol-1-ylmethyl)phenyl]-1,3-benzoxazole as a colorless solid: $^1$H NMR (CDCl$_3$, 300 MHz) δ 7.60–7.91 (m, 7H), 7.38–7.41 (m, 2H), 6.54 (m, 1H), 5.81 (s, 2H), 4.11 (s, 3H). MS (ESI) 306 (M+H)$^+$.

EXAMPLE 38

2-{4-[(4-Bromo-1H-imidazol-1-yl)methyl]-3-methoxyphenyl}-1,3-benzoxazole

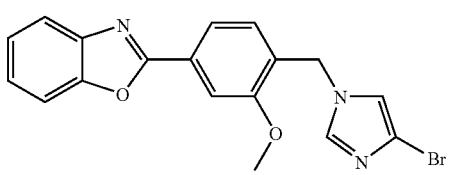

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and 4-bromo-1H-imidazole (150 mg, 1.0 mmol) afforded the desired 2-{4-[(4-bromo-1H-imidazol-1-yl)methyl]-3-methoxyphenyl}-1,3-benzoxazole as a colorless solid: $^1$H NMR (CDCl$_3$, 300 MHz) δ 7.94–7.99 (m, 3H), 7.85–7.87 (m, 1H), 7.75–7.78 (m, 1H), 7.65–7.68 (m, 1H), 7.43–7.49 (m, 2H), 7.20 (s, 1H), 5.55 (s, 2H), 4.09 (s, 3H). MS (ESI) 384 (M+H)$^+$.

EXAMPLE 39 AND 40

2-[3-Methoxy-4-(2H-tetrazol-2-ylmethyl)phenyl]-1,3-benzoxazole

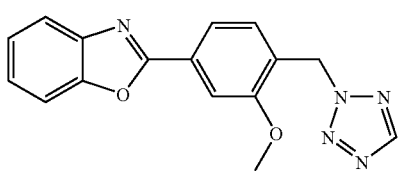

2-[3-Methoxy-4-(1H-tetrazol-1-ylmethyl)phenyl]-1,3-benzoxazole

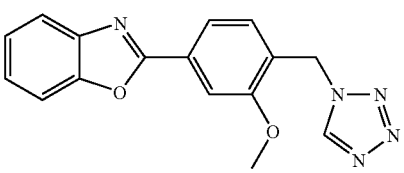

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and 1H-tetrazole (70 mg, 1.0 mmol) afforded 2-[3-methoxy-4-(2H-tetrazol-2-ylmethyl)phenyl]-1,3-benzoxazole and 2-[3-methoxy-4-(1H-tetrazol-1-ylmethyl)phenyl]-1,3-benzoxazole as colorless solids. 2-[3-methoxy-4-(2H-tetrazol-2-ylmethyl)phenyl]-1,3-benzoxazole: ¹H NMR (CDCl₃, 300 MHz) δ 8.52 (s, 1H), 7.72–7.79 (m, 3H), 7.52–7.55 (m, 1H), 7.31–7.34 (m, 2H), 7.21 (d, 1H), 5.86 (s, 2H), 3.93 (s, 3H). MS (ESI) 308 (M+H). 2-[3-methoxy-4-(1H-tetrazol-1-ylmethyl)phenyl]-1,3-benzoxazole: ¹H NMR (CDCl₃, 300 MHz) δ 8.66 (s, 1H), 7.85 (d, 1H), 7.74–7.83 (m, 2), 7.55–7.59 (m, 1H), 7.41 (d, 1H), 7.34–7.40 (m, 2H), 5.61 (s, 2H), 3.98 (s, 3H). MS (ESI) 308 (M+H)⁺.

EXAMPLE 41 AND 42

Methyl 1-[4-(1,3-benzoxazol-2-yl)-2-methoxybenzyl]-1H-imidazole-5-carboxylate

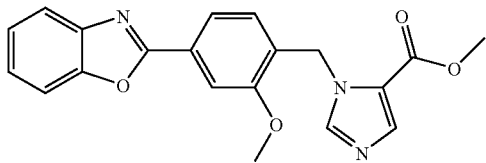

Methyl 1-[4-(1,3-benzoxazol-2-yl)-2-methoxybenzyl]-1H-imidazole-4-carboxylate

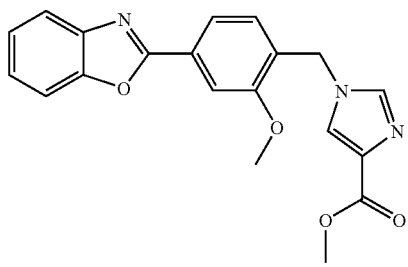

Utilizing the general procedure outlined for 2-[3-methoxy-4-(1H-1,2,3-triazol-1-ylmethyl)phenyl]-1,3-benzoxazole, reaction of 2-[4-(bromomethyl)-3-methoxyphenyl]-1,3-benzoxazole (300 mg, 1.0 mmol) and methyl 4-imidazole carboxylate (126 mg, 1.0 mmol) afforded methyl 1-[4-(1,3-benzoxazol-2-yl)-2-methoxybenzyl]-1H-imidazole-5-carboxylate and methyl 1-[4-(1,3-benzoxazol-2-yl)-2-methoxybenzyl]-1H-imidazole-4-carboxylate as colorless solids. Methyl 1-[4-(1,3-benzoxazol-2-yl)-2-methoxybenzyl]-1H-imidazole-5-carboxylate: ¹H NMR (CDCl₃, 300 MHz) δ 7.73–7.80 (m, 4H), 7.57–7.60 (m, 1H), 7.34–7.38 (m, 2H), 7.15 (d, 1H), 5.58 (s, 2H), 4.00 (s, 3H), 3.83 (s, 3H). MS (ESI) 364 (M+H)⁺. Methyl 1-[4-(1,3-benzoxazol-2-yl)-2-methoxybenzyl]-1H-imidazole-4-carboxylate: ¹H NMR (CDCl₃, 300 MHz) δ 7.75–7.84 (m, 3H), 7.57–7.64 (m, 3H), 7.34–7.38 (m, 2H), 7.18 (d, 1H), 5.17 (s, 2H), 3.97 (s, 3H), 3.86 (s, 3H). MS (ESI) 364 (M+H)⁺.

EXAMPLE 43

2-{3-methoxy-4-[(1-methyl-1H-tetrazol-5-yl)methyl]phenyl}-1,3-benzoxazole

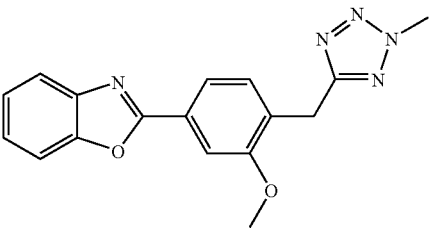

Azidotrimethylsilane (251 µL, 1.89 mmol) was added to a stirring suspension of 4-(1,3-benzoxazol-2-yl)-2-methoxybenzonitrile (250 mg, 0.949 mmol) and dibutyltin oxide (24 mg, 0.09 mmol) in toluene (5 mL). The mixture was heated at 110° C. overnight. The mixture was cooled to rt and the toluene was removed in vacuo. The residue was dissolved in EtOAc and extracted 10% NaHCO₃ (3×25 mL). The combined aqueous extracts were acidified to pH 2 with 3N HCl. The acidic aqueous mixture was extracted with EtOAc (3×25 mL). The combined organic layers are dried over MgSO₄, filtered and concentrated in vacuo to afford 2-[3-methoxy-4-(1H-tetrazol-5-ylmethyl)phenyl]-1,3-benzoxazole: ¹H NMR (DMSO-d₆, 300 MHz) δ 7.82–7.78 (m, 3H), 7.75 (s, 1H), 7.46–7.42 (m, 3H), 4.30 (s, 2H), 3.90 (s, 3H). MS (ESI) 308 (M+H)⁺.

Iodomethane (38 µL, 0.42 mmol) was added to a stirring solution of 2-[3-methoxy-4-(1H-tetrazol-5-ylmethyl)phenyl]-1,3-benzoxazole (130 mg, 0.42 mmol) and triethylamine (120 µL, 0.83 mmol) in CH₃CN (5 mL). The mixture was stirred at rt overnight. The crude mixture was adsorbed onto silica gel and purified by automated flash chromatography using an EtOAc/hexanes gradient to afford the desired 2-[3-methoxy-4-(morpholin-4-ylmethyl)phenyl]-1,3-benzoxazole as a colorless solid: ¹H NMR (CDCl₃, 300 MHz) δ 7.84–7.77 (m, 3H), 7.58 (m 1H), 7.39–7.36 (m, 2H), 7.30–7.27 (d, 1H), 4.32 (s, 2H), 3.96 (s, 6H). MS (ESI) 322 (M+H)⁺.

EXAMPLE 44

2-[3-Methoxy-4-(pyrrolidin-1-ylmethyl)phenyl]-1,3-benzoxazole

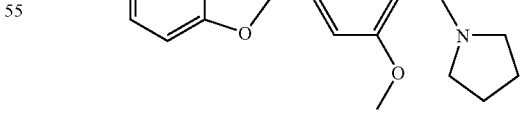

Pyrrolidine (226 µL, 2.83 mmol) was added to a stirring solution of 2-[4-(bromomethyl)-3-methoxyphenyl]-1,3-benzoxazole (300 mg, 0.94 mmol) and triethylamine (390 µL, 2.8 mmol) in CH₂Cl₂ (5 mL). The mixture was stirred at rt overnight. Crude mixture was adsorbed onto silica gel and purified by automated flash chromatography using an EtOAc/hexanes gradient to afford the desired 2-[3-methoxy- 4-(pyrrolidin-1-ylmethyl)phenyl]-1,3-benzoxazole as a colorless solid: $^1$H NMR (CDCl$_3$, 300 MHz) δ 7.82–7.80 (m, 1H), 7.77–7.74 (m, 1H), 7.71 (s, 1H), 7.56–7.50 (m, 2H), 7.35–7.30 (m, 2H), 3.94 (s, 3H), 3.71 (s, 2H), 2.59 (s, 4H), 1.81–1.78 (m, 4H). MS (ESI) 309 (M+H)$^+$.

EXAMPLE 45

2-[3-Methoxy-4-(piperidin-1-ylmethyl)phenyl]-1,3-benzoxazole

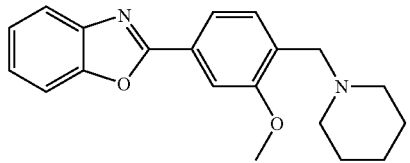

Utilizing the general procedure outlined for 2-[3-methoxy-4-(pyrrolidin-1-ylmethyl)phenyl]-1,3-benzoxazole, 2-[4-(bromomethyl)-3-methoxyphenyl]-1,3-benzoxazole (300 mg, 0.942 mmol) was reacted with piperidine (279 μL, 2.83 mmol) and triethylamine (394 μL, 2.83 mmol) in CH$_2$Cl$_2$ (5 mL) to afford the desired 2-[3-methoxy-4-(piperidin-1-ylmethyl)phenyl]-1,3-benzoxazole as a colorless solid: $^1$H NMR (CDCl$_3$-d, 300 MHz) δ 7.86–7.83 (m, 1H), 7.79–7.76 (m, 1H), 7.73 (s, 1H), 7.61–7.55 (m, 2H), 7.37–7.34 (m, 2H), 3.96 (s, 3H), 3.59 (s, 2H), 2.47 (br, 4H), 1.66–1.58 (m, 4H), 1.46–1.45 (m, 2H). MS (ESI) 323 (M+)$^+$.

EXAMPLE 46

2-[3-Methoxy-4-(pyridin-2-ylmethyl)phenyl]-1,3-benzoxazole

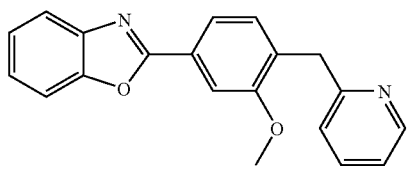

A solution of 2-[4-(bromomethyl)-3-methoxyphenyl]-1,3-benzoxazole (320 mg, 1.0 mmol) and THF (10 mL) was treated with Zn powder (activated by grinding with mortar and pestle), a drop of chlorotrimethylsilane, and a drop of 1,2-dibromoethane. The mixture was heated at reflux for 1 h. The resultant organozinc reagent was filtered through a plug of Celite, and transferred to a flask containing 2-bromopyridine (360 mg, 2.0 mmol) and Pd(Ph$_3$P)$_4$ (115 mg, 0.1 mmol). The mixture was degassed with bubbling argon for 15 min, and heated at reflux for 12 h. The reaction was poured into H$_2$O (40 mL) and extracted with CH$_2$Cl$_2$ (2×30 mL). The organic extracts were dried (MgSO$_4$) and concentrated to afford a colorless solid. Purification of the solid by flash chromatography on silica gel (EtOAc:hexanes 3:1) afforded the desired 2-[3-methoxy-4-(pyridin-2-ylmethyl)phenyl]-1,3-benzoxazole as a yellow solid: $^1$H NMR (CDCl$_3$, 300 MHz) δ 8.55 (d, 1H), 7.76–7.82 (m, 3H), 7.56–7.62 (d, 2H), 7.32–7.36 (m, 3H), 7.11–7.16 (m, 2H), 4.23 (s, 2H), 3.95 (s, 3H). MS (ESI) 317 (M+H)$^+$.

EXAMPLE 47

2-[3-Methoxy-4-(pyridin-3-ylmethyl)phenyl]-1,3-benzoxazole

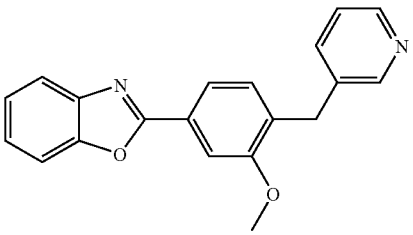

A mixture of 2-[4-(bromomethyl)-3-methoxyphenyl]-1,3-benzoxazole (190 mg, 0.58 mmol), 3-pyridylboronic acid (70 mg, 0.58 mmol), Pd(Ph$_3$P)$_4$ (70 mg, 0.06 mmol), K$_2$CO$_3$ (200 mg, 1.5 mmol), DME (6 mL) and H$_2$O (3 mL) was degassed with bubbling Ar for 15 min. The mixture was heated at 80° C. for 1 h. The reaction was poured into H$_2$O (40 mL) and extracted with CH$_2$Cl$_2$ (2×30 mL). The organic extracts were dried (MgSO$_4$) and concentrated to afford a colorless solid. Purification of the solid by flash chromatography on silica gel (EtOAc:hexanes 3:1) afforded the desired 2-[3-methoxy-4-(pyridin-3-ylmethyl)phenyl]-1,3-benzoxazole as a yellow solid: $^1$H NMR (CDCl$_3$, 300 MHz) δ 8.56 (br s, 1H), 8.45 (br d, 1H), 7.74–7.80 (m, 3H), 7.50–7.58 (m, 2H), 7.32–7.37 (m, 2H), 7.17–7.24 (m, 2H), 4.00 (s, 2H), 3.93 (s, 3H). MS (ESI) 317 (M+H)$^+$.

EXAMPLE 48

2-[3-Methoxy-4-(pyridin-4-ylmethyl)phenyl]-1,3-benzoxazole

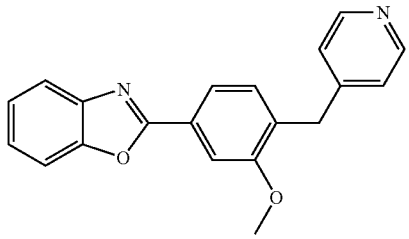

Utilizing the general procedure outlined for 2-[3-methoxy-4-(pyridin-3-ylmethyl)phenyl]-1,3-benzoxazole, 2-[4-(bromomethyl)-3-methoxyphenyl]-1,3-benzoxazole (270 mg, 0.81 mmol), 4-pyridylboronic acid (100 mg, 0.81 mmol) reacted to afford the desired 2-[3-methoxy-4-(pyridin-4-ylmethyl)phenyl]-1,3-benzoxazole as a colorless solid: $^1$H NMR (CDCl$_3$, 300 MHz) δ 8.46 (br s, 2H), 7.75–7.81 (m, 3H), 7.56–7.59 (m, 1H), 7.34–7.36 (m, 2H), 7.22 (d, 1H), 7.13 (d, 2H), 4.00 (s, 2H), 3.92 (s, 3H). MS (ESI) 317 (M+H)$^+$.

EXAMPLE 49

[4-(1,3-Benzoxazol-2-yl)-2-chlorophenyl](pyridin-2-yl)methanol

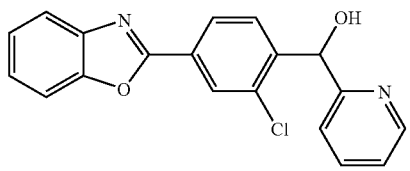

A solution of benzoxazole (5.4 g, 46 mmol) and THF (150 mL) was cooled to −78° C. A solution of n-butyllithium (29 mL, 47 mmol, 1.6M solution in hexanes) was added dropwise via syringe over 15 min. After 1 h at −78° C., a solution of ZnCl$_2$ (95 mL, 47 mmol, 0.5M solution in ether) was added dropwise via syringe over 5 min. The reaction mixture was allowed to warm to rt, and maintained for 1 h. 2-Chloro-4-bromobenzonitrile (3.3 g, 15 mmol) and Pd(Ph$_3$P)$_4$ (880 mg, 0.76 mmol) were added to the reaction mixture. The mixture was degassed with bubbling argon for 15 min, then heated at reflux for 1 h. The reaction was quenched by the addition of 1 N HCl (150 mL), and extracted with CH$_2$Cl$_2$ (3×150 mL). The organic extracts were combined, dried (MgSO$_4$), and concentrated to afford, after flash chromatography on silica gel (acetone:hexane 1:5), 4-(1,3-benzoxazol-2-yl)-2-chlorobenzonitrile as a yellow solid.

A solution of 4-(1,3-benzoxazol-2-yl)-2-chlorobenzonitrile (510 mg, 2.0 mmol) and CH$_2$Cl$_2$ was cooled to −78° C. Diisobutylaluminum hydride (2 mL, 1.0M solution in PhMe) was added to the reaction dropwise via syringe over 30 min. The cooling bath was removed, and the reaction mixture is allowed to warm to rt. The reaction was quenched by the addition of a saturated solution of sodium potassium tartrate (50 mL). The resultant slurry was filtered, and the organic layer was separated, dried (MgSO$_4$), and concentrated under reduced pressure to afford, after flash chromatography (acetone:hexane 1:5), 4-(1,3-benzoxazol-2-yl)-2-chlorobenzaldehyde as a yellow solid.

A solution of 2-bromopyridine (110 mg, 0.7 mmol) and THF (10 mL) was cooled to −78° C. n-Butyllithium (0.44 mL, 0.7 mmol, 1.6M solution in THF) was added dropwise via syringe. After 15 min, a solution of 4-(1,3-benzoxazol-2-yl)-2-chlorobenzaldehyde (150 mg, 0.6 mmol) and THF (2 mL) was added via syringe, and the reaction was allowed to warm to rt. The reaction is quenched by the addition of H$_2$O (20 mL). The mixture is extracted with EtOAc (3×120 mL), and the combined organic extracts are dried (MgSO$_4$), and concentrated under reduced pressure to afford, after flash chromatography on silica gel (EtOAc:hexanes 1:1), the desired [4-(1,3-benzoxazol-2-yl)-2-chlorophenyl](pyridin-2-yl)methanol as a colorless solid: $^1$H NMR (CDCl$_3$, 300 MHz) δ 8.58 (d, 1H), 8.28 (d, 1H), 8.10 (dd, 1H), 7.55–7.55 (m, 4H), 7.23–7.37 (m, 4H). MS (ESI) 337 (M+H)$^+$.

EXAMPLE 50

2-[3-Chloro-4-(2-morpholin-4-ylethyl)phenyl]-1,3-benzoxazole

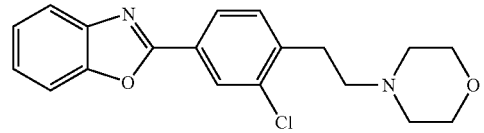

A solution of [4-(1,3-benzoxazol-2-yl)-2-chlorophenyl]acetonitrile (1.11 g, 3.88 mmol) in CH$_2$Cl$_2$ (40 mL) was cooled −78° C. Diisobutylaluminum hydride (4.7 mL, 4.7 mmol, 1.0M solution in PhMe) was added slowly. The mixture was stirred at −78° C. under argon for 3 h and allowed to warm slowly to rt overnight. Reaction mixture was cooled to 0° C. quenched with acetone and 1N HCl. The mixture was partitioned between EtOAc and H$_2$O. The aqueous layer was extracted with EtOAc (3×10 mL). The combined organic layers were dried over MgSO$_4$, filtered and concentrated to afford [4-(1,3-benzoxazol-2-yl)-2-chlorophenyl]acetaldehyde.

The crude aldehyde was treated with NaCNBH$_3$ and morpholine in MeOH/CH$_2$Cl$_2$ (2 mL). The crude mixture was adsorbed onto silica gel and purified by automated flash chromatography using an EtOAc/hexanes gradient to afford the desired 2-[3-chloro-4-(2-morpholin-4-ylethyl)phenyl]-1,3-benzoxazole: $^1$H NMR (CDCl$_3$, 300 MHz) δ 8.26–8.25 (d, 1H), 8.09–8.06 (m, 1H), 7.79–7.74 (m, 1H), 7.43–7.34 (m, 3H), 3.78–3.75 (m, 4H), 3.05–3.00 (m, 2H), 2.68–2.59 (m, 6H). MS (ESI) 343 (M+H)$^+$.

EXAMPLE 51

2-(3-Methyl-4-pyridin-2-ylphenyl)-1,3-benzoxazole

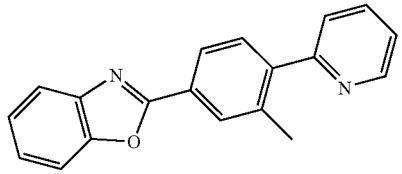

Polyphosphoric acid (100 mL) was added to a beaker containing 2-aminophenol (17.7 g, 162 mmol) and 4-bromo-3-methylbenzoic acid (13.6 g, 64 mmol). The mixture was heated at 200° C. for 1 h, then poured into ice water (1 L) and allowed to stand overnight. The mixture was filtered and dried to afford 2-(4-bromo-3-methyl(phenyl))-benzoxazole as a colorless solid. A solution of 2-(4-bromo-3-methyl(phenyl))-benzoxazole (670 mg, 2.3 mmol), 2-(tributylstannyl)pyridine (850 mg, 2.3 mmol), Pd(Ph$_3$P)$_4$ (270 mg, 0.23 mmol) and DMF (23 mL) was degassed with bubbling argon for 15 min. The reaction mixture was heated at 100° C. for 8 h. The reaction was cooled to rt, and KF (500 mg) and H$_2$O (250 mL) were added. The mixture was extracted with MTBE (3×50 mL), and the combined organic extracts were washed with water (2×20 mL), brine (1×20 mL), dried (MgSO$_4$), and concentrated to afford an oil. Purification of the oil by flash chromatography on silica gel (EtOAc:

hexanes 1:2) afforded the desired 2-(3-methyl-4-pyridin-2-ylphenyl)-1,3-benzoxazole as a colorless solid: ¹H NMR (CDCl₃, 300 MHz) δ 8.91 (d, 1H), 8.52 (t, 1H), 8.19 (s, 1H), 8.15 (d, 1H), 7.97 (br t, 1H), 7.89 (d, 1H), 7.70–7.72 (m, 1H), 7.61 (d, 1H), 7.51–7.54 (m, 1H), 7.30–7.33 (m, 2H), 2.45 (s, 3H), MS (ESI) 287 (M+H)⁺.

EXAMPLE 52

2-(3-Methyl-4-pyrimidin-2-ylphenyl)-1,3-benzoxazole

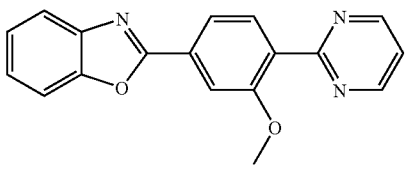

A slurry of 2-(4-bromo-3-methyl(phenyl))-benzoxazole (330 mg, 1.1 mmol), KOAc (330 mg, 3.4 mmol), [1,1'-bis(diphenylphosphino)ferrocene]dichloropalladium(II) (93 mg, 0.11 mmol), bis(pinacolato)diboron (360 mg, 1.4 mmol), and dioxane (30 mL) was degassed with Ar for 15 min. The reaction was heated at 80° C. for 12 h, then quenched by the addition of H₂O (20 mL). The mixture was extracted with MTBE (3×50 mL), and the combined organic extracts were dried (MgSO4), and concentrated under reduced pressure to afford, after flash chromatography on silica gel (EtOAc:hexanes 1:3), 2-[3-methyl-4-(4,4,5,5-tetramethyl-1,3,2-dioxaborolan-2-yl)phenyl]-1,3-benzoxazole as a colorless solid.

A mixture of 2-[3-methyl-4-(4,4,5,5-tetramethyl-1,3,2-dioxaborolan-2-yl)phenyl]-1,3-benzoxazole (190 mg, 0.5 mmol), Pd(Ph₃P)₄ (60 mg, 0.05 mmol), CsF (300 mg, 2.0 mmol), and DME (5 mL) was degassed with Ar for 15 min. The reaction was heated at 80° C. for 12 h, then quenched by the addition of H₂O (20 mL). The mixture was extracted with MTBE (3×50 mL), and the combined organic extracts were dried (MgSO₄), and concentrated under reduced pressure to afford, after flash chromatography on silica gel (EtOAc:hexanes 1:1) the desired 2-(3-methyl-4-pyrimidin-2-ylphenyl)-1,3-benzoxazole as a colorless solid: ¹H NMR (CDCl₃, 300 MHz), δ 8.82 (d, 2H), 7.99–8.20 (m, 2H), 7.98 (d, 2H), 7.75–7.77 (m, 1H), 7.54–7.57 (m, 1H), 7.30–7.35 (m, 2H), 7.20 (t, 1H), 2.64 (s, 3H). MS (ESI) 288 (M+H)⁺.

EXAMPLE 53

4-(1,3-Benzoxazol-2-yl)-2-methoxyphenol

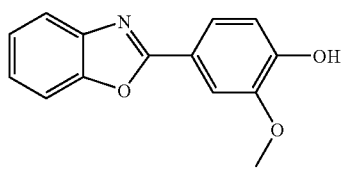

4-hydroxy-3-methoxybenzoic acid (25 g, 149 mmol) and 2-amino phenol (16.2 g, 149 mmol) were combined in a round bottom flask. Trimethylsilyl polyphosphate (80 mL) was added neat. The mixture was heated at 180° C. for 30 min. The mixture is poured over ice and allowed to stir overnight. The suspension was filtered to afford 4-(1,3-benzoxazol-2-yl)-2-methoxyphenol as a pale green solid. MS (ESI) 242 (M+H)⁺.

EXAMPLE 54

2-(3-Methoxy-4-pyridin-2-ylphenyl)-1,3-benzoxazole hydrochloride salt

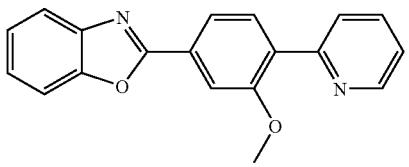

The solution of 4-(1,3-benzoxazol-2-yl)-2-methoxyphenol (7.1 g, 29.4 mmol) in anhydrous DMF (100 mL) was treated with Cs₂CO₃ (9.6 g, 29.4 mmol) and N-phenyl trifluoromethanesulfonimide (10.5 g, 29.4 mmol) at 22° C. for 30 min. After which time it was quenched with sat. NaHCO₃ (50 mL) and diluted with EtOAc (500 mL). The EtOAc solution was washed with sat. brine (3×10 mL), dried (MgSO₄), filtered and concentrated in vacuo. The residue was chromatographed on silica gel, eluting with 4:1 hexanes:EtOAc to afford 4-(1,3-benzoxazol-2-yl)-2-methoxyphenyl trifluoromethanesulfonate as a colorless oil. MS (ESI) 374 (M+H)⁺.

The solution of 4-(1,3-benzoxazol-2-yl)-2-methoxyphenyl trifluoromethanesulfonate (11.7 g, 31.3 mmol) in anhydrous DMF (150 mL) was degassed via Argon for 10 min. Then 2-tri-n-butylstannylpyridine (11.5 g, 31.3 mmol) and Pd(Ph₃P)₄ (3.6 g, 3.1 mmol) were added at 22° C. The resulting mixture was then heated at 100° C. for 1 h under Argon. Cooled the reaction mixture to 22° C., then filtered through a pad of Celite. The filtrate was concentrated under reduced pressure to give after purification by flash chromatography (silica gel, 3:1; hexanes:EtOAc) the desired compound as a off-colorless solid which was then disolved in diethyl ether (200 mL) and precipitated as the hydrochloride salt upon treatment with 1M HCl in diethyl ether (20 mL). The resulting colorless solid was then treated with EtOAc (1 L), heated at refluxing, then cooled to 22° C., collected the solid by filtration to yield a colorless solid as desired compound. (M.p. 215° C.). ¹H NMR (CD₃OD, 300 MHz) δ 8.88 (m, 1H), 8.69 (m, 1H), 8.41 (d, 1H), 8.09 (m, 3H), 7.91 (d, 1H), 7.82 (m, 1H), 7.45 (m, 1H), 7.48 (m, 2H), 4.10 (s, 3H). MS (ESI) 303 (M+H)⁺.

EXAMPLE 55

5-(1,3-Benzoxazol-2-yl)-2-pyridin-2-yl benzonitrile

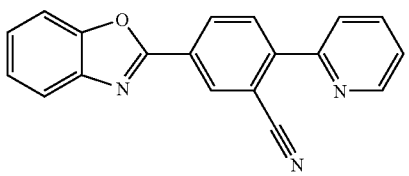

To a solution of methyl 3-cyano-4-methoxy-benzoate (1.5 g, 7.9 mmol) in $CH_3OH/H_2O$ (25 mL; 1:1), was added LiOH (2.5 g, 60.0 mmol). The reaction mixture was refluxed for 2 h, cooled at rt and 6M HCl was added dropwise until pH 2 was obtained. The precipitate was collected, washed with $H_2O$ (3×20 mL), dried in vacuo to afford 3-cyano-4-methoxy-benzoic acid. MS (ESI) 178 $(M+H)^+$. To a 100 mL round-bottom flask with 3-cyano-4-methoxy-benzoic acid (1.4 g, 7.8 mmol), was added $SOCl_2$ (15 mL) dropwise. The reaction was refluxed for 1 h and was cooled to rt. The excess of $SOCl_2$ was removed in vacuo and the oily acid chloride was dissolved in THF (15 mL). The resulting solution was added dropwise to a mixture of 2-aminophenol (1.3 g, 11.7 mmol), triethylamine (1.3 g, 11.7 mmol) and THF (30 mL) at 0° C. The reaction was warmed up to rt and stirred an additional 3 h. The precipitate was removed by filtration and the filtrate was concentrated and dried in vacuo. The dark brown solid residue was dissolved in toluene (20 mL) and p-toluenesulfonic acid (6.0 g, 46.8 mmol) was added. The reaction was refluxed overnight, cooled to rt, and EtOAc (300 mL) was added. The EtOAc solution was washed with brine (3×20 mL), dried ($MgSO_4$), filtered and concentrated in vacuo. The residue was purified by flash chromatography (silica gel, $CHCl_3:CH_3OH$ 8:1) to afford 5-(1,3-benzoxazol-2-yl)-2-methoxy benzonitrile. MS ESI) 251$(M+H)^+$.

To a solution of 5-(1,3-benzoxazol-2-yl)-2-methoxy benzonitrile (270 mg, 1.1 mmol) in $CH_2Cl_2$ (5 mL) at 0° C., was added $BBr_3$ (1.0M solution in $CH_2Cl_2$, 430 µL, 4.4 mmol) dropwise. The reaction was stirred at it for 4 h. EtOAc (150 mL) was added, as well as $H_2O$ (30 mL). The organic layer was washed with brine (2×20 mL), dried ($MgSO_4$), concentrated and the crude product was recrystallized in EtOAc to afford 5-(1,3-benzoxazol-2-yl)-2-hydroxy benzonitrile. MS (ESI) 237 $(M+H)^+$.

To a solution of 5-(1,3-benzoxazol-2-yl)-2-hydroxy benzonitrile (230 mg, 1.0 mmol) and pyridine (154 mg, 2 mmol) in $CH_2Cl_2$ (5 mL) at 0° C., was added trifluoromethanesulfonic anhydride (330 mg, 1.2 mmol) dropwise. The reaction was elevated to rt and stirred for 2 h. EtOAc (150 mL) was added, as well as $H_2O$ (50 mL). The organic layer was washed with brine (2×20 mL), dried ($MgSO_4$) and the crude material was purified by flash column (silica gel, hexanes:EtOAc 4:1) to afford 4-(1,3-benzoxazol-2-yl)-2-cyanophenyltrifluoromethanesulfonate as yellow oil.

The degassed solution of 4-(1,3-benzoxazol-2-yl)-2-cyanophenyl trifluoromethanesulfonate (300 mg, 1.2 mmol) in DME (5 mL) was added 2-tri-n-butylstannylpyridine (273 mg, 0.74 mmol), tetrakis(triphenylphosphine)palladium(0) (150 mg, 0.1 mmol). The reaction was stirred at 90° C. overnight and cooled to rt. EtOAc (100 mL) was added, as well as brine (50 mL). The organic layer was washed with brine (2×20 mL), dried ($MgSO_4$), and the crude material was purified on flash column (silica gel, hexanes:EtOAc 3:1) to afford desired 5-(1,3-benzoxazol-2-yl)-2-pyridin-2-yl benzonitrile as pinkish solid. $^1$H NMR ($CD_3OD$, 300 MHz), δ 8.85 (d 1H), 8.72 (d, 1H), 8.59 (m, 1H), 8.08 (d, 1H), 7.91 (d, 2H), 7.85 (m, 1H), 7.65 (m, 1H), 7.45 (m, 3H). MS (ESI) 298 $(M+H)^+$.

EXAMPLE 56

2-(3-Methoxy-4-pyridin-3-ylphenyl)-1,3-benzoxazole

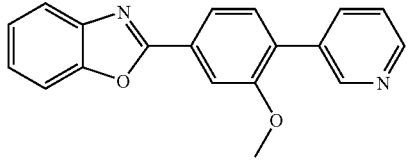

The solution of 4-(1,3-benzoxazol-2-yl)-2-methoxyphenyl trifluoromethanesulfonate (148 mg, 0.4 mmol) in 6 mL of 2:1 $DMF:H_2O$ was degassed via Argon for 10 min. Then $K_2CO_3$ (137 mg, 0.99 mmol), $Pd(Ph_3P)_4$ (23 mg, 0.02 mmol), n-$Bu_4NBr$ (128 mg, 0.40 mmol) and 3-Pyridylboronic acid (73 mg, 0.60 mmol) were added at 22° C. The resulting mixture was then heated at 75° C. for 1 h under Argon. Cooled the reaction mixture to 22° C., then filtered through a pad of Celite. The filtrate was concentrated under reduced pressure to give after purification by flash chromatography (silica gel, 3:1; hexanes:EtOAc) the desired compound as a yellow solid. $^1$H NMR ($CDCl_3$, 300 MHz) δ 8.83 (d, 1H), 8.60 (dd, 1H), 7.92 (m, 3H), 7.81 (m, 1H), 7.62 (m, 1H), 7.48 (d, 1H), 7.39 (m, 3H), 3.98 (s, 3H). MS (ESI) 303 $(M+H)^+$.

EXAMPLE 57

2-(3-Chloro-4-pyridin-3-ylphenyl)-1,3-benzoxazole

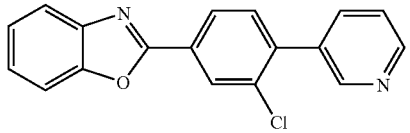

A suspension of 3-chloro-4-hydroxybenzoic acid (20.0 g, 11.6 mmol) in anhydrous dichloromethane (100 mL) was treated with oxalyl chloride (20 mL, 23.2 mmol) followed by few drops of DMF at 22° C. under argon. After 2 h stirring, the solution became clear, concentrated to dryness, dissolved in dichloromethane (50 mL) and added slowly to a solution of 2-aminophenol (12.6 g, 11.6 mmol) and TEA (9 mL, 11.6 mmol) in anhydrous DMC (50 mL). After 20 min stirring, filtered off salt, concentrated the mixture to afford 4-chloro-3-hydroxy-N-phenylbenzamide as a brown solid. MS (ESI) 264$(M+H)^+$. 4-Chloro-3-hydroxy-N-phenylbenzamide (4 g, 15.2 mmol) was treated with $POCl_3$ (5 mL) at reflux for 1 h. Concentrated and dissolved in dichloromethane (50 mL), washed with sat. $NaHCO_3$ (3×25 mL) and sat. brine (3×25 mL), dried ($MgSO_4$), concentrated in vacuo. The crude residue was chromatographed on silica gel, eluting with 2:1 hexanes:EtOAc to afford 4-(1,3-benzoxazol-2-yl)-2-chlorophenol as a colorless solid. MS (ESI) 246$(M+H)^+$. The solution of 4-(1,3-benzoxazol-2-yl)-2-methoxyphenol (800 mg, 3.3 mmol) in anhydrous DMF (10 mL) was treated with $Cs_2CO_3$ (1.1 g, 3.2 mmol) and N-phenyl trifluoromethanesulfonimide (1.2 g, 3.2 mmol) at 22° C. for 30 min. After which time it was quenched with sat. $NaHCO_3$ (20 mL) and diluted with EtOAc (50 mL). The EtOAc solution was washed with sat. brine (3×10 ml), dried (MgSO₄), filtered and concentrated in vacuo. The residue was chromatographed on silica gel, eluting with 6:1 hexanes:EtOAc to afford 4-(1,3-benzoxazol-2-yl)-2-chlorophenyl trifluoromethanesulfonate a colorless oil. MS (ESI) 378 (M+H)⁺. The solution of 4-(1,3-benzoxazol-2-yl)-2-chlorophenyl trifluoromethanesulfonate (150 mg, 0.4 mmol) in 6 mL of 2:1 DMF:H₂O was degassed via Argon for 10 min. Then K₂CO₃ (137 mg, 0.99 mmol), Pd(Ph₃P)₄ (23 mg, 0.02 mmol), n-Bu₄NBr (128 mg, 0.40 mmol) and 3-Pyridylboronic acid (73 mg, 0.60 mmol) were added at 22° C. The resulting mixture was then heated at 75° C. for 1 h under Argon. Cooled the reaction mixture to 22° C., then filtered through a pad of Celite. The filtrate was concentrated under reduced pressure to give after purification by flash chromatography (silica gel, 3:1; hexanes:EtOAc) the desired compound, as a yellow solid. ¹H NMR (CDCl₃, 300 MHz) δ 8.75 (d, 1H), 6.68 (dd, 1H), 8.42 (d, 1H), 8.24 (dd, 1H), 7.89 (dt, 1H), 7.81 (m, 1H), 7.63 (m, 1H), 7.52 (d, 1H), 7.42 (m, 3H). MS (ESI) 307 (M+H)⁺.

EXAMPLE 58

5-Fluoro-2-(3-methoxy-4-pyridin-2-ylphenyl)-1,3-benzoxazole hydrochloride

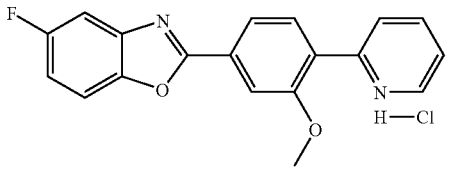

To 700 mL of degassed CH₃CN was added methyl vanillate (21.1 g, 116 mmol), N-phenyltrifluoromethanesulfonimide (41.3 g, 116 mmol), and cesium carbonate (37.7 g, 116 mmol). The mixture was stirred under an argon atmosphere for 48 h at which point it was partitioned between EtOAc (750 mL) and H₂O (750 mL). The organic layer was washed with saturated Na₂CO₃, H₂O, and brine, dried over MgSO₄, and concentrated in vacuo. The crude material was purified by column chromatography (1:9 EtOAc/hexanes) to give methyl 3-methoxy-4-{[(trifluoromethyl)sulfonyl]oxy}benzoate as a colorless oil that became a colorless solid upon standing. ¹H NMR (DMSO-d₆, 300 MHz) δ 7.77 (d, 1H), 7.68 (dd, 1H), 7.59 (d, 1H), 4.00 (s, 3H), 3.91 (s, 3H).

To 300 mL of degassed THF was added methyl 3-methoxy-4-{[(trifluoromethyl)sulfonyl]oxy}benzoate (20.95 g, 66.7 mmol), 2-pyridylzinc bromide (200 mL of 0.5M solution in THF, 100 mmol), and tetrakis(triphenylphosphine)palladium(0) (5.00 g, 4.3 mmol). The mixture was degassed with argon for an additional 30 minutes and heated at reflux under an argon atmosphere overnight. The reaction mixture was cooled to rt and concentrated in vacuo. The resultant brown residue was partitioned between EtOAc (1500 mL) and 50% saturated NaHCO₃ (1000 mL). The aqueous layer was extracted with EtOAc (500 mL), and the combined organic layers washed with brine, dried over MgSO₄, filtered, and concentrated in vacuo. The crude product was purified by column chromatography (0–25% EtOAc/hexanes) to give methyl 3-methoxy-4-pyridin-2-ylbenzoate as a colorless solid. ¹H NMR (DMSO-d₆, 300 MHz) δ 8.70 (d, 1H), 7.92–7.83 (m, 3H), 7.70–7.65 (m, 2H), 7.40–7.36 (m, 1H), 3.91 (s, 3H), 3.90 (s, 3H).

To 154 mL of a 50/50 solution of MeOH and H₂O was added lithium hydroxide monohydrate (13.85 g, 330 mmol). The solution was stirred until all of the salt dissolved, at which point methyl 3-methoxy-4-pyridin-2-ylbenzoate (8.02 g, 32.9 mmol) was added. The mixture was heated at reflux and stirred overnight. The reaction mixture was cooled to rt, neutralized with 6N HCl, and acidified to pH 4 with 1N HCl. A colorless solid crashed out of solution and was filtered to give 3-methoxy-4-pyridin-2-ylbenzoic acid as a colorless solid. ¹H NMR (DMSO-d₆, 300 MHz) δ 8.70 (d, 1H), 7.92–7.84 (m, 3H), 7.69–7.65 (m, 2H), 7.40–7.36 (m, 1H), 3.91 (s, 3H).

To a stirred solution of 4-fluoro-2-nitrophenol (4.05 g, 25.8 mmol) in MeOH (200 mL) was added tin(II) chloride dihydrate (17.47 g, 77.4 mmol). The reaction mixture was heated at reflux and monitored by LC/MS. When significant reduction was complete, the reaction mixture was cooled to rt, poured over ice, and made basic (pH 9) with 50% saturated NaHCO₃. The aqueous layer was extracted with EtOAc (2×200 mL) and the combined extracts washed with brine, dried over MgSO₄, filtered, and concentrated in vacuo to give 2-amino-4-fluorophenol as a grayish green solid. ¹H NMR (CDCl₃, 300 MHz) δ 6.64 (dd, 1H), 6.47 (dd, 1H), 6.33 (dt, 1H), 4.48 (br s, 1H), 3.78 (br s, 2H).

To 20 mL trimethylsilyl polyphosphate was added 2-amino-4-fluorophenol (523 mg, 4.11 mmol) and 3-methoxy-4-pyridin-2-ylbenzoic acid (857 mg, 3.74 mmol). The mixture was heated at 200° C. for 2 h, quenched over ice, and made basic (pH 14) with 1N NaOH. The aqueous phase was extracted with MTBE (300 mL), EtOAc (300 mL), MTBE (300 mL), and CH₂Cl₂ (300 mL). The combined organic layers were washed with brine, dried over MgSO₄, filtered, concentrated iii vacuo, and purified by column chromatography (0–50% EtOAc/hexanes). The free base was dissolved in ether and HCl (1N in ether) was added. The solution was filtered to give 5-fluoro-2-(3-methoxy-4-pyridin-2-ylphenyl)-1,3-benzoxazole hydrochloride as a purple solid. ¹H NMR (DMSO-d₆, 300 MHz) δ 8.87 (d, 1H), 8.34 (t, 1H), 8.18 (d, 1H), 7.97–7.93 (m, 3H), 7.90 (dd, 1H), 7.81–7.75 (m, 2H), 7.37 (dt, 1H), 4.02 (s, 3H); MS (ESI) 321 (M+H)⁺.

EXAMPLE 59

7-Fluoro-2-(3-methoxy-4-pyridin-2-ylphenyl)-1,3-benzoxazole hydrochloride

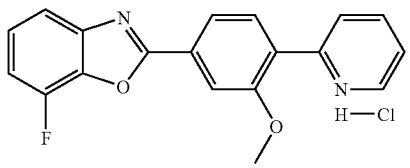

To a stirred slurry of 10% palladium on carbon (2.26 g, 2.12 mmol) in MeOH (100 mL) was added 4-bromo-2-fluoro-6-nitrophenol (5.00 g, 21.2 mmol). The reaction mixture was stirred under an H₂ atmosphere until significant reduction was seen by TLC. The mixture was filtered through Celite and concentrated in vacuo. The resultant solid was triturated with hexanes and reconcentrated to remove residual MeOH and give 2-amino-6-fluorophenol as a dark gray solid. $^1$H NMR (DMSO-$d_6$, 300 MHz) δ 10.86 (br s, 1H), 9.54 (br s, 2H), 7.25–7.19 (m, 1H), 7.13 (d, 1H), 6.94–6.86 (m, 1H).

To 7 mL trimethylsilyl polyphosphate was added 2-amino-6-fluorophenol (166 mg, 1.31 mmol) and 3-methoxy-4-pyridin-2-ylbenzoic acid (300 mg, 1.31 mmol). The mixture was heated at 200° C. for 2 h, quenched over ice, and made basic (pH 14) with 1N NaOH. The aqueous phase was extracted with EtOAc (3×150 mL). The combined organic layers were washed with brine, dried over MgSO$_4$, filtered, and concentrated in vacuo. The resultant oil was taken up in ether and reconcentrated to give a tan solid. The free base was dissolved in ether and HCl (1N in ether) was added. The solution was filtered to give 7-fluoro-2-(3-methoxy-4-pyridin-2-ylphenyl)-1,3-benzoxazole hydrochloride as a yellow solid. $^1$H NMR (DMSO-$d_6$, 300 MHz) δ 8.71 (d, 1H), 8.00 (t, 1H), 7.97–7.84 (m, 4H), 7.70 (d, 1H), 7.49–7.37 (m, 3H), 4.00 (s, 3H); MS (ESI) 321 (M+H)$^+$.

EXAMPLE 60

5-Bromo-2-(3-methoxy-4-pyridin-2-ylphenyl)-1,3-benzoxazole

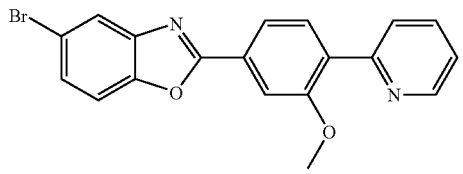

To a stirred solution of 4-bromo-2-nitrophenol (5.00 g, 22.9 mmol) in MeOH (120 mL) was added tin(II) chloride dihydrate (15.53 g, 68.8 mmol). The reaction mixture was heated at reflux and monitored by LC/MS. When significant reduction was complete, the reaction mixture was cooled to rt, poured over ice, and made basic (pH 9) with 50% saturated NaHCO$_3$. The aqueous layer was extracted with EtOAc (2×150 mL) and the combined extracts washed with brine, dried over MgSO$_4$, filtered, and concentrated in vacuo to give 2-amino-4-bromophenol as a dark gray solid. $^1$H NMR (CDCl$_3$, 300 MHz) δ 9.29 (br s, 1H), 6.71 (d, 1H), 6.56 (d, 1H), 6.49 (dd, 1H), 4.83 (br s, 2H).

To 20 mL trimethylsilyl polyphosphate was added 2-amino-4-bromophenol (752 mg, 4.00 mmol) and 3-methoxy-4-pyridin-2-ylbenzoic acid (916 mg, 4.00 mmol). The mixture was heated at 200° C. for 2 h, quenched over ice, and made basic (pH 14) with 1N NaOH. The aqueous phase was extracted with MTBE (3×300 mL). The combined organic layers were washed with brine, dried over MgSO$_4$, filtered, concentrated in vacuo, and purified by column chromatography (20–50% EtOAc/hexanes) to give 5-bromo-2-(3-methoxy-4-pyridin-2-ylphenyl)-1,3-benzoxazole as a pink solid. $^1$H NMR (DMSO-$d_6$, 300 MHz) δ 8.71 (d, 1H), 8.10 (d, 1H), 8.00 (t, 1H), 7.97–7.86 (m, 4H), 7.84 (d, 1H), 7.63 (dd, 1H), 7.39 (dt, (s, 3H); MS (ESI) 382 (M+H)$^+$.

EXAMPLE 61

5-Cyano-2-(3-methoxy-4-pyridin-2-ylphenyl)-1,3-benzoxazole

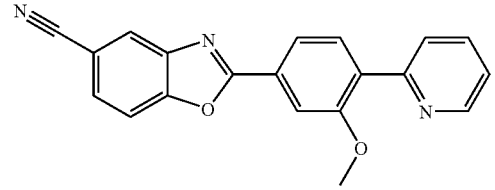

To 1 mL of degassed DMF was added 5-bromo-2-(3-methoxy-4-pyridin-2-ylphenyl)-1,3-benzoxazole (622 mg, 1.63 mmol), zinc cyanide (115 mg, 0.98 mmol), tris(dibenzylideneacetone)-dipalladium (0)-chloroform complex (30 mg, 0.029 mmol), and 1,1'-bisdiphenylphosphinoferrocene (41 mg, 0.073 mmol). The reaction mixture was degassed with argon for an additional 10 min and heated at 120° C. under an argon atmosphere for 20 h. The mixture was cooled to 80° C., 4 mL of a 4:1:4 saturated NH$_4$Cl:NH$_4$OH:H$_2$O solution was added dropwise, and the mixture cooled to rt and stirred overnight. The mixture was cooled to −9° C. and filtered, the solid washed with 5 mL of a 4:1:5 sat. NH$_4$Cl: NH$_4$OH:H$_2$O solution followed by 5 mL H$_2$O, and dried under vacuum to a dark yellow solid. The crude solid was purified by column chromatography (20–80% EtOAc/hexanes) to give 5-cyano-2-(3-methoxy-4-pyridin-2-ylphenyl)-1,3-benzoxazole as a tan solid. $^1$H NMR (DMSO-$d_6$, 300 MHz) δ 8.72 (d, 1H), 8.47 (d, 1H), 8.09–7.85 (m, 7H), 7.40 (ddd, 1H), 4.01 (s, 3H); MS (ESI) 328 (M+H)$^+$.

EXAMPLE 62

5-Chloro-2-(3-methoxy-4-pyridin-2-ylphenyl)-1,3-benzoxazole hydrochloride

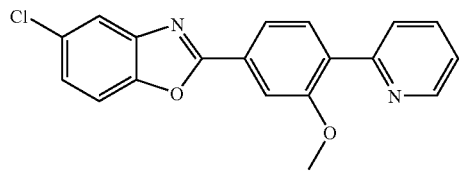

To a suspension of 4-amino-3-methoxy benzoic acid (21 g, 0.125 mole) in H$_2$SO$_4$ (2M, 100 mL) was added dropwise aqueous sodium nitrite (9.54 g, 0.138 mole) at 5° C. The mixture was stirred an additional 10 min at this temperature. Aqueous potassium iodide (22.9 g, 0.138 mole) was added dropwise. The solution was warmed at 40° C. until end of the gas evolution. The reaction mixture was cooled at rt and EtOAc (150 mL) was added. The aqueous layer was extracted two with EtOAc (2×150 mL). The organic layers were combined and washed with a 5% solution of sodium thiosulfate (200 mL), brine (200 mL), dried (MgSO$_4$) and concentrated under vacuum to give a yellow solid. The crude material was dissolved in MeOH ((400 mL), H$_2$SO$_4$ was added (8 mL) and the reaction was heated under reflux overnight. After classical work-up the crude material was purified by flash chromatography using a mixture of hexane and ethyl acetate (80/20) as eluant to give 22.2 g of pure 4-iodo-3-methoxy-methylbenzoate (0.076 mole, 60.8%). A mixture of 4-iodo-3-methoxy-methylbenzoate (7 g, 24 mmol), 2-pyridyl zinc bromide (0.5M in THF, 62 mL, 31.2 mmol), and tetrakis(triphenylphosphine)palladium (1.4 g, 1.2 mmol) in THF (40 mL) was refluxed for 5 h and then stirred at rt overnight. $H_2O$ was added and the solution was filtered through Celite, the pad was washed with EtOAc, and the two layers were separated. The aqueous was washed with EtOAc (2×50 mL), dried over $Na_2SO_4$, and evaporated to dryness. The dark residue was purified by flash chromatography on silica gel eluting with EtOAc:hexane (1:5) to afford the desired intermediate, methyl-3-methoxy-4-pyridin-2-yl benzoate, as a yellow solid.

Methyl-3-methoxy-4-pyridin-2-yl benzoate (4.70 g, 19.3 mmol) and 10% lithium hydroxide in 1:1 water: methanol (14.8 mL) was heated to reflux conditions until no starting material was observed by TLC. 6N HCl aqueous solution was added to the cooled mixture until pH 5, A yellow solid precipated was filtered to give the desired intermediate, 3-methoxy-4-pyridin-2-yl benzoic acid, as a grey solid.

3-Methoxy-4-pyridin-2-yl benzoic acid (500 mg, 2.2 mmol), 2-amino-4-chlorophenol (620 mg, 4.3 mmol) and trimethyl silylpolyphosphate (2 mL) was heated to 180° C. overnight under argon. To the cooled reaction mixture, water (100 mL) was added and extracted with EtOAc (4×20 mL). Set aside organic layer. Filtered aqueous layer through Celite pad and basified filtrate to pH 9 (solid $NaHCO_3$). Extracted with EtOAc (2×30 mL), combined all organic layers and concentrated in vacuo. The resulting orange oil was purified by flash chromatography using a gradient elution of 15:85 ethyl acetate:hexane to 1:1 ethyl acetate:hexane to give the desired intermediate, 5-chloro-2-(3-methoxy-4-pyridin-2-ylphenyl)-1,3-benzoxazole as a colorless solid.

5-Chloro-2-(3-methoxy-4-pyridin-2-ylphenyl)-1,3-benzoxazole (26 mg) was stirred in dichloromethane. 1.0M HCl in diethyl ether (0.95 mL) was added and allowed reaction mixture to stir for 30 minutes. Concentration of reaction mixture in vacuo gave the desired compound, 5-chloro-2-(3-methoxy-4-pyridin-2-yl phenyl)-1,3-benzoxazole hydrochloride, as a pink solid. $^1H$ NMR ($CD_3OD$, 300 MHz) δ 8.88–7.46 (m, 10H), 4.11 (s, 3H). MS (ESI) 337 $(M+H)^+$.

EXAMPLE 63

2-(3-Methoxy-4-pyridin-2-ylphenyl)-5-methyl-1,3-benzoxazole

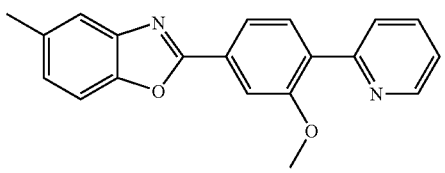

A mixture of A mixture of 4-iodo-3-methoxy-methylbenzoate (see example 62) (7 g, 24 mmol), 2-pyridyl zinc bromide (0.5M in THF, 62 mL, 31.2 mmol), and tetrakis(triphenylphosphine)palladium (1.4 g, 1.2 mmol) in THF (40 mL) was refluxed for 5 h and then stirred at rt overnight. $H_2O$ was added and the solution was filtered through Celite, the pad was washed with EtOAc, and the two layers were separated. The aqueous was washed with EtOAc (2×50 mL), dried over $Na_2SO_4$, and evaporated to dryness. The dark residue was purified by flash chromatography on silica gel eluting with EtOAc:hexane (1:5) to afford the desired intermediate, methyl-3-methoxy-4-pyridin-2-yl benzoate, as a yellow solid.

Methyl-3-methoxy-4-pyridin-2-yl benzoate (4.70 g, 19.3 mmol) and 10% lithium hydroxide in 1:1 water:methanol (14.8 mL) was heated to reflux conditions until no starting material was observed by TLC. 6N HCl aqueous solution was added to the cooled mixture until pH 5, A yellow solid precipated out of solution and was filtered to give the desired intermediate, 3-methoxy-4-pyridin-2-yl benzoic acid, as a grey solid.

3-Methoxy-4-pyridin-2-yl benzoic acid (490 mg, 2.1 mmol), 2-amino-p-cresol (527 mg, 4.28 mmol) and trimethylsilyl polyphosphate (2 mL) was refluxed overnight under argon. Added water (100 mL) to the cooled reaction mixture and basified to pH 8 (solid $NaHCO_3$). Extracted with EtOAc (3×60 mL), dried ($Na_2SO_4$) and concentrated in vacuo. The resulting yellow residue was purified by flash chromatography using a gradient elution of 1:9 EtOAc:hexanes to 1:4 EtOAc:hexanes to give the desired compound, 2-(3-methoxy-4-pyridin-2-ylphenyl)-5-methyl-1,3-benzoxazole, as a yellow solid. $^1H$ NMR ($CDCl_3$, 300 MHz) δ 8.74 (m, 1H), 7.98–7.16 (m, 10H), 4.03 (s, 3H), 2.51 (s, 3H). (ESI) 317 $(M+H)^+$.

EXAMPLE 64

2-(3-Methoxy-4-pyridin-2-ylphenyl)[1,3]oxazolo[4,5-b]pyridine

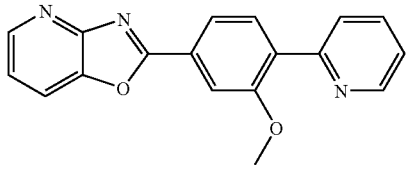

To 5 mL of trimethylsilyl polyphosphate was added 2-aminopyridin-3-ol (175 mg, 1.59 mmol) and 3-methoxy-4-pyridin-2-ylbenzoic acid (344 mg, 1.50 mmol). The mixture was heated at 200° C. for 2 h, quenched over ice, and made basic (pH 14) with 1N NaOH. The aqueous phase was extracted with MTBE (3×200 mL). The combined organic layers were washed with brine, dried over $MgSO_4$, filtered, and concentrated in vacuo to give 2-(3-methoxy-4-pyridin-2-ylphenyl)[1,3]oxazolo[4,5-b]pyridine as a light yellow solid. $^1H$ NMR (DMSO-$d_6$, 300 MHz) δ 8.72 (d, 1H), 8.58 (d, 1H), 8.30 (d, 1H), 8.05–7.91 (m, 4H), 7.88 (t, 1H), 7.51 (dd, 1H), 7.40 (dd, 1H), 4.02 (s, 3H); MS (ESI) 304 $(M+H)^+$.

EXAMPLE 65

2-(3-Methoxy-4-pyridin-2-ylphenyl)[1,3]oxazolo[4,5-c]pyridine

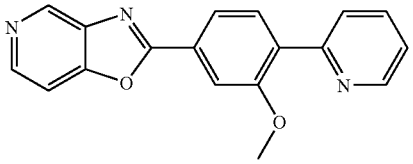

To a stirred solution of 3-aminopyridine (9.41 g, 100 mmol) and triethylamine (16.7 mL, 120 mmol) in $CH_2Cl_2$ (300 mL) at 0° C. was added trimethylacetyl chloride (14.8 mL, 120 mmol) dropwise over 15 min. The reaction was warmed to rt and stirred overnight. The mixture was concentrated in vacuo, the residue partitioned between EtOAc and H$_2$O, and the layers separated. The aqueous layer was made basic with saturated NaHCO$_3$ and extracted with EtOAc. The combined organic layers were washed with saturated NaHCO$_3$ and brine, dried over MgSO$_4$, filtered, and concentrated in vacuo to give N-(pyridin-3-yl)-2,2-dimethylpropanamide as a tan solid. $^1$H NMR (CDCl$_3$, 300 MHz) δ 8.57 (d, 1H), 8.33 (dd, 1H), 8.17 (ddd, 1H), 7.69 (br s, 1H), 7.27 (dd, 1H), 1.33 (s, 9H).

To a stirred solution of N-(pyridin-3-yl)-2,2-dimethylpropanamide (8.90 g, 50.0 mmol) in THF (200 mL) at −78° C. was added n-Butyllithium (50 mL, 125 mmol) dropwise over 30 min. After addition, the reaction mixture was warmed to 0° C. and stirred an additional 3 h. The reaction was then cooled back to −78° C. and trimethyl borate (14.2 mL, 125 mmol) in THF was added dropwise over 15 min. After addition, the reaction mixture was warmed to 0° C. and stirred an additional 2 h. Glacial AcOH (10.8 mL, 188 mmol) was added to the reaction, followed by dropwise addition of 30% H$_2$O$_2$ (14.3 mL, 138 mmol). The reaction mixture was warmed to rt and stirred overnight. The mixture was diluted with H$_2$O and concentrated in vacuo. The residue was extracted three times with 10% iPrOH/CHCl$_3$, the combined extracts treated with activated charcoal, and the slurry filtered through Celite. The organic layer was washed three times with H$_2$O, once with brine, dried over MgSO$_4$, filtered, and concentrated in vacuo. The residue was purified by column chromatography (3–10% MeOH/CHCl$_3$) to give N-(4-hydroxypyridin-3-yl)-2,2-dimethylpropanamide as a light yellow solid. $^1$H NMR (DMSO-d$_6$, 300 MHz) δ 11.58 (br s, 1H), 8.76 (br s, 1H), 8.67 (s, 1H), 7.68 (d, 1H), 6.26 (d, 1H), 1.22 (s, 9H).

To a stirring solution of 3N HCl (50 mL, 150 mmol) was added N-(4-hydroxypyridin-3-yl)-2,2-dimethylpropanamide (1.94 g, 10.0 mmol). The mixture was heated at reflux overnight. After cooling to rt, the mixture was neutralized with 5N NaOH and concentrated in vacuo. The residue was taken up in MeOH, the salts filtered out, and the organic layer reconcentrated. The resulting residue was taken up in EtOH, the salts filtered out, and the organic layer reconcentrated to give 3-aminopyridin-4-ol, which was taken into the next step without purification. $^1$H NMR (DMSO-d$_6$, 300 MHz) δ 12.25 (br s, 1H), 7.35 (dd, 1H), 7.18 (d, 1H), 6.00 (d, 1H), 4.54 (br s, 2H).

To 7 mL trimethylsilyl polyphosphate was added 3-aminopyridin-4-ol (330 mg, 3.00 mmol) and 3-methoxy-4-pyridin-2-ylbenzoic acid (460 mg, 2.00 mmol). The mixture was heated at 200° C. for 2 h, quenched over ice, and made basic (pH 14) with 1N NaOH. The aqueous phase was extracted with MTBE (3×200 mL). The combined organic layers were washed with brine, dried over MgSO$_4$, filtered, concentrated in vacuo, and purified by column chromatography (50–100% EtOAc/hexanes followed by 10% MeOH/CHCl$_3$) to give 2-(3-Methoxy-4-pyridin-2-ylphenyl)[1,3]oxazolo[4,5-c]pyridine as a yellow solid. $^1$H NMR (DMSO-d$_6$, 300 MHz) δ 9.16 (s, 1H), 8.71 (d, 1H), 8.62 (d, 1H), 8.03–7.84 (m, 6H), 7.39 (t, 1H), 4.00 (s, 3H); MS (ESI) 304 (M+H)$^+$.

EXAMPLE 66

2-(3-Methoxy-4-pyridin-2-ylphenyl)[1,3]oxazolo[5,4-b]pyridine

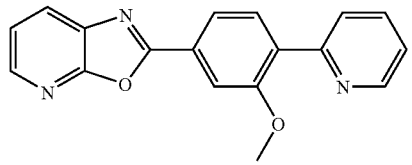

To a stirred slurry of 10% palladium on carbon (1.08 g, 1.02 mmol) in MeOH (100 mL) was added 3-nitropyridin-2-ol (1.42 g, 10.2 mmol). The reaction mixture was stirred under an H$_2$ atmosphere until significant reduction was seen by TLC. The mixture was filtered through Celite and concentrated in vacuo. The resultant semisolid was triturated with hexanes and concentrated to remove residual MeOH and purified by UV Prep to give 3-aminopyridin-2-ol as a dark brown oil.

To 5 mL of trimethylsilyl polyphosphate was added 3-aminopyridin-2-ol (150 mg, 1.59 mmol) and 3-methoxy-4-pyridin-2-ylbenzoic acid (229 mg, 1.0 mmol). The mixture was heated at 200° C. for 2 h, quenched over ice, and made basic (pH 14) with 1N NaOH. The aqueous phase was extracted with EtOAc (3×200 mL). The combined organic layers were washed with brine, dried over MgSO$_4$, filtered, and concentrated in vacuo. The resultant oil was taken up in a minimum of EtOAc and purified by prep TLC (1:1 EtOAc/hexanes) to give 2-(3-methoxy-4-pyridin-2-ylphenyl)[1,3]oxazolo[5,4-b]pyridine as a light yellow solid. $^1$H NMR (DMSO-d$_6$, 300 MHz) δ 8.73 (dq, 1H), 8.43 (dd, 1H), 8.32 (dd, 1H), 8.02 (d, 1H), 7.99–7.93 (m, 2H), 7.92–7.85 (m, 2H), 7.55 (dd, 1H), 7.40 (ddd, 1H), 4.01 (s, 3H); MS (ESI) 304 (M+H)$^+$.

EXAMPLE 67

2-[4-(6-Bromopyridin-2-yl)-3-methoxyphenyl]-1,3-benzoxazole

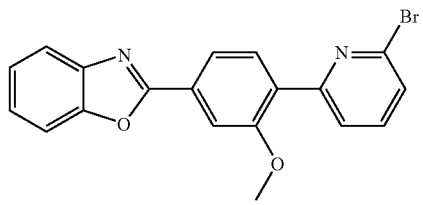

4-hydroxy-3-methoxybenzoic acid (25 g, 150 mmol) and 2-amino phenol (16 g, 150 mmol) were combined in a round bottom flask. Trimethylsilyl polyphosphate (80 mL) was added. The mixture was heated at 180° C. for 30 min. The mixture was poured over ice and allowed to stir overnight. The suspension was filtered to afford 4-(1,3-benzoxazol-2-yl)-2-methoxyphenol as a pale green solid. MS (ESI) 242 (M+H).

A solution of 4-(1,3-benzoxazol-2-yl)-2-methoxyphenol (7.1 g, 29 mmol) in anhydrous DMF (100 mL) was treated with Cs$_2$CO$_3$ (9.6 g, 29 mmol) and N-phenyl trifluoromethanesulfonimide (10 g, 29 mmol) at 22° C. for 30 min. The resulting mixture was quenched with saturated aqueous NaHCO₃ (50 mL) and diluted with EtOAc (500 mL). The EtOAc solution was washed with brine (3×100 mL), dried (MgSO₄), filtered and concentrated iii vacuo. Crude mixture was adsorbed onto silica gel and purified by automated flash chromatography using and EtOAc/hexanes gradient to afford 4-(1,3-benzoxazol-2-yl)-2-methoxyphenyl trifluoromethanesulfonate as a colorless oil: MS (ESI) 374 (M+H)⁺.

4-(1,3-benzoxazol-2-yl)-2-methoxyphenyl trifluoromethanesulfonate (480 mg, 1.3 mmol), potassium acetate (380 mg, 3.8 mmol), bis(diphenylphosphino)ferrocene palladium dichloride (100 mg, 0.13 mmol), and bis(pinacolato) diboron (390 mg, 1.5 mmol) were combined in a 2-neck flask. The flask was evacuated and filled with argon and dioxane (10 mL) was added. The suspension was deoxygenated with a stream of argon for 10 min. The reaction mixture was stirred under argon at 80° C. for 24 h. Crude mixture was adsorbed onto silica gel and purified by automated flash chromatography using and EtOAc/hexanes gradient to afford 2-[3-methoxy-4-(4,4,5,5-tetramethyl-1,3,2-dioxaborolan-2-yl)phenyl]-1,3-benzoxazole as an orange solid: ¹H NMR (CDCl₃, 300 MHz) δ 7.83–7.83 (m, 3H), 7.74 (s, 1H), 7.62–7.55 (m, 1H), 7.39–7.36 (m, 2H), 3.98 (s, 3H), 1.39 (s, 12H).

2-[3-methoxy-4-(4,4,5,5-tetramethyl-1,3,2-dioxaborolan-2-yl)phenyl]-1,3-benzoxazole (200 mg, 0.57 mmol) CsF (350 mg, 2.3 mmol), Pd(Ph₃P)₄ (65 mg, 0.057 mmol), and 2-bromopyridine (140 mg, 0.57 mmol) were combined in a 2-neck flask. The flask was evacuated and filled with argon and DME (5 mL) was added. The suspension was deoxygenated with a stream of argon for 10 min. The reaction mixture was stirred under argon at 80° C. for 24 h. Crude mixture was adsorbed onto silica gel and purified by automated flash chromatography using and EtOAc/hexanes gradient to afford the desired 2-[4-(6-bromopyridin-2-yl)-3-methoxyphenyl]-1,3-benzoxazole as a colorless solid: ¹H NMR (CDCl₃, 300 MHz) δ 8.08–8.05 (d, 1H), 7.98–7.95 (m, 2H), 7.89 (s, 1H), 7.84–7.79 (m, 1H), 7.63–7.60 (m, 1H), 7.45–7.38 (m, 3H), 4.02 (s, 3H). MS (ESI) 382 (M+H)⁺.

EXAMPLE 68

2-[3-Methoxy-4-(6-methylpyridin-2-yl)phenyl]-1,3-benzoxazole

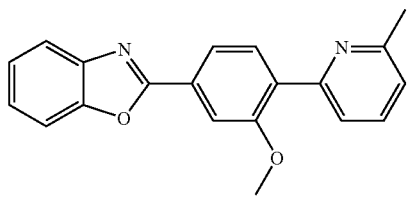

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (200 mg, 0.57 mmol) was reacted with 2-bromo-6-methylpyridine (65 μL, 0.57 mmol) to afford the desired 2-[3-methoxy-4-(6-methylpyridin-2-yl)phenyl]-1,3-benzoxazole as a colorless solid: ¹H NMR (CDCl₃, 300 MHz) δ 7.96–7.95 (m, 2H), 7.89 (s, 1H), 7.82–7.79 (m, 1H), 7.67–7.60 (m, 3H), 7.39–7.36 (m, 2H), 7.14–7.12 (m, 1H), 4.00 (s, 3H), 2.65 (s, 3H). MS (ESI) 317 (M+H)⁺.

EXAMPLE 69

2-[3-Methoxy-4-(6-methoxypyridin-2-yl)phenyl]-1,3-benzoxazole

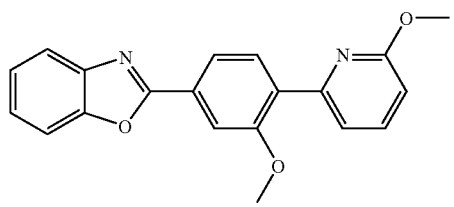

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (200 mg, 0.57 mmol) was reacted with 2-bromo-6-methoxypyridine (65 μL, 0.57 mmol) to afford the desired 2-[3-methoxy-4-(6-methoxypyridin-2-yl)phenyl]-1,3-benzoxazole as a colorless solid: ¹H NMR (CDCl₃, 300 MHz) δ 7.96–7.95 (m, 2H), 7.89 (s, 1H), 7.82–7.79 (m, 1H), 7.67–7.60 (m, 3H), 7.39–7.36 (m, 2H), 7.14–7.12 (m, 1H), 4.00 (s, 3H), 2.65 (s, 3H). MS (ESI) 333 (M+H)⁺.

EXAMPLE 70

2-[4-(5-Chloropyridin-2-yl)-3-methoxyphenyl]-1,3-benzoxazole

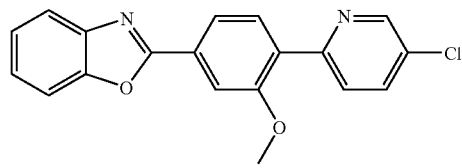

A solution of 5-chloro-2-pyridinol (3.0 g, 23 mmol), N-phenyl trifluoromethanesulfonimide (8.3 g, 23 mmol), and Cs₂CO₃ (7.5 g, 23 mmol) in CH₃CN (100 mL) was stirred at room temp for 24 h. Crude mixture was adsorbed onto silica gel and purified by automated flash chromatography using an EtOAc/hexanes gradient to afford 4-chlorophenyl-2-trifluoromethanesulfonate as an orange oil: MS (ESI) 262 (M+H)⁺.

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (100 mg, 0.28 mmol) was reacted with 4-chlorophenyl trifluoromethanesulfonate (74 mg, 0.28 mmol) to afford the desired 2-[4-(5-chloropyridin-2-yl)-3-methoxyphenyl]-1,3-benzoxazole as a colorless solid: ¹H NMR (CDCl₃, 300 MHz) δ 8.69–8.68 (d, 1H), 7.98 (s, 2H), 7.94–7.90 (m, 2H), 7.86–7.78 (m, 1H), 7.74–7.73 (m, 1H), 7.65–7.58 (m, 1H), 7.40–7.37 (m, 2H), 4.03 (s, 3H). MS (ESI) 337 (M+H)⁺.

EXAMPLE 71

2-[3-Methoxy-4-(3-methylpyridin-2-yl)phenyl]-1,3-benzoxazole

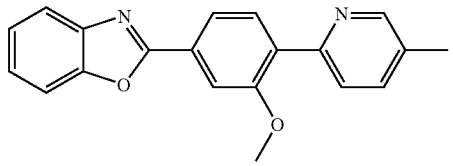

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (150 mg, 0.43 mmol) was reacted with 2-bromo-5-methylpyridine (73 mg, 0.43 mmol) to afford the desired 2-[3-methoxy-4-(3-methylpyridin-2-yl)phenyl]-1,3-benzoxazole as a colorless solid: $^1$H NMR (CDCl$_3$, 300 MHz) δ 8.60–8.58 (d, 1H), 7.96–7.90 (m, 3H), 7.80–7.79 (m, 1H), 7.70 (s, 1H), 7.62–7.60 (m, 1H), 7.39–7.36 (m, 2H), 7.10–7.08 (m, 1H), 4.01(s, 3H), 2.43 (s, 3H). MS (ESI) 317 (M+H)$^+$.

EXAMPLE 72

2-[3-Methoxy-4-(4-methylpyridin-2-yl)phenyl]-1,3-benzoxazole

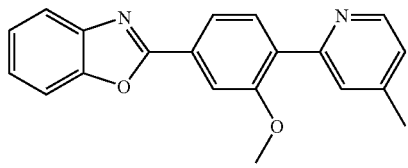

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (150 mg, 0.43 mmol) was reacted with 2-bromo-4-methylpyridine (47 μL, 0.43 mmol) to afford the desired 2-[3-methoxy-4-(4-methylpyridin-2-yl)phenyl]-1,3-benzoxazole as a colorless solid: $^1$H NMR (CDCl$_3$, 300 MHz) δ 8.57 (s, 1H), 7.97–7.96 (m, 2H), 7.89 (s, 1H), 7.82–7.79 (m, 2H), 7.63–7.54 (m, 2H), 7.39–7.36 (m, 2H), 4.01 (s, 3H), 2.39 (s, 3H). MS (ESI) 317 (M+H)$^+$.

EXAMPLE 73

2-[3-Methoxy-4-(5-methylpyridin-2-yl)phenyl]-1,3-benzoxazole

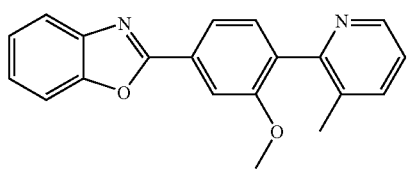

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (200 mg, 0.57 mmol) was reacted with 2-bromo-3-methylpyridine (63 μL, 0.57 mmol) to afford the desired 2-[3-methoxy-4-(5-methylpyridin-2-yl)phenyl]-1,3-benzoxazole as a colorless solid: $^1$H NMR (CDCl$_3$, 300 MHz) δ 8.55–8.53 (d, 1H), 7.98–7.95 (m, 1H), 7.88 (s, 1H), 7.81–7.78 (m, 1H), 7.61–7.56 (m, 2H), 7.46–7.44 (d, 1H), 7.39–7.35 (m, 2H), 7.23–7.19 (m, 1H), 3.91 (s, 3H), 2.19 (s, 3H). MS (ESI) 317 (M+H)$^+$.

EXAMPLE 74

2-[4-(6-Fluoropyridin-3-yl)-3-methoxyphenyl]-1,3-benzoxazole

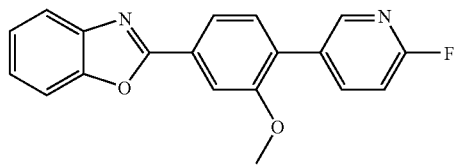

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (200 mg, 0.57 mmol) was reacted with 5-bromo-2-fluoropyridine (59 μL, 0.57 mmol) to afford the desired 2-[4-(6-fluoropyridin-3-yl)-3-methoxyphenyl]-1,3-benzoxazole as a colorless solid: $^1$H NMR (CDCl$_3$, 300 MHz) δ 8.42 (s, 1H), 8.07–8.00 (m, 1H), 7.97–7.94 (m, 1H), 7.89 (s, 1H), 7.82–7.79 (m, 1H), 7.64–7.59(m, 1H), 7.48–7.45 (d, 1H), 7.41–7.38 (m, 1H), 7.03–6.99 (m, 1H), 3.98 (s, 3H). MS (ESI) 321 (M+H)$^+$.

EXAMPLE 75

2-[4-(6-Chloropyridin-3-yl)-3-methoxyphenyl]-1,3-benzoxazole

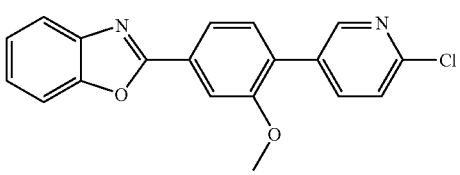

Utilizing the general procedure outlined in the synthesis of 2-[4-(6-bromopyridin-2-yl)-3-methoxyphenyl]-1,3-benzoxazole, 2-[3-methoxy-4-(4,4,5,5-tetramethyl-1,3,2-dioxaborolan-2-yl)phenyl]-1,3-benzoxazole (100 mg, 0.29 mmol) was reacted with 5-bromo-2-chloropyridine (55 mg, 0.29 mmol) and Na$_2$CO$_3$ (90 mg, 0.86 mmol) in DME (2 mL), and H$_2$O (2 mL) to afford the desired 2-[4-(6-chloropyridin-3-yl)-3-methoxyphenyl]-1,3-benzoxazole as a colorless solid: $^1$H NMR (CDCl$_3$, 300 MHz) δ 8.59 (d, 1H), 7.85–7.66 (m, 3H), 7.44–7.78 (m, 1H), 7.56–7.60 (m, 1H), 7.48–7.45 (d, 1H), 7.42–7.38 (m, 3H), 3.98 (s, 3H). MS (ESI) 337 (M+H)$^+$.

EXAMPLE 76

2-[3-Methoxy-4-(6-morpholin-4-ylpyridin-2-yl)phenyl]-1,3-benzoxazole

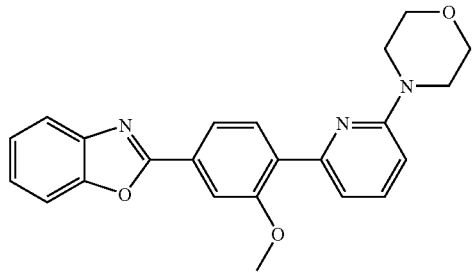

2-[4-(6-bromopyridin-2-yl)-3-methoxyphenyl]-1,3-benzoxazole (150 mg, 0.39 mmol), morpholine (41 μL, 0.47 mmol), Pd$_2$(dba)$_3$ (8.2 mg, 0.0078 mmol), BINAP (9.8 mg, 0.016 mmol), and NaOtBu (53 mg, 0.55 mmol) were combined in a sealable tube evacuated and backfilled with argon. Toluene (4 mL) was added and the mixture was degassed with a stream of argon for 5 min. The tube was sealed and the mixture was heated to 70° C. for 18 h. Crude mixture was adsorbed onto silica gel and purified by automated flash chromatography using an EtOAc/hexanes gradient to afford the desired 2-[3-methoxy-4-(6-morpholin-4-ylpyridin-2-yl)phenyl]-1,3-benzoxazole as an orange solid: $^1$H NMR (CDCl$_3$, 300 MHz) δ 8.07–8.05 (d, 1H), 7.96–7.95 (m, 1H), 7.88 (s, 1H), 7.83–7.78 (m, 1H), 7.65–7.58 (m, 2H), 7.42–7.36 (m, 3H), 6.65–6.62 (d, 1H), 4.02 (s, 3H), 3.88–3.85 (t, 4H), 3.61–3.58 (t, 4H). MS (ESI) 388 (M+H)$^+$.

EXAMPLE 77

2-[3-Methoxy-4-(5-morpholin-4-ylpyridin-2-yl)phenyl]-1,3-benzoxazole

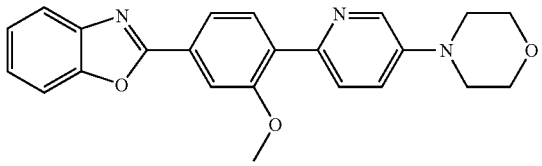

2-[4-(5-chloropyridin-2-yl)-3-methoxyphenyl]-1,3-benzoxazole (58 mg, 0.17 mmol), morpholine (18 μL, 0.21 mmol), Pd(OAc)$_2$ (0.38 mg, 0.0017 mmol), 1,1'-biphenyl-2-yl[di(tert-butyl)]phosphine (1.0 mg, 0.0034 mmol), and NaOtBu (23 mg, 0.24 mmol) were combined in a sealable tube evacuated and backfilled with argon. Toluene (800 μL) was added and the mixture was degassed with a stream of argon for 5 min. The tube was sealed and the mixture was heated to 110° C. for 18 h. Crude mixture was adsorbed onto silica gel and purified by automated flash chromatography using an EtOAc/hexanes gradient to afford 2-[3-methoxy-4-(5-morpholin-4-ylpyridin-2-yl)phenyl]-1,3-benzoxazole as a yellow solid. The freebase was dissolved in Et$_2$O/CH$_2$Cl$_2$ and treated with 1N HCl in Et$_2$O. Resulting yellow solid was filtered and dried under high vacuum to afford the desired 2-[3-methoxy-4-(5-morpholin-4-ylpyridin-2-yl)phenyl]-1,3-benzoxazole hydrochloride as a yellow solid: $^1$H NMR (CD$_3$OD, 300 MHz) δ 8.33–8.30 (d, 1H), 8.20–8.09 (m, 2H), 8.08–8.02 (m, 2H), 7.87–7.77 (m, 2H), 7.75–7.71 (m, 1H), 7.53–7.42 (m, 2H), 4.10 (s, 3H), 3.89 (t, 4H), 3.49–3.47 (t, 4H). MS (ESI) 388 (M+H)$^+$.

EXAMPLE 78

6-[4-(1,3-Benzoxazol-2-yl)-2-methoxyphenyl]pyridin-3-amine

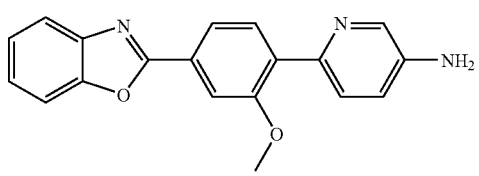

2-[4-(5-chloropyridin-2-yl)-3-methoxyphenyl]-1,3-benzoxazole (100 mg, 0.30 mmol), benzophenone imine (60 μL, 0.36 mmol), Pd$_2$(dba)$_3$ (15 mg, 0.015 mmol), 1,1'-biphenyl-2-yl(dicyclohexyl)phosphine (10 mg, 0.015 mmol), NaOtBu (40 mg, 0.42 mmol) were combined in a sealable tube evacuated and backfilled with argon. Toluene (600 μL) was added and the mixture was degassed with a stream of argon for 5 min. The tube was sealed and the mixture was heated to 80° C. for 24 h. Crude mixture was adsorbed onto silica gel and purified by automated flash chromatography using an EtOAc/hexanes gradient to afford 6-[4-(1,3-benzoxazol-2-yl)-2-methoxyphenyl]-N-(diphenylmethylene)pyridin-3-amine as a yellow solid.

6-[4-(1,3-benzoxazol-2-yl)-2-methoxyphenyl]-N-(diphenylmethylene)pyridin-3-amine (61 mg, 0.13 mmol) was dissolved in MeOH (2 mL) and NaOAc (25 mg, 0.31 mmol) and hydroxylamine hydrochloride (16 mg, 0.23 mmol) were added. The resulting suspension was stirred at rt for 1 h. The mixture was partitioned between CH$_2$Cl$_2$ and 0.1N aqueous NaOH. Aqueous layer was extracted with CH$_2$Cl$_2$ (3×15 mL). The combined organic layers were dried over MgSO$_4$, filtered and concentrated. Crude mixture was adsorbed onto silica gel and purified by automated flash chromatography using an EtOAc/hexanes gradient to afford the desired 6-[4-(1,3-benzoxazol-2-yl)-2-methoxyphenyl]pyridin-3-amine: $^1$H NMR (CDCl$_3$, 300 MHz) δ 8.25–8.24 (d, 1H), 7.95 (s, 2H), 7.86 (s, 1H), 7.80–7.76 (m, 2H), 7.62–7.59 (m, 1H), 7.38–7.35 (m, 2H), 7.07–7.04 (m, 1H), 4.01 (s, 3H). MS (ESI) 318 (M+H)$^+$.

EXAMPLE 79

6-[4-(1,3-Benzoxazol-2-yl)-2-methoxyphenyl]-N,N-dimethylpyridin-3-amine

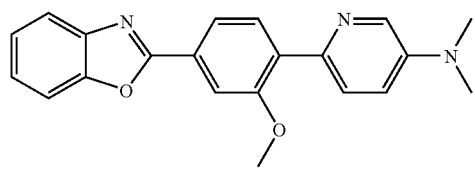

6-[4-(1,3-benzoxazol-2-yl)-2-methoxyphenyl]pyridin-3-amine (22 mg, 0.070 mmol) was dissolved in MeOH (2 mL), and AcOH (2 drops). NaCNBH$_3$ (44 mg, 0.70 mmol) and formaldehyde (50 μL, 0.70 mmol) were added and the mixture was stirred overnight. The mixture was partitioned between CH$_2$Cl$_2$ and dilute brine. The aqueous layer was extracted with CH$_2$Cl$_2$ (3×15 mL). The combined organic layers were dried over MgSO$_4$, filtered and concentrated. The crude mixture was adsorbed onto silica gel and purified by automated flash chromatography using an EtOAc/hexanes gradient to afford the desired 6-[4-(1,3-benzoxazol-2-yl)-2-methoxyphenyl]-N,N-dimethylpyridin-3-amine: $^1$H NMR (CDCl$_3$, 300 MHz) δ 8.24–8.23 (d, 1H), 7.94 (s, 2H), 7.87 (s, 1H), 7.84–7.79 (m, 2H), 7.59 (m, 1H), 7.38–7.35 (m, 2H), 7.07–7.06 (m, 1H), 4.01 (s, 3H), 3.04 (s, 6H). MS (ESI) 346 (M+H)$^+$.

EXAMPLE 80

[2-methoxy-4-(4,5,6,7-tetrahydro-1,3-benzoxazol-2-yl)phenyl]acetonitrile

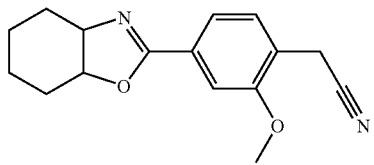

To a solution of methyl 4-(bromoethyl)-3-methoxy benzoate (25 g, 96.5 mmol) in acetonitrile (200 mL) was added TMSCN (19 mL, 144.7 mmol) and TBAF (144 mL, 1.0M in THF) at 22° C. 20 min later, the resulting reaction mixture was concentrated under reduced pressure to give after purification by flash chromatography (silica gel, 4:1; hexanes: EtOAc) the to give methyl 4-(cyanomethyl)-3-ethoxybenzoate as a white solid. MS (ESI) 206 (M+H)$^+$.

A solution of methyl 4-(cyanomethyl)-3-ethoxybenzoate (18 g, 88 mmol) in 150 mL of MeOH:THF:H$_2$O (3:3:1) was treated with lithium hydroxide monohydrate (11 g, 263 mmol) at 22° C. for overnight. Then 10% aqueous HCl (100 mL) was added to quench the reaction, the mixture was extracted with EtOAc (3×200 mL), the combined organic extracts were washed with brine (100 mL) and dried (MgSO$_4$), filtered and concentrated in vacuo to afford 4-(cyanomethyl)-3-methoxybenzoic acid as a white solid. MS (ESI) 192 (M+H)$^+$.

The 4-(cyanomethyl)-3-methoxybenzoic acid (0.33 g, 1.7 mmol) was suspended in anhydrous dichloromethane (5 mL) and treated with oxalyl chloride (0.3 mL, 3.5 mmol) followed by few drops of DMF at 22° C. under argon. After 2 h stirring, the resulting solution was concentrated to dryness, dissolved in dichloromethane (5 mL), and added slowly to a solution of trans-2-aminocyclohexanol hydrochloride (0.26 g, 1.7 mmol) and TEA (0.5 mL, 3.5 mmol) in anhydrous dichloromethane (10 mL). After 20 min stirring, filtered off salt, and concentrated to afford 4-(cyanomethyl)-N-[(2R)-2-hydroxycyclohexyl]-3-methoxybenzamide as a yellow solid. MS (ESI) 289 (M+H)$^+$.

To a solution of oxalyl chloride (0.2 mL, 2.2 mmol) in anhydrous dichloromethane (2 mL) at −78° C. was added DMSO (0.32 mL, 4.5 mmol) under Argon. The solution was maintained for 10 min where upon a solution of 4-(cyanomethyl)-N-[(2R)-2-hydroxycyclohexyl]-3-methoxybenzamide (430 mg, 1.5 mmol) in anhydrous dichloromethane (13 mL) was added dropwide. The reaction was stirred at −78° C. for 30 min, whereupon TEA (1 mL, 7.5 mmol) was added. The reaction was warmed to 22° C. for 2 h. Then, 50 mL dichloromethane was added to the mixture, washed with sat. NaHCO$_3$ (3×15 mL) and sat. brine (3×15 mL), dried (MgSO$_4$), and concentrated to afford a yellow solid of 4-(cyanomethyl)-3-methoxy-N-(2-oxocyclohexyl)benzamide. MS (ESI) 287 (M+H)$^+$.

4-(cyanomethyl)-3-methoxy-N-(2-oxocyclohexyl)benzamide (0.8 g, 2.8 mmol) was treated with POCl$_3$ (5 mL) at reflux for 1 h. The resulting mixture was concentrated and dissolved in dichloromethane (50 mL), washed with sat. NaHCO$_3$ (3×15 mL) and sat. brine (3×15 mL), dried (MgSO$_4$), and concentrated in vacuo. The crude residue was chromatographed on silica gel, eluting with 2:1 hexanes: EtOAc to afford the desired compound, [2-methoxy-4-(4,5,6,7-tetrahydro-1,3-benzoxazol-2-yl)phenyl]acetonitrile, the desired compound, as white solid. $^1$H NMR (CDCl$_3$, 300 MHz) δ 7.58 (dd, 1H), 7.53 (m, 1H), 7.42 (d, 1H), 3.95 (s, 3H), 3.72 (s, 2H), 2.71 (m, 2H), 2.62 (m, 2H), 1.87 (m, 4H). MS (ESI) 269 (M+H)$^+$.

What is claimed is:

1. A compound represented by Formula (I):

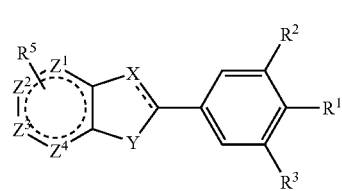

or a pharmaceutically acceptable salt thereof, wherein

X is N or NR$^4$ when Y is O, and X is O when Y is N or NR$^4$;

Y is O when X is N or NR$^4$, and Y is N or NR$^4$ when X is O;

one of Z$^1$, Z$^2$, Z$^3$ or Z$^4$ is N, or NH;

R$^1$ is optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl;

R$^2$ is hydrogen, halogen, —OH, —CN, —N(C$_{0-4}$alkyl)(C$_{0-4}$alkyl), —NO$_2$; or —C$_{1-6}$alkyl, —C$_{1-4}$alkoxyl, —C$_{0-4}$alkyl-phenyl, or —C$_{1-4}$alkoxy-phenyl group, wherein any of the groups is optionally substituted with 1–3 independently halogen, —OH, —CN, or —C$_{1-4}$ alkoxyl substituents;

R$^3$ is hydrogen or —C$_{1-4}$alkoxyl;

R$^4$ is —C$_{0-4}$alkyl; and

R$^5$ is H, halogen, or —C$_{1-4}$alkyl.

2. The compound according to claim 1, or a pharmaceutically acceptable salt thereof, wherein:

Z$^1$ is N;

X is N; and

Y is O.

3. The compound according to claim 2, or a pharmaceutically acceptable salt thereof, wherein:

R$^1$ is —C$_{0-4}$alkyl-pyridyl optionally substituted with 1–5 substituents; wherein each substituent is independently halogen, —OH, —CN, —C$_{1-6}$alkyl, —C$_{1-4}$alkoxyl, —N(C$_{0-4}$alkyl)(C$_{0-4}$alkyl), —C$_{0-4}$alkyl-C(O)—O—C$_{0-4}$alkyl, —C$_{0-4}$alkyl-morpholinyl, or —C$_{0-4}$alkyl-benzoxazolyl.

4. The compound according to claim 1, or a pharmaceutically acceptable salt thereof, wherein:

Z$^2$ or Z$^3$ is N;

X is N; and

Y is O.

5. The compound according to claim 1 represented by

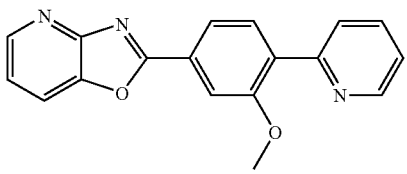

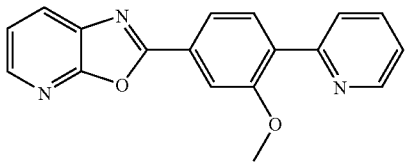

or a pharmaceutically acceptable salt thereof.

6. The compound according to claim 1 represented by

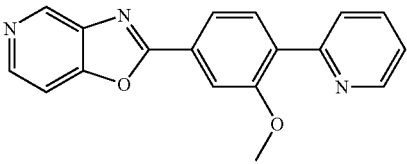

or a pharmaceutically acceptable salt thereof.

7. A pharmaceutical composition comprising a therapeutically effective amount of the compound according to claim 1 or a pharmaceutically acceptable salt thereof; and a pharmaceutically acceptable carrier.

8. A method of treatment of pain comprising the step of administering a therapeutically effective amount of the compound according to claim 1 or a pharmaceutically acceptable salt thereof.

9. A method of treatment of a pain disorder wherein said pain disorder is acute pain, persistent pain, chronic pain, inflammatory pain, or neuropathic pain, comprising the step of administering a therapeutically effective amount of the compound according to claim 1 or a pharmaceutically acceptable salt thereof.

10. A method of treatment of neuropathic pain comprising the step of administering a therapeutically effective amount of the compound according to claim 1 or a pharmaceutically acceptable salt thereof.

11. A method of treatment of inflammatory pain comprising the step of administering a therapeutically effective amount of the compound according to claim 1 or a pharmaceutically acceptable salt thereof.

* * * * *